(12) United States Patent
Majeti et al.

(10) Patent No.: US 11,377,495 B2
(45) Date of Patent: *Jul. 5, 2022

(54) MARKERS OF ACUTE MYELOID LEUKEMIA STEM CELLS

(71) Applicant: The Board of Trustees of the Leland Stanford Junior University, Stanford, CA (US)

(72) Inventors: Ravindra Majeti, Palo Alto, CA (US); Irving L. Weissman, Stanford, CA (US); Siddhartha Jaiswal, San Francisco, CA (US); Mark P. Chao, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/350,963

(22) Filed: Jun. 17, 2021

(65) Prior Publication Data
US 2022/0025041 A1     Jan. 27, 2022

Related U.S. Application Data

(63) Continuation of application No. 16/738,913, filed on Jan. 9, 2020, now Pat. No. 11,072,655, which is a continuation-in-part of application No. 15/704,790, filed on Sep. 14, 2017, now Pat. No. 10,662,242, which is a continuation of application No. 14/927,349, filed on Oct. 29, 2015, now Pat. No. 9,796,781, which is a continuation of application No. 14/164,009, filed on Jan. 24, 2014, now Pat. No. 9,193,955, which is a continuation of application No. 13/739,788, filed on Jan. 11, 2013, now Pat. No. 8,709,429, which is a continuation of application No. 12/836,152, filed on Jul. 14, 2010, now Pat. No. 8,361,736, which is a continuation-in-part of application No. PCT/US2009/000224, filed on Jan. 13, 2009.

(60) Provisional application No. 61/011,324, filed on Jan. 15, 2008.

(51) Int. Cl.
| | | |
|---|---|---|
| C07K 16/28 | (2006.01) |
| C07K 16/30 | (2006.01) |
| C12Q 1/6886 | (2018.01) |
| A61P 35/02 | (2006.01) |
| G01N 33/50 | (2006.01) |
| G01N 33/574 | (2006.01) |
| C12N 5/00 | (2006.01) |
| C12N 5/09 | (2010.01) |
| A61K 39/00 | (2006.01) |

(52) U.S. Cl.
CPC .......... *C07K 16/2803* (2013.01); *A61P 35/02* (2018.01); *C07K 16/28* (2013.01); *C07K 16/2896* (2013.01); *C07K 16/30* (2013.01); *C12N 5/0093* (2013.01); *C12N 5/0694* (2013.01); *C12Q 1/6886* (2013.01); *G01N 33/5011* (2013.01); *G01N 33/57426* (2013.01); *A61K 2039/505* (2013.01); *A61K 2039/507* (2013.01); *C07K 2317/24* (2013.01); *C07K 2317/73* (2013.01); *C07K 2317/75* (2013.01); *C07K 2317/76* (2013.01); *C12Q 2600/112* (2013.01); *C12Q 2600/136* (2013.01); *G01N 2500/04* (2013.01)

(58) Field of Classification Search
CPC ................ C07K 16/2803; C07K 16/28; C07K 16/2896; C07K 16/30; A61P 35/02; C12N 5/0093; C12N 5/0694; C12Q 1/6886; G01N 33/5011; G01N 33/57426; A61K 2039/505
USPC ....................................................... 424/133.1
See application file for complete search history.

(56) References Cited

U.S. PATENT DOCUMENTS

| | | | |
|---|---|---|---|
| 4,867,973 A | 9/1989 | Goers et al. | |
| 6,465,247 B1 | 10/2002 | Weissman et al. | |
| 6,491,917 B1 | 12/2002 | Thomas et al. | |
| 6,733,743 B2 | 5/2004 | Jordan | |
| 7,514,229 B2 | 4/2009 | Jamieson | |
| 8,361,736 B2 | 1/2013 | Majeti et al. | |
| 8,562,997 B2 | 10/2013 | Jaiswal et al. | |
| 8,758,750 B2 | 6/2014 | Weissman et al. | |
| 9,399,682 B2 | 7/2016 | Jaiswal et al. | |
| 10,662,242 B2 * | 5/2020 | Majeti .................... | C07K 16/28 |
| 10,781,256 B2 | 9/2020 | Weiskopf et al. | |
| 2004/0213792 A1 | 10/2004 | Clemmons et al. | |
| 2005/0118164 A1 | 6/2005 | Hermon | |

(Continued)

FOREIGN PATENT DOCUMENTS

| | | |
|---|---|---|
| EP | 1693385 | 8/2006 |
| EP | 2111869 | 10/2009 |

(Continued)

OTHER PUBLICATIONS

Agerstam et al. (2015) "Antibodies targeting human IL1RAP (IL1R3) show therapeutic effects in xenograft models of acute myeloid leukemia" A Proceedings of The National Academy of Sciences 112:34 10786-10791.

(Continued)

*Primary Examiner* — Yan Xiao
(74) *Attorney, Agent, or Firm* — Pamela J. Sherwood; Bozicevic, Field & Francis LLP

(57) ABSTRACT

Markers of acute myeloid leukemia stem cells (AMLSC) are identified. The markers are differentially expressed in comparison with normal counterpart cells, and are useful as diagnostic and therapeutic targets.

7 Claims, 51 Drawing Sheets

Specification includes a Sequence Listing.

(56) References Cited

U.S. PATENT DOCUMENTS

| | | |
|---|---|---|
| 2005/0142539 A1 | 6/2005 | Herman et al. |
| 2006/0239910 A1 | 10/2006 | Nicolaides et al. |
| 2007/0111238 A1 | 5/2007 | Atriona et al. |
| 2007/0113297 A1 | 5/2007 | Yang et al. |
| 2007/0287163 A1 | 5/2007 | Yang et al. |
| 2008/0107654 A1 | 5/2008 | Kikuchi et al. |
| 2008/0131431 A1 | 6/2008 | Smith et al. |
| 2008/0187950 A1 | 8/2008 | Weissman et al. |
| 2009/0191202 A1 | 7/2009 | Jamieson et al. |
| 2010/0255575 A1 | 10/2010 | Weissman et al. |

FOREIGN PATENT DOCUMENTS

| | | |
|---|---|---|
| JP | 2001-503253 | 3/2001 |
| JP | 2003-518514 | 6/2003 |
| JP | 2004-504408 | 2/2004 |
| JP | 2005-333993 | 12/2005 |
| JP | 6280161 | 2/2018 |
| WO | WO 1999/10478 | 3/1999 |
| WO | WO 1999/40940 | 8/1999 |
| WO | WO 2003/074567 | 9/2003 |
| WO | WO 2005/044857 | 5/2005 |
| WO | WO 2006/89133 | 8/2006 |
| WO | WO 2007/121465 | 10/2007 |
| WO | WO 2007/133811 | 11/2007 |
| WO | WO 2009/046541 | 4/2009 |
| WO | WO 2009/091547 | 7/2009 |
| WO | WO 2009/091601 | 7/2009 |
| WO | WO 2009/131453 | 10/2009 |
| WO | WO 2010/17332 | 2/2010 |
| WO | WO 2011/034969 | 3/2011 |

OTHER PUBLICATIONS

Alinari et al. (2007) "Alemtuzumab (Campath-1H) in the treatment of chronic lymphocytic leukemia" Oncogene 26: 3644-3653.
Arsenijevic et al. (2001) "Phagocytic Activity of Monocytes in Patients with Breast Cancer at Different Clinical Stages" Breast Cancer Research 3:Suppl S1-S24, Abstract "A4".
Avidity IP Limited, Notice of Opposition to European Patent EP2242512, Jan. 26, 2017, pp. 1-36.
Baxter et al. (2005) "Acquired mutation of the tyrosine kinase JAK2 in human myeloproliferative disorders" The Lancet 365: 1054-1061.
Berenbaum (1977) "Synergy, additivism and antagonism in immunosuppression. A Critical Review", Clinical and Experimental Immunology 28: 1-18.
Beuzeboc et al. (2007) "Trastuzumab (T) combined with standard chemotherapy in HER+ metastatic bladder (BC) patients Interim safety results of a prospective randomized phase II Study" Journal of Clinical Oncology 25: 18 suppl, 15565-15565.
Blink Biomedical SAS, Notice of Opposition to European Patent EP2242512, Jan. 26, 2017, pp. 1-42.
Bookman et al. (2003) "Evaluation of Monoclonal Humanized Anti-HER2 Antibody, Trastuzumab, in Patients With Recurrent or Refractory Ovarian or Primary Peritoneal Carcinoma With Over expression of HER2: A Phase II Trial of the Gynecologic Oncology Group" Journal of Clinical Oncology 21: 283-290.
Bristol-Myers Squibb Company, Notice of Opposition to European Patent European Patent EP2242512, Jan. 26, 2017, pp. 1-29.
Brooke et al. (2004) "Human Lymphocytes Interact Directly with CD47 Through a Novel Member of the Signal Regulatory Protein (SIRP) Family" The Journal of Immunology 173: 2562-2570.
Burger et al. (2007) "Phase II Trial of Bevacizumab in Persistent or Recurrent Epithelial Ovarian Cancer or Primary Peritoneal Cancer: A Gynecologic Oncology Group Study" Journal of Clinical Oncology 25:33 p. 165-5172.
Chan et al. (2009) "Identification, molecular characterization, clinical prognosis, and therapeutic targeting of human bladder tumor-initiating cells", Proceedings of the National Academy of Sciences of the United States of America 106:33 14016-14021.
Chao et al. (2011) "Therapeutic antibody targeting of CD47 eliminates human acute lymphoblastic leukemia" Cancer Research 71:4 1374-1384.
Clarke et al. (2006) "Cancer stem cells—perspectives on current status and future directions: AACR Workshop on cancer stem cells" Cancer Research 66:19 9339-9344.
Clynes et al. (2000) "Inhibitory Fc Receptors Modulate in vivo Cytoxicity Against Tumor Targets" Nature Medicine 6: 443-446.
Coiffier (2005) "State-of-the-Art Therapeutics: Diffuse Large B-Cell Lymphoma" Journal of Clinical Oncology 23:26 6387-6393.
Conrad et al. (2006) "Inflammatory Cytokines Predominate in Cases of Tumor Regression after Hematopoietic Stem Cell Transplantation for Solid Cancer" Biology and Blood and Bone Marrow Transplantation 12:3 346-354.
Declaration of Randolph Wall, Ph.D. 107 Pages.
Demeure et al. (2000) "CD47 Engagement inhibits cytokine production and maturation of human dendritic cells" The Journal of Immunology 164: 2193-2199.
Durando et al. (2003) "High-dose BCNU followed by autologous hematopoietic stem cell transplantation in supratentorial high-grade malignant gliomas: a retrospective analysis of 114 patients" Bone Marrow Transplantation 31:7 559-564.
Eichler (2000) "CD97 isoform expression in leukocytes" Journal of Leukocyte Biology 68:4 561-567.
Fey (2003) "ESMO Minimum Clinical Recommendations for diagnosis, treatment and follow-up of acute myeloblastic leukaemia (AML) in adult patients" Annals of Oncology 14:8 1161-1162.
Forty Seven, Inc., Petition For Inter Partes Review of U.S. Pat. No. 9,352,037, Filed: Aug. 5, 2016, Case No. PR2016-01529, 74 Pages.
Forty Seven, Inc., Petition For Inter Partes Review of U.S. Pat. No. 9,352,037, Filed: Aug. 8, 2016, Case No. PR2016-01530, 76 Pages.
Fuchs et al. (2004) "Cutting Edge: CD96 (Tactile) Promotes NK Cell-Target Cell Adhesion by Interacting with the Poliovirus Receptor (CD155)" Journal of Immunology 172:7 3994-3998.
Gibson et al. (2002) "Phase III Trial of a Humanized Anti-CD33 Antibody (HuM195) in Patients with Relapsed or Refractory Acute Myeloid Leukemia" Clinical Lymphoma 3:1 18-19.
Gleason et al. (2012) "Tim-3 is an inducible human natural killer cell receptor that enhances interferon gamma production in response to galectin-9" Blood 1-42.
Gökbuget et al. (2006) "Novel antibody-based therapy for acute lymphoblastic leukaemia" Best Practice & Research Clinical Haematology 19: 701-713.
Harmsen et al. (2007) "Properties, production, and applications of camelid single-domain antibody fragments" Applied Microbiology and Biotechnology 77: 13-22.
Hatherley et al. (2008) "Paired receptor specificity explained by structures of signal regulatory proteins alone and complexed with CD47" Molecular Cellular 31:2 266-277.
Heibeis et al. (2005) "Vav proteins are required for B-lymphocyte responses to LPS" Blood 106:2 635-640.
Hosen et al. (2007) "CD96 is a leukemic stem cell-specific marker in human acute myeloid leukemia" Proceedings of the National Academy of Sciences of the United States of America 104:26 11008-11013.
Ide et al. (2007) "Role for CD47—SIRPα signaling in xenograft rejection by macrophages" Proceedings of the National Academy of Sciences of the United States of America 104:12 5062-5066.
Imai et al., "Comparing antibody and small-molecule therapies for cancer", Nature Reviews/Cancer, Sep. 2006, pp. 714-727, vol. 6, Nature Publishing Group, London, United Kingdom.
Imayoshi et al. (2006) "Expression of CD180, a toll-like receptor homologue, is up-regulated in children with Kawasaki disease" Journal of Molecular Medicine 84:2 168-174.
Imbert et al. (2006) "CD99 expressed on human mobilized peripheral blood CD34+ cells is involved in transendothelial migration" Blood 108:8 2578-2586.
Ishikawa et al. (2007) "Chemotherapy-resistant human AML stem cells home to and engraft within the bone-marrow endosteal region" Nature Biotechnology 25:11 1315-1321.

(56) References Cited

OTHER PUBLICATIONS

Jaiswal et al. (2010) "Macrophages as mediators of tumor immunosurveillance" Trends in Immunology 31:6 212-219.
James et al. (2005) "A unique clonal JAK2 mutation leading to constitutive signaling causes polycythaemia vera" Nature 434: 1144-1148.
Jamieson et al. (2004) "Chronic versus acute myelogenous leukemia: A question of self-renewal" Cancer Cell 531-533.
Jamieson et al. (2004) "Granulocyte-macrophage progenitors as candidate leukemic stem cells in blast-crisis CML" New England Journal of Medicine 351:7 657-667.
Jamieson et al. (2005) "Increased expression of CD47 is a constant marker in mouse and human myeloid leukemias" Blood (ASH Annual Meeting Abstracts) 106:911 A.
Jan et al. (2011) "Prospective separation of normal and leukemic stem cells based on differential expression of TIM3, a human acute myeloid leukemia stem cell marker" Proceedings of the National Academy of Sciences of the United States of America 108:12 5009-5014.
Jin et al. (2006) "Targeting of CD44 eradicates human acute myeloid leukemic stem cells" Nature Medicine 12:10 1167-1174.
Kikuhige et al. (2010) "TIM-3 is a promising target to selectively kill acute myeloid leukemia stem cells" Cell Stem Cell 7:6 708-717.
Kim et al. (2005) "Antibody Engineering for the Development of Therapeutic Antibodies" Molecules and Cells 20:1 17-29.
Kovacsovics-Bankowski et al. (1993) "Efficient major histocompatibility complex class I presentation of exogenous antigen upon phagocytosis by macrophages" Proceedings of the National Academy of Sciences of the United States of America 90: 4942-4946.
Kravolics et al. (2005) "A gain-of-function mutation of JAK2 in myeloproliferative disorders" New England Journal of Medicine 352:17 1779-1790.
Levesque et al. (2007) "Mobilization of bone marrow-derived progenitors" Handbook of Experimental Pharmacology 180: 3-36.
Levine, R., et al. (2005) "Activating mutation in the tyrosine kinase JAK2 in polycythemia vera, essential thrombocythemia, and myeloid metaplasia with myelofibrosis" Cancer Cell 7: 387-397.
Liu et al. (2002)"Signal regulatory protein (SIRPalpha), a cellular ligand for CD47, regulates neutrophil transmigration" Journal of Biological Chemistry, 227:12 10028-10036.
Majeti et al. (2008) "CD47 Is an Independent Prognostic Factor and Therapeutic Antibody Target on Human Acute Myeloid Leukemia Stem Cells" Blood 112:11.
Majeti et al. (2009) "CD47 is an adverse prognostic factor and therapeutic antibody target on human acute myeloid leukemia stem cells" Developmental Cell 138:2 286-299.
Manna et al. (2003) "The mechanism of CD47-dependent killing of T cells: heterotrimeric Gi-dependent inhibition of protein kinase A" Journal of Immunology 170:7 3544-3553.
Manna et al. (2004) "CD47 mediates killing of breast tumor cells via Gi-dependent inhibition of protein kinase A." Cancer Research 64:3 1026-1036.
Martin-Subero et al.,"Amplification of ERBB2, RARA, and TOP2A genes in a myelodysplastic syndrome transforming to acute myeloid leukemia" Cancer Genetics and Cytogenetics 127:2 174-176.
Matuso et al. (1997) "Two acute monocytic leukemia (AML-M5a) cell lines (MOLM-13 and MOLM-14) with interclonal phenotypic heterogeneity showing MLL-AF9 fusion resulting from an occult chromosome insertion, ins(11 ;9)(q23;p22p23)" Leukemia 11:9 1469-1477.
Mawby et al. (1994) "Isolation and characterization of CD47 glycoprotein: a multispanning membrane protein which is the same as integrin-associated protein (IAP) and the ovarian tumour marker OA3" Biochemical Journal 304:2 525-530.
Mazurier et al. (1999) "A Novel Immunodeficient Mouse Modei-RAG2 X Common Cytokine Receptor y Chain Double Mutants-Requiring Exogenous Cytokine Administration for Human Hematopoietic Stem Cell Engraftment" 19: Journal of Interferon and Cytokine Research 533-541.

McCormack et al. (2005) "Animal models of acute myelogenous leukemia—development, application and future perspectives" Leukemia 19: 687-706.
McDonald et al. (2004) "Cholesterol-independent interactions with CD47 enhance alphavbeta3 avidity" Journal of Biological Chemistry 279:17 17301-17311.
Metayer et al. (2017) "Anti-CD47 antibodies induce phagocytosis of live, malignant B cells by macrophages via the Fc domain, resulting in cell death by phagoptosis" Oncotarget 8:37 60892-60903.
Motegi et al. (2003) "Role of the CD47-SHPS-1 system in regulation of cell migration" European Molecular Biology Organization Journal 22:11 2634-2644.
Musolino et al. (2008) "Immunoglobulin G Fragment C Receptor Polymorphisms and Clinical Efficacy of Trastuzumab-Based Therapy in Patients With HER-2/neu-Positive Metastatic Breast Cancer" Journal of Clinical Oncology 26:11 1789-1796.
NCBI protein database-SIRP alpha. Jun. 6, 2006, pp. 1-3.
Okazawa et al. (2005) "Negative Regulation of Phagocytosis in Macrophages by the CD47-SHPS-1 System" The Journal of Immunology 174: 2004-2011.
Oldenborg et al. (2000) "Role of CD47 as a Marker of Self on Red Blood Cells" Science 288:5473 2051-2054.
Oldenborg et al. (2001) "Cd47-Signal Regulatory Protein α (Sirpα) Regulates Fcγ and Complement Receptor-Mediated Phagocytosis" Journal of Experimental Medicine 193:7 855-861.
Ouban et al. (2003) "Expression and Distribution of Insulin-Like Growth Factor-1 Receptor in Human Carcinomas" Human Pathology 34:8 803-808.
Ozols (2006) "Challenges for chemotherapy in ovarian cancer" Annals of Oncology 7:5 v181-v187.
Passegué et al. (2004) "JunB deficiency leads to a myeloproliferative disorder arising from hematopoietic stem cells" Cell 119: 431 -443.
Pettersen et al. (1999) "CD47 signals T cell death" Journal of Immunology 162:12 7031-7040.
Pietsch et al. (2017) "Anti-leukemic activity and tolerability of anti-human CD47 monoclonal antibodies" Blood Cancer Journal 7:e536 1-25.
Schlom (1991) "Monoclonal Antibodies: They're More and Less Than You Think" Molecular Foundations of Oncology 95-134.
Shahan et al. (1999) "Identification of CD47/integrin-associated protein and alpha(v)beta3 as two receptors for the alpha3(IV) chain of type IV collagen on tumor cells" Cancer Research 59: 4584-4590.
Shi et al. (2020) "The identification of a CD47-blocing "hotspot" and design of a CD47/PD-L1 dual-specific antibody with limited hemagglutination", Signal transduction and targeted therapy, vol. 5:16, p. 3.
Strawman Limited, Notice of Opposition to European Patent EP2242512, Jan. 27, 2017, pp. 1-36.
Subramanian; et al. (2006) "Species- and cell type-specific interactions between CD47 and human SIRPalpha" Blood 107:6 2548-2556.
Surface Oncology, Inc., Notice of Opposition to European Patent EP2242512, Jan. 27, 2017, pp. 1-45.
Sutherland et al. (1996) "Characterization of a hierarchy in human acute myeloid leukemia progenitor cells" Blood 87:11 4754-4761.
Tibes et al. (2006) "Activity of Alemtuzumab in Patients with CD52-Positive Acute Leukemia" Cancer 106:12 2645-2651.
Tioma Therapeutics, Inc., Notice of Opposition to European Patent EP2242512, Jan. 20, 2017, pp. 1-40.
Valneva Austria GMBH, Third Party Observation for Publication No. EP2242512, Filed on Jan. 15, 2009, 4 Pages.
Veillette et al. (1998) "High Expression of Inhibitory Receptor SHPS-1 and Its Association with Protein-tyrosine Phosphatase SHP-1 in Macrophages", The Journal of Biological Chemistry 273:35 22719-22728.
Vigna et al. (2002) "Robust and Efficient Regulation of Transgene Expression in Vivo by Improved Tetracycline-Dependent Lentiviral Vectors" Molecular Therapy 5:3 252-261.
Wall "Curriculum Vitae" 9 pages.

(56) References Cited

OTHER PUBLICATIONS

Weisenthal (2012) "Synergy analysis of "classic" and newer drug combinations" Human Tumor Assay Journal on-line at http://lweisenthal.org/synergy1.htm.

White et al. (2003) "Monoclonal antibodies inhibit prion replication and delay the development of prion disease" Nature 422:6927 80-83.

Wilding, Notice of Opposition to European Patent EP2242512, Jan. 26, 2017, pp. 1-52.

Willingham et al. (2012) "The CD47-signal regulatory protein alpha (SIRPa) interaction is a therapeutic target for human solid tumors" Proceedings of the National Academy of Sciences of the United States of America 109:17 6662-6667.

Younes et al. (2003) "A pilot study of rituximab in patients with recurrent, classic Hodgkin disease" Cancer 98:2 310-314.

Zengers et al. (1975) "Studies on FD Fragments of Human Immunoglobulins" Scandinavian Journal of Immunology 4:2 161-169.

Zhao et al. (2011) "CD47-signal regulatory protein-a {SIRPa) interactions form a barrier for antibody-mediated tumor cell destruction" Proceedings of the National Academy of Sciences of the United States of America 108:45 18342-18347.

Zhao et al. (2012) "Is targeting of CD47-SIRPa enough for treating hematopoietic malignancy?" Blood 119:18 4333-4334.

Zheng et al. (2006) "Gene expression profiling of CD34+ cells identifies a molecular signature of chronic myeloid leukemia blast crisis" Leukemia 20:6 1028-1034.

\* cited by examiner

B

| Population | # CB Samples | Median Cells Injected (Range) | % Mice with Human Engraftment | Ave % Human Chimerism (Range) | Ave % Myeloid Cells (Range) | Ave % B Cells (Range) |
|---|---|---|---|---|---|---|
| 90+RA- | 6 | 500 (100-3600) | 92% (12/13) | 3.7% (0.3-12.5) | 6.7% (1.3-13.5) | 73.4% (57.1-86.4) |
| 90-RA- | 6 | 900 (240-4440) | 88% (15/17) | 4.0% (0.1-27.2) | 7.1% (0.9-25.7) | 61.2% (16.3-83.0) |
| 90-RA+ | 5 | 781 (500-900) | 0% (0/14) | 0% | N/A | N/A |

C

B

| Population | # CB Samples | Median Cells Injected (Range) | % Mice with Human Engraftment | Ave % Human Chimerism (Range) | Ave % Myeloid Cells (Range) | Ave % B Cells (Range) |
|---|---|---|---|---|---|---|
| 90+RA- | 4 | 500 (206-508) | 100% (8/8) | 19.9% (8.8-35.6) | 24.3% (5.2-58.6) | 63.2% (35.2-86.1) |
| 90-RA- | 4 | 500 (240-2391) | 89% (8/9) | 4.4% (0.5-13.8) | 26.6% (1.8-55.1) | 64.6% (41.7-87.3) |
| 90-RA+ | 3 | 646 (500-781) | 0% (0/8) | 0% | N/A | N/A |

| Population | # CB Samples | Cells Injected | % Mice with Active Human Engraftment | Ave % Human Chimerism (Range) | Ave % Myeloid Cells (Range) | Ave % B Cells (Range) |
|---|---|---|---|---|---|---|
| 90+RA- | 2 | 50 (n=3), 70 (n=1) | 100% (4/4) | 4.7% (0.5-10.5) | 13.2% (8.6-18.0) | 78.9% (73.6-81.2) |
| 90-RA- | 2 | 50 (n=3), 70 (n=2) | 0% (0/5) | 0.04% (0-0.2) | 0% (all 0) | 0% (all 0) |

| Population | # CB Samples | Median Cells Injected (Range) | % Mice with Human Engraftment | Ave % hCD34+ of Total BM (Range) | Ave % 34+38+ of Lin-34+ (Range) | Ave % 34+38- of Lin-34+ (Range) |
|---|---|---|---|---|---|---|
| 90+RA- | 4 | 500 (206-508) | 100% (8/8) | 6.4% (0.8-13.2) | 82.2% (72.2-93.2) | 17.5% (5.7-28.8) |
| 90-RA- | 4 | 500 (240-2391) | 89% (8/9) | 1.3% (0.5-2.5) | 81.2% (70.8-92.1) | 18.5% (7.9-29.2) |
| 90-RA+ | 3 | 646 (500-781) | 0% (0/8) | 0% | N/A | N/A |

| Genebank | Gene Symbol | Gene | HSC Fold Change | MPP Fold Change |
|---|---|---|---|---|
| NM_005816 | CD96 | CD96 antigen | 57.5 | 66.7 |
| NM_002182 | IL1RAP | interleukin 1 receptor accessory protein | 31.0 | 31.0 |
| NM_003332 | TYROBP | TYRO protein tyrosine kinase binding protein | 27.5 | 27.4 |
| NM_004271 | LY86 | lymphocyte antigen 86 | 26.9 | 37.3 |
| NM_005048 | PTHR2 | parathyroid hormone receptor 2 | 18.4 | 19.2 |
| AI625747 | ADRB1 | Adrenergic, beta-1-, receptor | 17.7 | 16.0 |
| U62027 | C3AR1 | complement component 3a receptor 1 | 16.8 | 19.6 |
| AW025572 | HAVCR2 | hepatitis A virus cellular receptor 2 | 14.5 | 15.1 |
| AF285447 | HCST | hematopoietic cell signal transducer | 12.5 | 11.4 |
| AI805323 | LGR7 | leucine-rich repeat-containing GPCR 7 | 11.9 | 9.8 |
| NM_018092 | NETO2 | neuropilin (NRP) and tolloid (TLL)-like 2 | 11.5 | 13.1 |
| BF439675 | CD69 | CD69 antigen | 10.9 | 6.9 NS |
| NM_001769 | CD9 | CD9 antigen | 10.5 | 11.0 NS |
| NM_005582 | CD180 | CD180 antigen | 8.8 | 10.9 |
| AF039686 | GPR34 | G protein-coupled receptor 34 | 7.5 | 10.5 |
| AI056776 | ITGA6 | Integrin, alpha 6 | 7.3 | 11.3 |
| NM_005296 | GPR23 | G protein-coupled receptor 34 | 6.6 NS | 10.5 |
| M81695 | ITGAX | Integrin, alpha X | 6.1 NS | 9.1 |
| NM_001784 | CD97 | CD97 antigen | 5.6 NS | 7.8 NS |
| BG230614 | CD47 | CD47 antigen | 3.8 | 4.5 |
| NM_001560 | IL13RA1 | interleukin 13 receptor, alpha 1 | 3.8 NS | 7.9 |
| NM_002183 | IL3RA | CD123 antigen | 3.8 | 3.4 |
| NM_001772 | CD33 | CD33 antigen | 3.7 | 4.8 |
| BF513346 | CD99 | CD99 antigen | 3.2 | 4.5 |
| U94903 | CD44 | CD44 antigen | 2.3 | 2.8 |

A

B

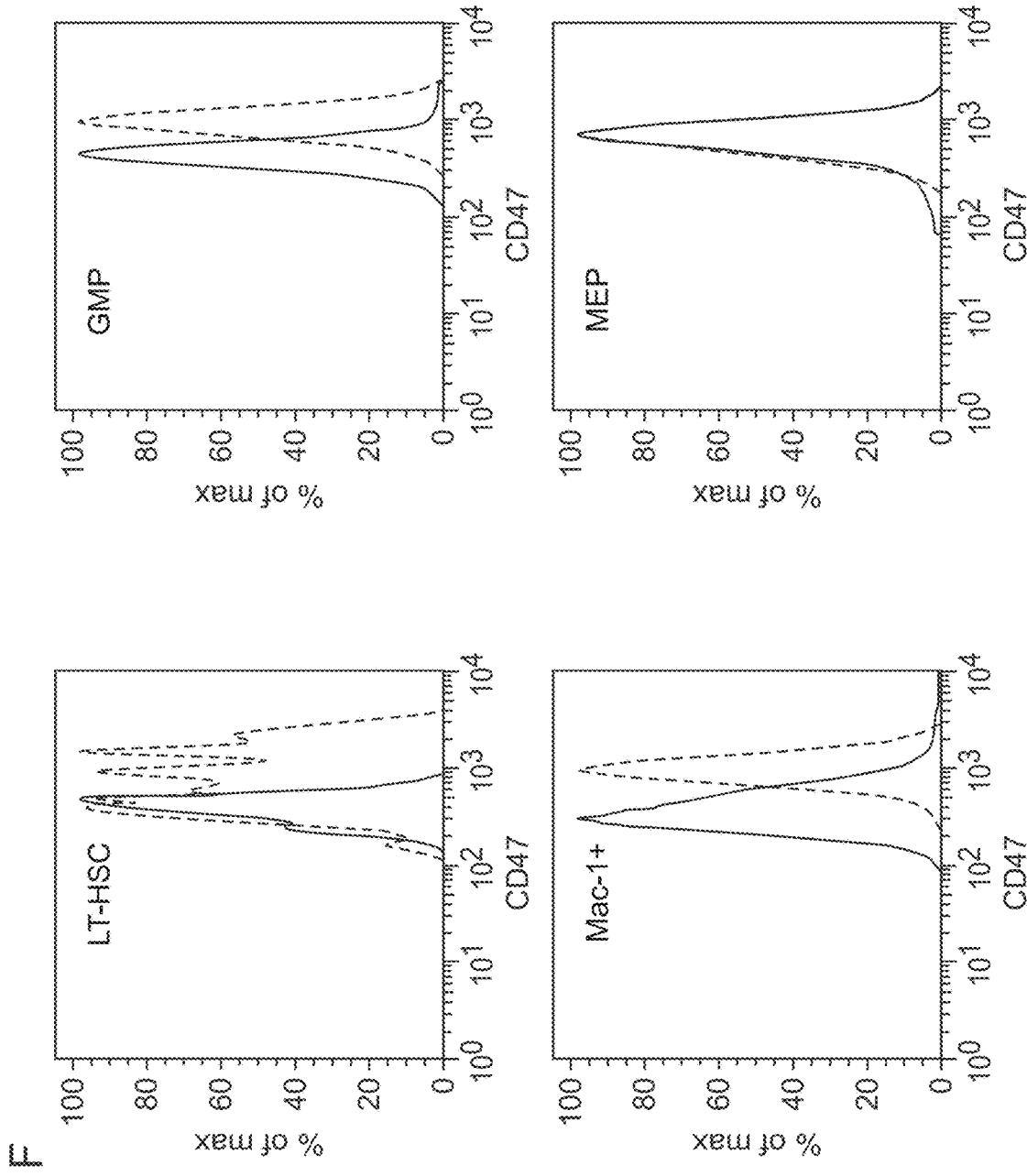

F

G

D (Cont.)

Liver

D (Cont.)

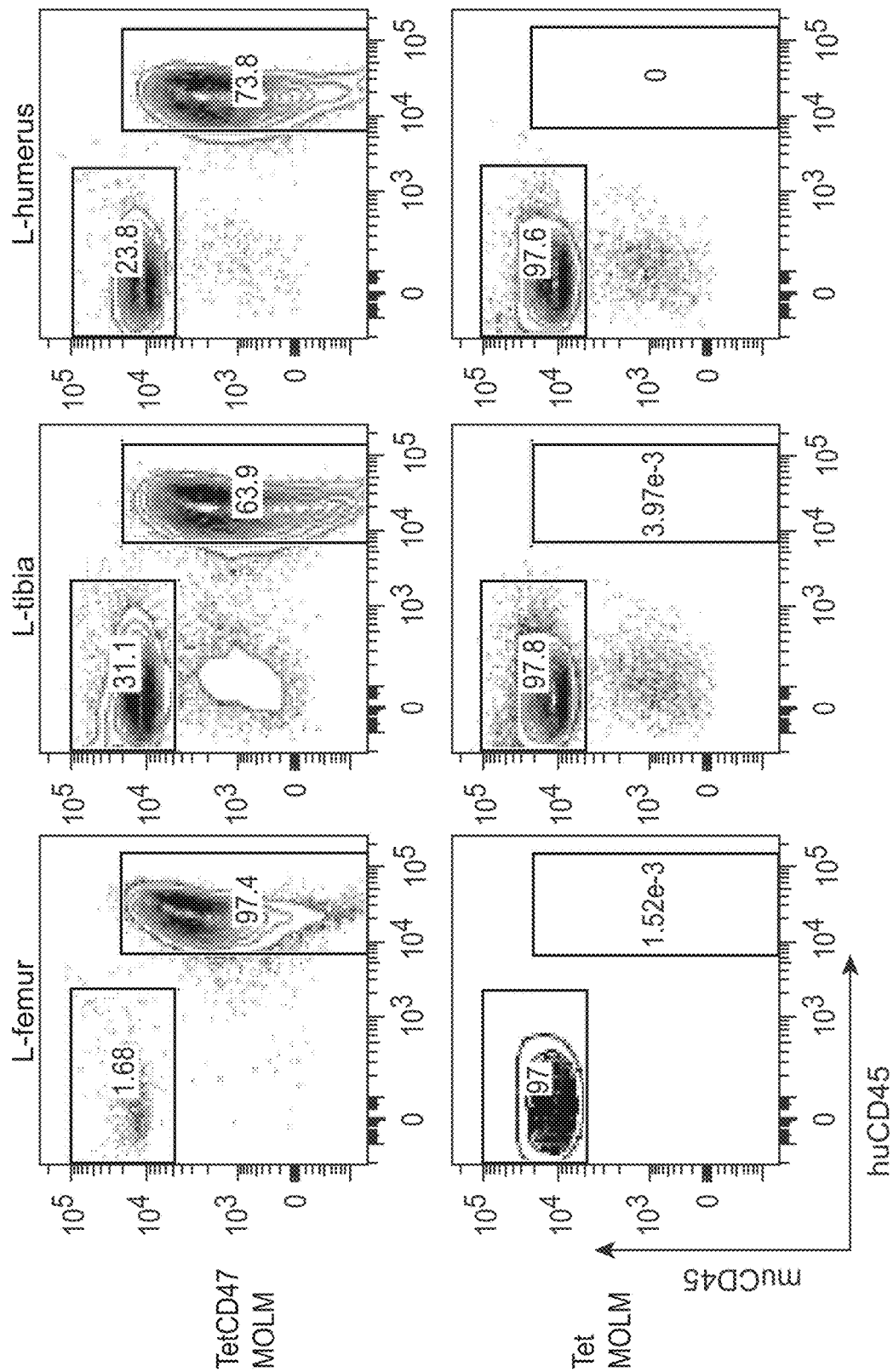

A (Cont.)

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
gggctgtctg gagtttgatg                                             20

<210> SEQ ID NO 2
<211> LENGTH: 22
```

```
<212> TYPE: DNA
<213> ORGANISM: Artificial Sequence
<220> FEATURE:
<223> OTHER INFORMATION: synthetic primer

<400> SEQUENCE: 2
tcctcttctc ctcattctgc tc                                            22

<210> SEQ ID NO 3
<211> LENGTH: 23
<212> TYPE: DNA
<213> ORGANISM: Artificial Sequence
<220> FEATURE:
<223> OTHER INFORMATION: synthetic primer

<400> SEQUENCE: 3
gcaatttagg tatgaaagcc agc                                           23

<210> SEQ ID NO 4
<211> LENGTH: 23
<212> TYPE: DNA
<213> ORGANISM: Artificial Sequence
<220> FEATURE:
<223> OTHER INFORMATION: synthetic primer

<400> SEQUENCE: 4
ctttcagcat tttgacggca acc                                           23
```

MARKERS OF ACUTE MYELOID LEUKEMIA STEM CELLS

CROSS REFERENCE

This application claims benefit and is a Continuation of application Ser. No. 16/738,913, filed Jan. 9, 2020, which is a Continuation in part of application Ser. No. 15/704,790 filed Sep. 14, 2017, now U.S. Pat. No. 10,662,242 issued May 26, 2020, which is a Continuation of application Ser. No. 14/927,349 filed Oct. 29, 2015, now U.S. Pat. No. 9,796,781 issued Oct. 24, 2017, which is a Continuation of application Ser. No. 14/164,009 filed Jan. 24, 2014, now U.S. Pat. No. 9,193,955 issued Nov. 24, 2015, which is a Continuation of application Ser. No. 13/739,788 filed Jan. 11, 2013, now U.S. Pat. No. 8,709,429 issued Apr. 29, 2014, which is a Continuation of application Ser. No. 12/836,152 filed Jul. 14, 2010, now U.S. Pat. No. 8,361,736 issued Jan. 29, 2013, which is a Continuation in Part and claims the benefit of PCT Application No. PCT/US2009/000224, filed Jan. 13, 2009, which claims benefit of U.S. Provisional Patent Application No. 61/011,324, filed Jan. 15, 2008, which applications are incorporated herein by reference in their entirety.

FEDERALLY SPONSORED RESEARCH AND DEVELOPMENT

This invention was made with Government support under contract CA086017 awarded by the National Institutes of Health. The Government has certain rights in this invention.

BACKGROUND OF THE INVENTION

Basic cancer research has focused on identifying the genetic changes that lead to cancer. This has led to major advances in our understanding of the molecular and biochemical pathways that are involved in tumorigenesis and malignant transformation. However, our understanding of the cellular biology has lagged. Although the effects of particular mutations on the proliferation and survival of model cells, such as fibroblasts or cell lines, can be predicted, the effects of such mutations on the actual cells involved in specific cancers is largely guesswork.

A tumor can be viewed as an aberrant organ initiated by a tumorigenic cancer cell that acquired the capacity for indefinite proliferation through accumulated mutations. In this view of a tumor as an abnormal organ, the principles of normal stem cell biology can be applied to better understand how tumors develop. Many observations suggest that analogies between normal stem cells and tumorigenic cells are appropriate. Both normal stem cells and tumorigenic cells have extensive proliferative potential and the ability to give rise to new (normal or abnormal) tissues. Both tumors and normal tissues are composed of heterogeneous combinations of cells, with different phenotypic characteristics and different proliferative potentials.

Because most tumors have a clonal origin, the original tumorigenic cancer cell gives rise to phenotypically diverse progeny, including cancer cells with indefinite proliferative potential, as well as cancer cells with limited or no proliferative potential. This suggests that tumorigenic cancer cells undergo processes that are analogous to the self-renewal and differentiation of normal stem cells. Tumorigenic cells can be thought of as cancer stem cells that undergo an aberrant and poorly regulated process of organogenesis analogous to what normal stem cells do. Although some of the heterogeneity in tumors arises as a result of continuing mutagenesis, it is likely that heterogeneity also arises through the aberrant differentiation of cancer cells.

It is well documented that many types of tumors contain cancer cells with heterogeneous phenotypes, reflecting aspects of the differentiation that normally occurs in the tissues from which the tumors arise. The variable expression of normal differentiation markers by cancer cells in a tumor suggests that some of the heterogeneity in tumors arises as a result of the anomalous differentiation of tumor cells. Examples of this include the variable expression of myeloid markers in chronic myeloid leukaemia, the variable expression of neuronal markers within peripheral neuroectodermal tumors, and the variable expression of milk proteins or the estrogen receptor within breast cancer.

It was first extensively documented for leukemia and multiple myeloma that only a small subset of cancer cells is capable of extensive proliferation. Because the differences in clonogenicity among the leukemia cells mirrored the differences in clonogenicity among normal hematopoietic cells, the clonogenic leukemic cells were described as leukemic stem cells. It has also been shown for solid cancers that the cells are phenotypically heterogeneous and that only a small proportion of cells are clonogenic in culture and in vivo. Just as in the context of leukemic stem cells, these observations led to the hypothesis that only a few cancer cells are actually tumorigenic and that these tumorigenic cells act as cancer stem cells.

In support of this hypothesis, recent studies have shown that, similar to leukemia and other hematologic malignancies, tumorigenic and non-tumorigenic populations of breast cancer cells can be isolated based on their expression of cell surface markers. In many cases of breast cancer, only a small subpopulation of cells had the ability to form new tumors. This work strongly supports the existence of CSC in breast cancer. Further evidence for the existence of cancer stem cells occurring in solid tumors has been found in central nervous system (CNS) malignancies. Using culture techniques similar to those used to culture normal neuronal stem cells it has been shown that neuronal CNS malignancies contain a small population of cancer cells that are clonogenic in vitro and initiate tumors in vivo, while the remaining cells in the tumor do not have these properties.

Stem cells are defined as cells that have the ability to perpetuate themselves through self-renewal and to generate mature cells of a particular tissue through differentiation. In most tissues, stem cells are rare. As a result, stem cells must be identified prospectively and purified carefully in order to study their properties. Perhaps the most important and useful property of stem cells is that of self-renewal. Through this property, striking parallels can be found between stem cells and cancer cells: tumors may often originate from the transformation of normal stem cells, similar signaling pathways may regulate self-renewal in stem cells and cancer cells, and cancers may comprise rare cells with indefinite potential for self-renewal that drive tumorigenesis.

The presence of cancer stem cells has profound implications for cancer therapy. At present, all of the phenotypically diverse cancer cells in a tumor are treated as though they have unlimited proliferative potential and can acquire the ability to metastasize. For many years, however, it has been recognized that small numbers of disseminated cancer cells can be detected at sites distant from primary tumors in patients that never manifest metastatic disease. One possibility is that immune surveillance is highly effective at killing disseminated cancer cells before they can form a detectable tumor. Another possibility is that most cancer cells lack the ability to form a new tumor such, that only the dissemination of rare cancer stem cells can lead to metastatic disease. If so, the goal of therapy must be to identify and kill this cancer stem cell population.

The prospective identification and isolation of cancer stem cells will allow more efficient identification of diagnostic markers and therapeutic targets expressed by the stem cells. Existing therapies have been developed largely against the bulk population of tumor cells, because the therapies are identified by their ability to shrink the tumor mass. However, because most cells within a cancer have limited proliferative potential, an ability to shrink a tumor mainly reflects an ability to kill these cells. Therapies that are more specifically directed against cancer stem cells may result in more durable responses and cures of metastatic tumors.

Hematopoiesis proceeds through an organized developmental hierarchy initiated by hematopoietic stem cells (HSC) that give rise to progressively more committed progenitors and eventually terminally differentiated blood cells (Bryder et al., 2006). Although the concept of the HSC was not new, it was not until 1988 that it was shown that this population could be prospectively isolated from mouse bone marrow on the basis of cell-surface markers using fluorescence-activated cell sorting (FACS) (Spangrude et al., 1988). Since that time, the surface immunophenotype of the mouse HSC has become increasingly refined, such that functional HSC can be isolated with exquisite sensitivity, resulting in a purity of 1 in 1.3 cells (Kiel et al., 2005). While our ability to prospectively isolate mouse HSC has improved dramatically over the past 20 years, our understanding of the earliest events in the human hematopoietic system lags far behind.

Cancer stem cells are discussed in, for example, Pardal et al. (2003) Nat Rev Cancer 3, 895-902; Reya et al. (2001) Nature 414, 105-11; Bonnet & Dick (1997) Nat Med 3, 730-7; Al-Hajj et al. (2003) Proc Natl Acad Sci USA 100, 3983-8; Dontu et al. (2004) Breast Cancer Res 6, R605-15; Singh et al. (2004) Nature 432, 396-401.

SUMMARY OF THE INVENTION

Markers of acute myeloid leukemia stem cells (AMLSC) are provided herein. The markers are polynucleotides or polypeptides that are differentially expressed on AMLSC as compared to normal counterpart cells. Uses of the markers include use as targets for therapeutic antibodies or ligands; as targets for drug development, and for identification or selection of AMLSC cell populations.

The AMLSC markers are useful as targets of therapeutic monoclonal antibodies for treatment of patients with de novo, relapsed, or refractory acute myeloid leukemia. Such monoclonal antibodies are also useful in the treatment of pre-leukemic conditions, such as myelodysplastic syndromes (MDS) and myeloproliferative disorders (MPDs) including: chronic myelogenous leukemia, polycythemia vera, essential thrombocytosis, agnogenic myelofibrosis and myeloid metaplasia, and others. Antibodies include free antibodies and antigen binding fragments derived therefrom, and conjugates, e.g. pegylated antibodies, drug, radioisotope, or toxin conjugates, and the like.

In some embodiments, combinations of monoclonal antibodies are used in the treatment of human AML or pre-leukemic conditions. In one embodiment, a monoclonal antibody directed against CD47, for example an antibody that blocks the interaction of CD47 with SIRPα, is combined with monoclonal antibodies directed against one or more additional AMLSC markers, e.g. CD96, CD97, CD99, PTHR2, HAVCR2, and the like, which compositions can be synergistic in enhancing phagocytosis and elimination of AML LSC as compared to the use of single antibodies.

The AMLSC markers are useful as targets of monoclonal antibodies for use in ex vivo purging of autologous stem cell products (mobilized peripheral blood or bone marrow) for use in autologous transplantation for patients with acute myeloid leukemia or the pre-leukemic conditions outlined above. Combinations of monoclonal antibodies directed against AML LSC-specific cell surface molecules, as described above, can be synergistic in eliminating LSC.

The AMLSC markers are useful in clinical diagnostic applications including, without limitation, primary diagnosis of AML or pre-leukemic conditions from blood and/or bone marrow specimens, evaluation of leukemic involvement of the cerebrospinal and other body fluids, monitoring of interval disease progression, and monitoring of minimal residual disease status.

As an alternative to monoclonal antibodies, the ligands of AMLSC markers, either as single agents or in combination, may be used to target them in AML or the pre-leukemic conditions outlined above. The ligands can be free or conjugated, for direct administration to patients or for ex vivo purging of autologous stem cell products. Some specific molecules and their ligands include, without limitation, CD155-Fc fusion protein that binds CD96; TIP39 that binds PTHR2; Galectin-9 that binds HAVCR2.

The AMLSC cells can be prospectively isolated or identified from primary tumor samples, and possess the unique properties of cancer stem cells in functional assays for cancer stem cell self-renewal and differentiation.

In some embodiments of the invention, methods are provided for detection, classification or clinical staging of acute myeloid leukemias according to the stem cells that are present in the leukemia, where greater numbers of stem cells are indicative of a more aggressive cancer phenotype. Staging is useful for prognosis and treatment. In some embodiments, a tumor sample is analyzed by histochemistry, including immunohistochemistry, in situ hybridization, and the like, for the presence of $CD34^+CD38^-$ cells that express one or more AMLSC markers provided herein. The presence of such cells indicates the presence of AMLSC.

In another embodiment of the invention, methods for the isolation of AMLSC are provided, comprising contacted a candidate cell population with a binding reagent specific for one or more of the AMLSC markers provided herein, and selecting for cells that have bound to the reagent(s). The cells may further be selected as being $CD34^+CD38^-$. The cells are useful for experimental evaluation, and as a source of lineage and cell specific products, including mRNA species useful in identifying genes specifically expressed in these cells, and as targets for the discovery of factors or molecules that can affect them. AMLSC may be used, for example, in a method of screening a compound for an effect on the cells. This involves combining the compound with the cell population of the invention, and then determining any modulatory effect resulting from the compound. This may include examination of the cells for viability, toxicity, metabolic change, or an effect on cell function. The phenotype of AMLSC described herein provides a means of predicting disease progression, relapse, and development of drug resistance.

DETAILED DESCRIPTION OF THE EMBODIMENTS

Figure 1:
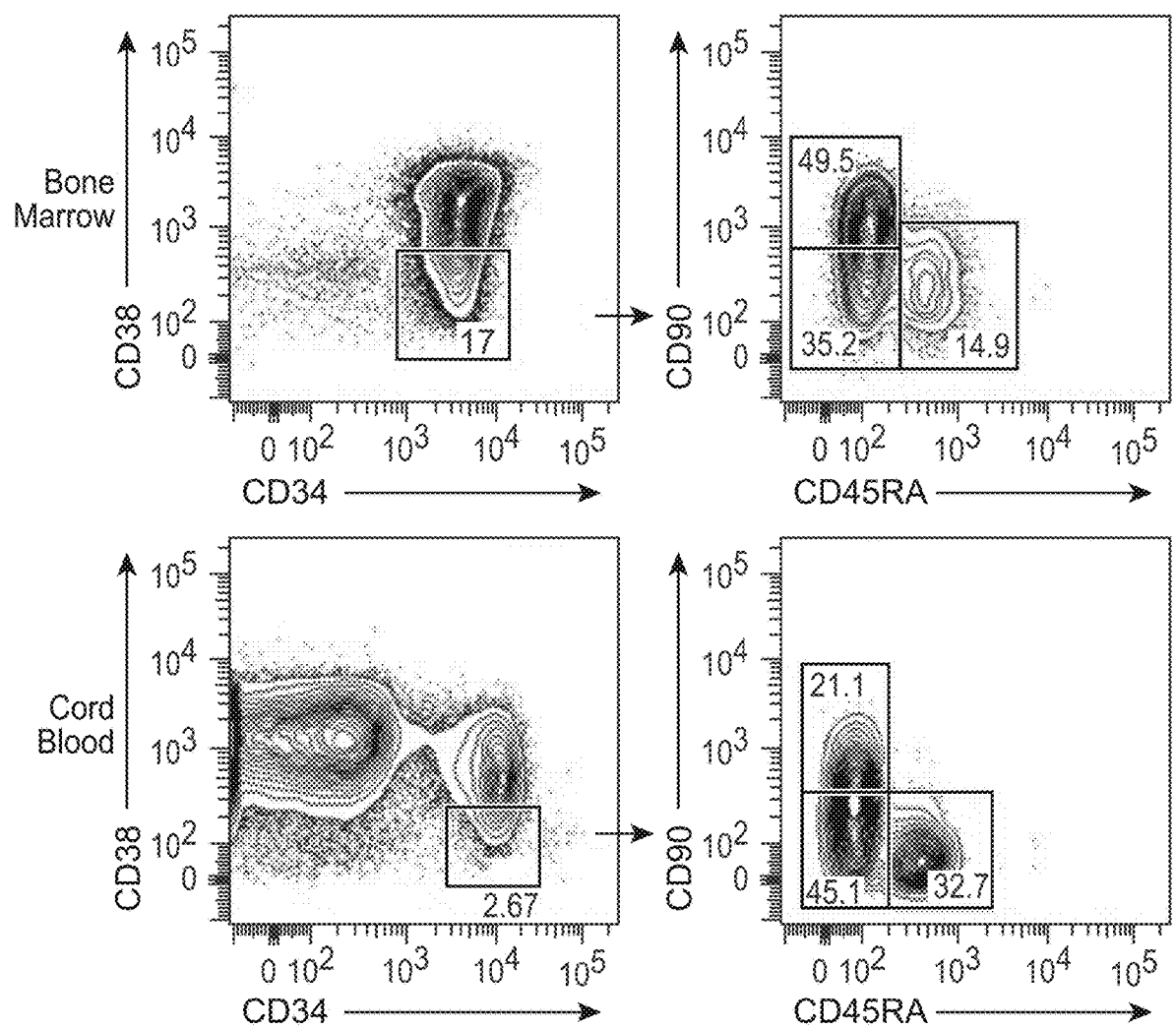
FIG. 1: Identification of CD90/CD45RA Subpopulations of Lin−CD34+CD38− Human Bone Marrow and Cord Blood. Normal human bone marrow (top) and cord blood (bottom) were analyzed for expression of lineage markers, CD34, CD38, CD90, and CD45RA by flow cytometry. The bone marrow sample was CD34-enriched prior to analysis. The left panels are gated on lineage negative (Lin−) live cells, while the right panels are gated on Lin−CD34+CD38− cells. Data shown is representative of multiple samples of bone marrow (n=10) and cord blood (n=22).

The present invention identifies polynucleotides, as well as polypeptides encoded thereby, that are differentially expressed in acute myeloid leukemia stem cells (AMLSC). Methods are provided in which these polynucleotides and polypeptides, which may be collectively referred to as AMLSC markers, are used for detecting, assessing, and reducing the growth of cancer cells. Methods may use one or a combination of markers, where a combination may include 2, 3 or more markers, and in some embodiments will include CD47 in combination with 1, 2 or more markers. The invention finds use in the prevention, treatment, detection or research of leukemic and pre-leukemic conditions.

The markers of the invention in some embodiments are expressed on the AMLSC cell surface. In some embodiments, the markers are expressed as a level at least 2× the expression level of a counterpart non-transformed cell, e.g. a human hematopoietic stem cell, and/or a human hematopoietic multipotent progenitor cell, where expression may be determined as the level of transcription, mRNA accumulation, and/or protein accumulation. In other embodiments the markers are expressed as a level at least 3×, at least 4×, at least 5×, at least 10×, at least 20× or greater, than the expression level of a counterpart non-transformed cell.

The present invention provides methods of using the markers described herein in diagnosis of cancer, classification and treatment of leukemic and pre-leukemic conditions according to expression profiles. The methods are useful for detecting AMLSC, facilitating diagnosis of AML and the severity of the cancer (e.g., tumor grade, tumor burden, and the like) in a subject, facilitating a determination of the prognosis of a subject, and assessing the responsiveness of the subject to therapy. The detection methods of the invention can be conducted in vitro or in vivo, on isolated cells, or in whole tissues or a bodily fluid, e.g., blood, lymph node biopsy samples, and the like.

As used herein, the terms "a gene that is differentially expressed in a cancer stem cell," and "a polynucleotide that is differentially expressed in a cancer stem cell", are used interchangeably herein, and generally refer to a polynucleotide that represents or corresponds to a gene that is differentially expressed in a cancer stem cell when compared with a cell of the same cell type that is not cancerous, e.g., mRNA is found at levels at least about 25%, at least about 50% to about 75%, at least about 90%, at least about 1.5-fold, at least about 2-fold, at least about 3-fold, at least about 5-fold, at least about 10-fold, or at least about 50-fold or more, different (e.g., higher or lower). The comparison can be made between AMLSC and the normal counterpart cells a human hematopoietic stem cell (HSC), which include without limitation cells having the phenotype Lin$^-$CD34$^+$CD38$^-$CD90$^+$; or the phenotype Lin$^-$CD34$^+$CD38$^-$CD90$^+$CD45RA$^-$ and a human hematopoietic multipotent progenitor cell (MPP), which include without limitation cells having the phenotype Lin$^-$CD34$^+$CD38$^-$CD90$^-$; or the phenotype Lin$^-$CD34$^+$CD38$^-$CD90$^-$CD45RA$^-$. The term "a polypeptide marker for a cancer stem cell" refers to a polypeptide encoded by a polynucleotide that is differentially expressed in a cancer stem cell.

In some embodiments of the invention, the markers are demonstrated by flow cytometry to be present on a majority of AMLSC, when compared to human HSC or MPP, as defined above. Such markers include, without limitation, CD47, CD96, CD97 and CD99.

In other embodiments of the invention, the markers are absent on human HSC or human MPP, but are highly expressed on AMLSC. Such markers include, without limitation, those set forth in Table 2.

In other embodiments, the markers are differentially expressed on AMLSC, as compared to human HSC or MPP. Such markers include, without limitation, those set forth in Table 3.

A polynucleotide or sequence that corresponds to, or represents a gene means that at least a portion of a sequence of the polynucleotide is present in the gene or in the nucleic acid gene product (e.g., mRNA or cDNA). A subject nucleic acid may also be "identified" by a polynucleotide if the polynucleotide corresponds to or represents the gene. Genes identified by a polynucleotide may have all or a portion of the identifying sequence wholly present within an exon of a genomic sequence of the gene, or different portions of the sequence of the polynucleotide may be present in different exons (e.g., such that the contiguous polynucleotide sequence is present in an mRNA, either pre- or post-splicing, that is an expression product of the gene). An "identifying sequence" is a minimal fragment of a sequence of contiguous nucleotides that uniquely identifies or defines a polynucleotide sequence or its complement.

The polynucleotide may represent or correspond to a gene that is modified in a cancer stem cell (CSC) relative to a normal cell. The gene in the CSC may contain a deletion, insertion, substitution, or translocation relative to the polynucleotide and may have altered regulatory sequences, or may encode a splice variant gene product, for example. The gene in the CSC may be modified by insertion of an endogenous retrovirus, a transposable element, or other naturally occurring or non-naturally occurring nucleic acid.

Sequences of interest include those set forth in Table 1, which are differentially expressed in AMLSC relative to normal counterpart cells.

Methods are also provided for optimizing therapy, by first classification, and based on that information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity.

The invention finds use in the prevention, treatment, detection or research of acute myeloid leukemias. Acute leukemias are rapidly progressing leukemia characterized by replacement of normal bone marrow by blast cells of a clone arising from malignant transformation of a hematopoietic stem cell. The acute leukemias include acute lymphoblastic leukemia (ALL) and acute myelogenous leukemia (AML). ALL often involves the CNS, whereas acute monoblastic leukemia involves the gums, and AML involves localized collections in any site (granulocytic sarcomas or chloromas). AML is the most common acute leukemia affecting adults, and its incidence increases with age. While AML is a relatively rare disease overall, accounting for approximately 1.2% of cancer deaths in the United States, its incidence is expected to increase as the population ages.

The presenting symptoms are usually nonspecific (e.g., fatigue, fever, malaise, weight loss) and reflect the failure of normal hematopoiesis. Anemia and thrombocytopenia are very common (75 to 90%). The WBC count may be decreased, normal, or increased. Blast cells are usually found in the blood smear unless the WBC count is markedly decreased. The blasts of ALL can be distinguished from those of AML by histochemical studies, cytogenetics, immunophenotyping, and molecular biology studies. In addition to smears with the usual stains, terminal transferase, myeloperoxidase, Sudan black B, and specific and nonspecific esterase.

"Diagnosis" as used herein generally includes determination of a subject's susceptibility to a disease or disorder, determination as to whether a subject is presently affected by a disease or disorder, prognosis of a subject affected by a disease or disorder (e.g., identification of cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. Detection of cancerous cells is of particular interest. The term "normal" as used in the context of "normal cell," is meant to refer to a cell of an untransformed phenotype or exhibiting a morphology of a non-transformed cell of the tissue type being examined. "Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" refers to a gene or gene product that, upon modulation of its activity (e.g., by modulation of expression, biological activity, and the like), can provide for modulation of the cancerous phenotype. As used throughout, "modulation" is meant to refer to an increase or a decrease in the indicated phenomenon (e.g., modulation of a biological activity refers to an increase in a biological activity or a decrease in a biological activity).

Acute Myeloid Leukemia

Acute Myelocytic Leukemia (AML, Acute Myelogenous Leukemia; Acute Myeloid Leukemia). In AML, malignant transformation and uncontrolled proliferation of an abnormally differentiated, long-lived myeloid progenitor cell results in high circulating numbers of immature blood forms and replacement of normal marrow by malignant cells. Symptoms include fatigue, pallor, easy bruising and bleeding, fever, and infection; symptoms of leukemic infiltration are present in only about 5% of patients (often as skin manifestations). Examination of peripheral blood smear and bone marrow is diagnostic. Treatment includes induction chemotherapy to achieve remission and post-remission chemotherapy (with or without stem cell transplantation) to avoid relapse.

AML has a number of subtypes that are distinguished from each other by morphology, immunophenotype, and cytochemistry. Five classes are described, based on predominant cell type, including myeloid, myeloid-monocytic, monocytic, erythroid, and megakaryocytic. Acute promyelocytic leukemia is a particularly important subtype, representing 10 to 15% of all cases of AML, striking a younger age group (median age 31 yr) and particular ethnicity (Hispanics), in which the patient commonly presents with a coagulation disorder.

Remission induction rates range from 50 to 85%. Long-term disease-free survival reportedly occurs in 20 to 40% of patients and increases to 40 to 50% in younger patients treated with stem cell transplantation.

Prognostic factors help determine treatment protocol and intensity; patients with strongly negative prognostic features are usually given more intense forms of therapy, because the potential benefits are thought to justify the increased treatment toxicity. The most important prognostic factor is the leukemia cell karyotype; favorable karyotypes include t(15; 17), t(8;21), and inv16 (p13;q22). Negative factors include increasing age, a preceding myelodysplastic phase, secondary leukemia, high WBC count, and absence of Auer rods. The FAB or WHO classification alone does not predict response.

Initial therapy attempts to induce remission and differs most from ALL in that AML responds to fewer drugs. The basic induction regimen includes cytarabine by continuous IV infusion or high doses for 5 to 7 days; daunorubicin or idarubicin is given IV for 3 days during this time. Some regimens include 6-thioguanine, etoposide, vincristine, and prednisone, but their contribution is unclear. Treatment usually results in significant myelosuppression, with infection or bleeding; there is significant latency before marrow recovery. During this time, meticulous preventive and supportive care is vital.

Polypeptide and Polynucleotide Sequences and Antibodies

The invention provides polynucleotides and polypeptides that represent genes that are differentially expressed in human AMLSC. These polynucleotides, polypeptides and fragments thereof have uses that include, but are not limited to, diagnostic probes and primers as starting materials for probes and primers, as immunogens for antibodies useful in cancer diagnosis and therapy, and the like as discussed herein.

Nucleic acid compositions include fragments and primers, and are at least about 15 bp in length, at least about 30 bp in length, at least about 50 bp in length, at least about 100 bp, at least about 200 bp in length, at least about 300 bp in length, at least about 500 bp in length, at least about 800 bp in length, at least about 1 kb in length, at least about 2.0 kb in length, at least about 3.0 kb in length, at least about 5 kb in length, at least about 10 kb in length, at least about 50 kb in length and are usually less than about 200 kb in length. In some embodiments, a fragment of a polynucleotide is the coding sequence of a polynucleotide. Also included are variants or degenerate variants of a sequence provided herein. In general, variants of a polynucleotide provided herein have a fragment of sequence identity that is greater than at least about 65%, greater than at least about 70%, greater than at least about 75%, greater than at least about 80%, greater than at least about 85%, or greater than at least about 90%, 95%, 96%, 97%, 98%, 99% or more (i.e. 100%) as compared to an identically sized fragment of a provided sequence. as determined by the Smith-Waterman homology search algorithm as implemented in MPSRCH program (Oxford Molecular). Nucleic acids having sequence similarity can be detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under high stringency conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided polynucleotide sequences, e.g. allelic variants, genetically altered versions of the gene, etc., bind to the provided polynucleotide sequences under stringent hybridization conditions.

Probes specific to the polynucleotides described herein can be generated using the polynucleotide sequences disclosed herein. The probes are usually a fragment of a polynucleotide sequences provided herein. The probes can be synthesized chemically or can be generated from longer polynucleotides using restriction enzymes. The probes can be labeled, for example, with a radioactive, biotinylated, or fluorescent tag. Preferably, probes are designed based upon an identifying sequence of any one of the polynucleotide sequences provided herein.

The nucleic acid compositions described herein can be used to, for example, produce polypeptides, as probes for the detection of mRNA in biological samples (e.g., extracts of human cells) or cDNA produced from such samples, to generate additional copies of the polynucleotides, to generate ribozymes or antisense oligonucleotides, and as single stranded DNA probes or as triple-strand forming oligonucleotides.

The probes described herein can be used to, for example, determine the presence or absence of any one of the polynucleotide provided herein or variants thereof in a sample. These and other uses are described in more detail below. In one embodiment, real time PCR analysis is used to analyze gene expression.

The polypeptides contemplated by the invention include those encoded by the disclosed polynucleotides and the genes to which these polynucleotides correspond, as well as nucleic acids that, by virtue of the degeneracy of the genetic code, are not identical in sequence to the disclosed polynucleotides. Further polypeptides contemplated by the invention include polypeptides that are encoded by polynucleotides that hybridize to polynucleotide of the sequence listing. Thus, the invention includes within its scope a polypeptide encoded by a polynucleotide having the sequence of any one of the polynucleotide sequences provided herein, or a variant thereof.

In general, the term "polypeptide" as used herein refers to both the full length polypeptide encoded by the recited polynucleotide, the polypeptide encoded by the gene represented by the recited polynucleotide, as well as portions or fragments thereof. "Polypeptides" also includes variants of the naturally occurring proteins, where such variants are homologous or substantially similar to the naturally occurring protein, and can be of an origin of the same or different species as the naturally occurring protein. In general, variant polypeptides have a sequence that has at least about 80%, usually at least about 90%, and more usually at least about 98% sequence identity with a differentially expressed polypeptide described herein. The variant polypeptides can be naturally or non-naturally glycosylated, i.e., the polypeptide has a glycosylation pattern that differs from the glycosylation pattern found in the corresponding naturally occurring protein.

Fragments of the polypeptides disclosed herein, particularly biologically active fragments and/or fragments corresponding to functional domains, are of interest. Fragments of interest will typically be at least about 10 aa to at least about 15 aa in length, usually at least about 50 aa in length, and can be as long as 300 aa in length or longer, but will usually not exceed about 1000 aa in length, where the fragment will have a stretch of amino acids that is identical to a polypeptide encoded by a polynucleotide having a sequence of any one of the polynucleotide sequences provided herein, or a homolog thereof. A fragment "at least 20 aa in length," for example, is intended to include 20 or more contiguous amino acids from, for example, the polypeptide encoded by a cDNA, in a cDNA clone contained in a deposited library or the complementary stand thereof. In this context "about" includes the particularly recited value or a value larger or smaller by several (5, 4, 3, 2, or 1) amino acids. The protein variants described herein are encoded by polynucleotides that are within the scope of the invention. The genetic code can be used to select the appropriate codons to construct the corresponding variants. The polynucleotides may be used to produce polypeptides, and these polypeptides may be used to produce antibodies by known methods described above and below.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast higher plant, insect, and mammalian cells.

Gene products, including polypeptides, mRNA (particularly mRNAs having distinct secondary and/or tertiary structures), cDNA, or complete gene, can be prepared and used for raising antibodies for experimental, diagnostic, and therapeutic purposes. Antibodies may be used to identify AMLSC cells or subtypes. The polynucleotide or related cDNA is expressed as described herein, and antibodies are prepared. These antibodies are specific to an epitope on the polypeptide encoded by the polynucleotide, and can precipitate or bind to the corresponding native protein in a cell or tissue preparation or in a cell-free extract of an in vitro expression system.

The antibodies may be utilized for immunophenotyping of cells and biological samples. The translation product of a differentially expressed gene may be useful as a marker. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al. Cell, 96:737-49 (1999)). These techniques allow for the screening of particular populations of cells; in immunohistochemistry of biopsy samples; in detecting the presence of markers shed by cancer cells into the blood and other biologic fluids, and the like.

In many embodiments, the levels of a subject gene or gene product are measured. By measured is meant qualitatively or quantitatively estimating the level of the gene product in a first biological sample either directly (e.g. by determining or estimating absolute levels of gene product) or relatively by comparing the levels to a second control biological sample. In many embodiments the second control biological sample is obtained from an individual not having cancer. As will be appreciated in the art, once a standard control level of gene expression is known, it can be used repeatedly as a standard for comparison. Other control samples include samples of cancerous tissue.

The methods can be used to detect and/or measure mRNA levels of a gene that is differentially expressed in a cancer cell. In some embodiments, the methods comprise: contacting a sample with a polynucleotide that corresponds to a differentially expressed gene described herein under conditions that allow hybridization; and detecting hybridization, if any. Detection of differential hybridization, when compared to a suitable control, is an indication of the presence in the sample of a polynucleotide that is differentially expressed in a cancer cell. Appropriate controls include, for example, a sample that is known not to contain a polynucleotide that is differentially expressed in a cancer cell. Conditions that allow hybridization are known in the art, and have been described in more detail above.

Detection can also be accomplished by any known method, including, but not limited to, in situ hybridization, PCR (polymerase chain reaction), RT-PCR (reverse transcription-PCR), and "Northern" or RNA blotting, arrays, microarrays, etc, or combinations of such techniques, using a suitably labeled polynucleotide. A variety of labels and labeling methods for polynucleotides are known in the art and can be used in the assay methods of the invention. Specific hybridization can be determined by comparison to appropriate controls.

Labeled nucleic acid probes may be used to detect expression of a gene corresponding to the provided polynucleotide, e.g. in a macroarray format, Northern blot, etc. The amount of hybridization can be quantitated to determine relative amounts of expression, for example under a particular condition. Probes are used for in situ hybridization to cells to detect expression. Probes can also be used in vivo for diagnostic detection of hybridizing sequences. Probes may be labeled with a radioactive isotope. Other types of detectable labels can be used such as chromophores, fluorophores, and enzymes.

Polynucleotide arrays provide a high throughput technique that can assay a large number of polynucleotides or polypeptides in a sample. This technology can be used as a tool to test for differential expression. A variety of methods of producing arrays, as well as variations of these methods, are known in the art and contemplated for use in the invention. For example, arrays can be created by spotting polynucleotide probes onto a substrate (e.g., glass, nitrocellulose, etc.) in a two-dimensional matrix or array having bound probes. The probes can be bound to the substrate by either covalent bonds or by non-specific interactions, such as hydrophobic interactions.

Characterization of Acute Myeloid Leukemia Stem Cells

In acute myeloid leukemias, characterization of cancer stem cells allows for the development of new treatments that are specifically targeted against this critical population of cells, particularly their ability to self-renew, resulting in more effective therapies.

In human acute myeloid leukemias it is shown herein that there is a subpopulation of tumorigenic cancer cells with both self-renewal and differentiation capacity. These tumorigenic cells are responsible for tumor maintenance, and also give rise to large numbers of abnormally differentiating progeny that are not tumorigenic, thus meeting the criteria of cancer stem cells. Tumorigenic potential is contained within a subpopulation of cancer cells differentially expressing the markers of the present invention.

In some embodiments of the invention, the number of AMLSC in a patient sample is determined relative to the total number of AML cancer cells, where a greater percentage of AMLSC is indicative of the potential for continued self-renewal of cells with the cancer phenotype. The quantitation of AMLSC in a patient sample may be compared to a reference population, e.g. a patient sample such as a blood sample, a remission patient sample, etc. In some embodiments, the quantitation of AMLSC is performed during the course of treatment, where the number of AML cancer cells and the percentage of such cells that are AMLSC are quantitated before, during and as follow-up to a course of therapy. Desirably, therapy targeted to cancer stem cells results in a decrease in the total number, and/or percentage of AMLSC in a patient sample.

In other embodiments of the invention, anti-cancer agents are targeted to AMLSC by specific binding to a marker or combination of markers of the present invention. In such embodiments, the anti-cancer agents include antibodies and antigen-binding derivatives thereof specific for a marker or combination of markers of the present invention, which are optionally conjugated to a cytotoxic moiety. Depletion of AMLSC is useful in the treatment of AML. Depletion achieves a reduction in circulating AMLSC by up to about 30%, or up to about 40%, or up to about 50%, or up to about 75% or more. Depletion can be achieved by using a an agent to deplete AMLSC either in vivo or ex vivo.

The AMLSC are identified by their phenotype with respect to particular markers, and/or by their functional phenotype. In some embodiments, the AMLSC are identified and/or isolated by binding to the cell with reagents specific for the markers of interest. The cells to be analyzed may be viable cells, or may be fixed or embedded cells.

In some embodiments, the reagents specific for the markers of interest are antibodies, which may be directly or indirectly labeled. Such antibodies will usually include antibodies specific for a marker or combination of markers of the present invention.

Treatment of Cancer

The invention further provides methods for reducing growth of cancer cells. The methods provide for decreasing the number of cancer cells bearing a specific marker or combination of markers, as provided herein, decreasing expression of a gene that is differentially expressed in a cancer cell, or decreasing the level of and/or decreasing an activity of a cancer-associated polypeptide. In general, the methods comprise contacting a cancer cell with a binding agent, e.g. an antibody or ligand specific for a marker or combination of markers provided herein.

"Reducing growth of cancer cells" includes, but is not limited to, reducing proliferation of cancer cells, and reducing the incidence of a non-cancerous cell becoming a cancerous cell. Whether a reduction in cancer cell growth has been achieved can be readily determined using any known assay, including, but not limited to, [$^3$H]-thymidine incorporation; counting cell number over a period of time; detecting and/or measuring a marker associated with AML, etc.

The present invention provides methods for treating cancer, generally comprising administering to an individual in need thereof a substance that reduces cancer cell growth, in an amount sufficient to reduce cancer cell growth and treat the cancer. Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

A substance, e.g. a chemotherapeutic drug that reduces cancer cell growth, can be targeted to a cancer cell. Thus, in some embodiments, the invention provides a method of delivering a drug to a cancer cell, comprising administering a drug-antibody complex to a subject, wherein the antibody is specific for a cancer-associated polypeptide, and the drug is one that reduces cancer cell growth, a variety of which are known in the art. Targeting can be accomplished by coupling (e.g., linking, directly or via a linker molecule, either covalently or non-covalently, so as to form a drug-antibody complex) a drug to an antibody specific for a cancer-associated polypeptide. Methods of coupling a drug to an antibody are well known in the art and need not be elaborated upon herein.

Staging and Diagnosis

Acute myeloid leukemias are staged by analysis of the presence of cancer stem cells. Staging is useful for prognosis and treatment. In one embodiment of the invention, a sample from an acute myeloid leukemia patient is stained with reagents specific for a marker or combination of markers of the present invention. The analysis of staining patterns provides the relative distribution of AMLSC, which distribution predicts the stage of leukemia. In some embodiments, the sample is analyzed by histochemistry, including immunohistochemistry, in situ hybridization, and the like, for the presence of $CD34^+CD38^-$ cells that express a marker or combination of markers of the present invention. The presence of such cells indicates the presence of AMLSC.

In one embodiment, the patient sample is compared to a control, or a standard test value. In another embodiment, the patient sample is compared to a pre-leukemia sample, or to one or more time points through the course of the disease.

Samples, including tissue sections, slides, etc. containing an acute myeloid leukemia tissue, are stained with reagents specific for markers that indicate the presence of cancer stem cells. Samples may be frozen, embedded, present in a tissue microarray, and the like. The reagents, e.g. antibodies, polynucleotide probes, etc. may be detectably labeled, or may be indirectly labeled in the staining procedure. The data provided herein demonstrate that the number and distribution of progenitor cells is diagnostic of the stage of the leukemia.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

Differential Cell Analysis

The presence of AMLSC in a patient sample can be indicative of the stage of the leukemia. In addition, detection of AMLSC can be used to monitor response to therapy and to aid in prognosis. The presence of AMLSC can be determined by quantitating the cells having the phenotype of the stem cell. In addition to cell surface phenotyping, it may be useful to quantitate the cells in a sample that have a "stem cell" character, which may be determined by functional criteria, such as the ability to self-renew, to give rise to tumors in vivo, e.g. in a xenograft model, and the like.

Clinical samples for use in the methods of the invention may be obtained from a variety of sources, particularly blood, although in some instances samples such as bone marrow, lymph, cerebrospinal fluid, synovial fluid, and the like may be used. Such samples can be separated by centrifugation, elutriation, density gradient separation, apheresis, affinity selection, panning, FACS, centrifugation with Hypaque, etc. prior to analysis, and usually a mononuclear fraction (PBMC) will be used. Once a sample is obtained, it can be used directly, frozen, or maintained in appropriate culture medium for short periods of time. Various media can be employed to maintain cells. The samples may be obtained by any convenient procedure, such as the drawing of blood, venipuncture, biopsy, or the like. Usually a sample will comprise at least about $10^2$ cells, more usually at least about $10^3$ cells, and preferable $10^4$, $10^5$ or more cells. Typically the samples will be from human patients, although animal models may find use, e.g. equine, bovine, porcine, canine, feline, rodent, e.g. mice, rats, hamster, primate, etc.

An appropriate solution may be used for dispersion or suspension of the cell sample. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Analysis of the cell staining will use conventional methods. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, peptide-MHC antigen and T cell receptor pairs may be used; peptide ligands and receptors; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then quantitated as to the expression of cell surface markers as previously described.

The comparison of a differential progenitor analysis obtained from a patient sample, and a reference differential progenitor analysis is accomplished by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

AMLSC Compositions

AMLSC may be separated from a complex mixture of cells by techniques that enrich for cells that differentially express a marker or combination of markers of the present invention. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for AMLSC are achieved in this manner. The subject population may be at or about 50% or more of the cell composition, and preferably be at or about 75% or more of the cell composition, and may be 90% or more. The desired cells are identified by their surface phenotype, by the ability to self-renew, ability to form tumors, etc. The enriched cell population may be used immediately, or may be frozen at liquid nitrogen temperatures and stored for long periods of time, being thawed and capable of being reused. The cells may be stored in 10% DMSO, 90% FCS medium. The population of cells enriched for AMLSC may be used in a variety of screening assays and cultures, as described below.

The enriched AMLSC population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. A wide variety of growth factors may be used in culturing the cells, e.g. LIF, steel factor (c-kit ligand), EGF, insulin, IGF, Flk-2 ligand, IL-11, IL-3, GM-CSF, erythropoietin, thrombopoietin, etc In addition to, or instead of growth factors, the subject cells may be grown in a co-culture with fibroblasts, stromal or other feeder layer cells. Stromal cells suitable for use in the growth of hematopoietic cells are known in the art. These include bone marrow stroma as used in "Whitlock-Witte" (Whitlock et al. [1985] *Annu Rev Immunol* 3:213-235) or "Dexter" culture conditions (Dexter et al. [1977] *J Exp Med* 145:1612-1616); and heterogeneous thymic stromal cells.

Screening Assays

AMLSC expressing a marker or combination of markers of the present invention are also useful for in vitro assays and screening to detect factors and chemotherapeutic agents that are active on cancer stem cells. Of particular interest are screening assays for agents that are active on human cells. A wide variety of assays may be used for this purpose, including immunoassays for protein binding; determination of cell growth, differentiation and functional activity; production of factors; and the like. In other embodiments, isolated polypeptides corresponding to a marker or combination of markers of the present invention are useful in drug screening assays.

In screening assays for biologically active agents, antiproliferative drugs, etc. the marker or AMLSC composition is contacted with the agent of interest, and the effect of the agent assessed by monitoring output parameters on cells, such as expression of markers, cell viability, and the like; or binding efficacy or effect on enzymatic or receptor activity for polypeptides. The cells may be freshly isolated, cultured, genetically altered, and the like. The cells may be environmentally induced variants of clonal cultures: e.g. split into independent cultures and grown under distinct conditions, for example with or without drugs; in the presence or absence of cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term "samples" also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51(3): 313-24, for examples.

Depletion of AMLSC

Depletion of AMLSC is useful in the treatment of AML. Depletion can be achieved by several methods. Depletion is defined as a reduction in the target population by up to about 30%, or up to about 40%, or up to about 50%, or up to about 75% or more. An effective depletion is usually determined by the sensitivity of the particular disease condition to the levels of the target population. Thus in the treatment of certain conditions a depletion of even about 20% could be beneficial.

A marker-specific agent that specifically depletes the targeted AMLSC is used to contact the patient blood in vitro or in vivo, wherein after the contacting step, there is a reduction in the number of viable AMLSC in the targeted population. An exemplary agent for such purposes is an antibody that specifically binds to a marker or combination of markers of the present invention on the surface of the targeted AMLSC. An effective dose of antibodies for such a purpose is sufficient to decrease the targeted population to the desired level, for example as described above. Antibodies for such purposes may have low antigenicity in humans or may be humanized antibodies.

In one embodiment of the invention, antibodies for depleting target population are added to patient blood in vivo. In another embodiment, the antibodies are added to the patient blood ex vivo. Beads coated with the antibody of interest can be added to the blood, target cells bound to these beads can then be removed from the blood using procedures common in the art. In one embodiment the beads are magnetic and are removed using a magnet. Alternatively, when the antibody is biotinylated, it is also possible to indirectly immobilize the antibody onto a solid phase which has adsorbed avidin, streptavidin, or the like. The solid phase, usually agarose or sepharose beads are separated from the blood by brief centrifugation. Multiple methods for tagging antibodies and removing such antibodies and any cells bound to the antibodies are routine in the art. Once the desired degree of depletion has been achieved, the blood is returned to the patient. Depletion of target cells ex vivo decreases the side effects such as infusion reactions associated with the intravenous administration. An additional advantage is that the repertoire of available antibodies is expanded significantly as this procedure does not have to be limited to antibodies with low antigenicity in humans or humanized antibodies.

Kits may be provided, where the kit will comprise staining reagents that are sufficient to differentially identify the AMLSC described herein. A combination of interest may include one or more reagents specific for a marker or combination of markers of the present invention, and may further include antibodies specific for CD96, CD34, and CD38. The staining reagents are preferably antibodies, and may be detectably labeled. Kits may also include tubes, buffers, etc., and instructions for use.

Each publication cited in this specification is hereby incorporated by reference in its entirety for all purposes.

It is to be understood that this invention is not limited to the particular methodology, protocols, cell lines, animal species or genera, and reagents described, as such may vary.

EXPERIMENTAL

Example 1

Identification of a Hierarchy of Multipotent Hematopoietic Progenitors in Human Cord Blood Mouse hematopoiesis is initiated by long-term hematopoietic stem cells (HSC) that differentiate into a series of multipotent progenitors that exhibit progressively diminished self-renewal ability. In human hematopoiesis, populations enriched for HSC activity have been identified, as have downstream lineage-committed progenitors, but multipotent progenitor activity has not been uniquely isolated. Previous reports indicate that human HSC are enriched in Lin−CD34+CD38− cord blood and bone marrow and express CD90. We demonstrate that the Lin−CD34+CD38− fraction of cord blood and bone marrow can be subdivided into three subpopulations: CD90+CD45RA−, CD90−CD45RA−, and CD90−CD45RA+. Utilizing in vivo transplantation studies and complementary in vitro assays, we demonstrate that the Lin−CD34+CD38−CD90+CD45RA− cord blood fraction contains HSC, and isolate this activity to as few as 10 purified cells. Furthermore, we report the first prospective isolation of a population of candidate human multipotent progenitors, Lin−CD34+CD38−CD90−CD45RA− cord blood.

Identification of CD90/CD45RA Subpopulations of Lin−CD34+CD38− Human Bone Marrow and Cord Blood. Data from multiple investigators indicate that human HSC activity resides in the CD90+ fraction of Lin−CD34+CD38−/lo cells. Using the marker CD45RA, three subpopulations of Lin−CD34+CD38− bone marrow and cord blood were identified: (1) CD90+CD45RA−, (2) CD90−CD45RA−, and (3) CD90−CD45RA+(FIG. 1). In the bone marrow these population comprised 30.3±18.9% (CD90+CD45RA−), 37.7±14.1% (CD90−CD45RA−), and 24.7±11.8% (CD90−CD45RA) of Lin−CD34+CD38− cells (n=10). In cord blood, these fractions constituted 25.2±10.3% (CD90+CD45RA−), 49.8±11.4% (CD90−CD45RA−), and 18.4±8.4% (CD90−CD45RA+) of Lin−CD34+CD38− cells (n=22). All three subpopulations were isolated to >95% purity from cord blood and bone marrow by FACS.

Figure 2:
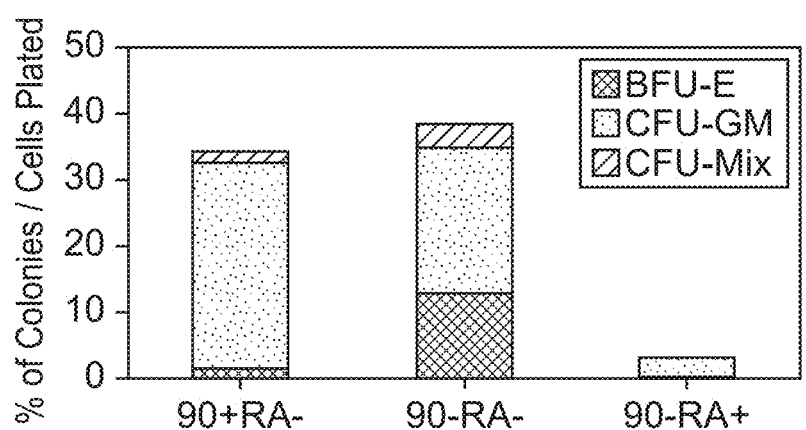
FIG. 2: In Vitro Evaluation of the CD90/CD45RA Subpopulations of Lin−CD34+CD38− Cord Blood Reveals a Developmental Hierarchy. A. Methylcellulose colony formation. Single cells from each CD90/CD45RA subpopulation were sorted into individual wells of a 96 well plate containing complete methylcellulose capable of supporting growth of all types of myeloid colonies. After 12-14 days, colonies were scored based on morphology. The percent of each type of colony out of the total cells plated is indicated. Data presented is cumulative from 3 experiments of 60 cells each, for a total of 180 cells per subpopulation. B. Methylcellulose colony replating. All colonies derived from individual cells were harvested, dissociated, and replated in complete methylcellulose. 12-14 days later, the formation of new colonies was scored based on morphology. 42 out of 62 (70%) of CD90+CD45RA−, 23 out of 70 (33%) of CD90−CD45RA−, and 0 out of 6 (0%) of CD90−CD45RA+ colonies formed new colonies upon replating. The difference in replating efficiency between CD90+CD45RA− and CD90−CD45RA− was statistically significant (p=0.003). Data presented is the average of 3 independent experiments with the indicated SEM. C. In vitro proliferation. 20 cells of each CD90/CD45RA subpopulation were clone sorted into individual wells of a 96 well plate containing serum-free media supplemented with human LDL and cytokines. After 2 weeks in culture, cells were harvested and live cells counted by trypan blue exclusion. The difference between the CD90+CD45RA− and the CD90−CD45RA− subpopulations was statistically significant (p=0.007). Data is representative of 3 independent experiments. D. In vitro hierarchical relationships among CD90/CD45RA subpopulations. CD90/CD45RA subpopulations were sorted in bulk into serum-free media supplemented with human LDL and cytokines. Cells were cultured for four days and then re-analyzed by flow cytometry. All plots shown are gated on Lin−CD34+CD38− cells; the left panels show the cell input; the right panels show the cells after four days in culture. Data shown is representative of 3 independent experiments.
Figure 2:
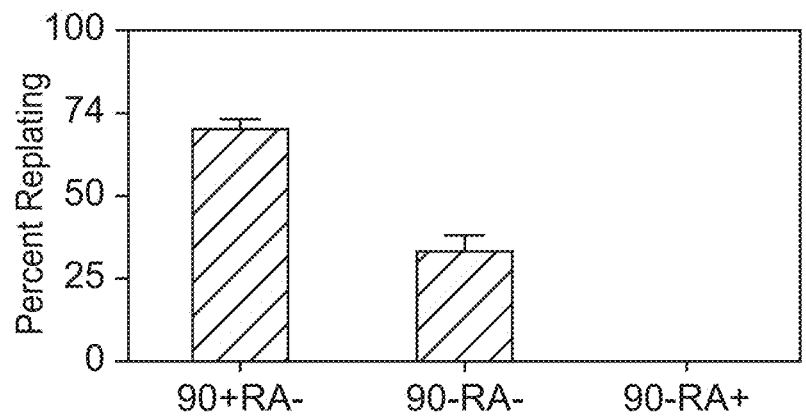
Figure 2:
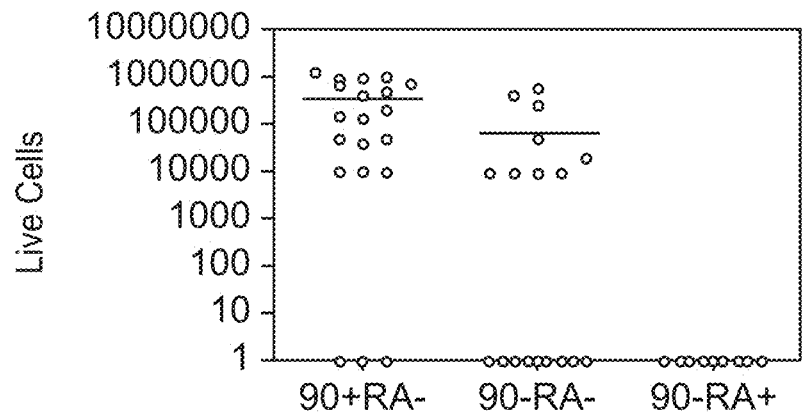
Figure 2:
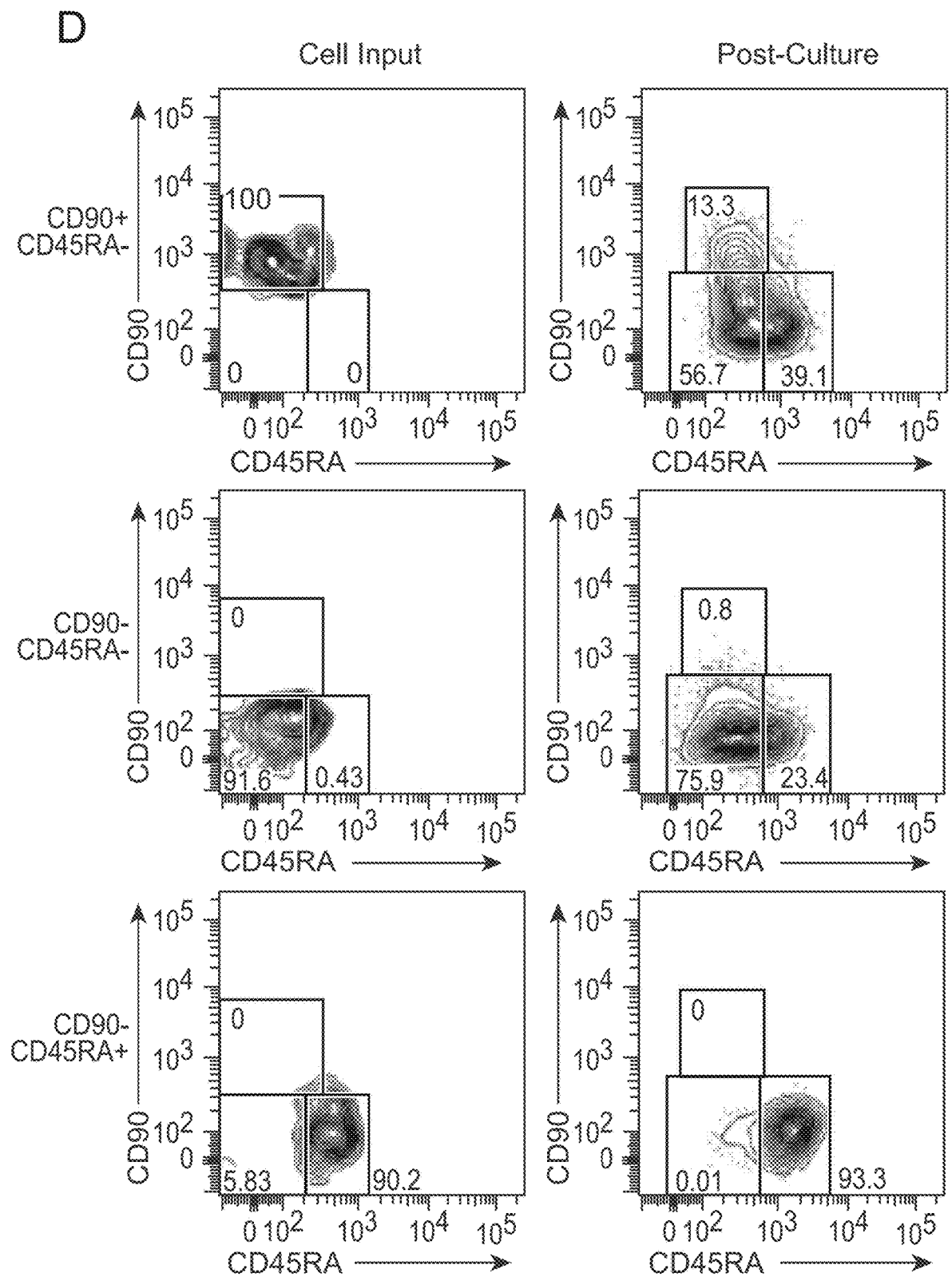

Methylcellulose Colony Formation and Replating of CD90/CD45RA Subpopulations. In order to assess the lineage potential of the CD90/CD45RA subpopulations, each was assayed for in vitro colony formation in methylcellulose. Single cells of each population were sorted into individual wells of a 96-well plate containing complete methylcellulose. In all cases, only a single colony was detected. CD90+CD45RA− cells formed all types of myeloid colonies, as did CD90−CD45RA− cells (FIG. 2A). No differences were detected in plating efficiency or colony subtype distribution between these two subpopulations; however, the CD90+CD45RA− colonies were generally much larger and faster growing. CD90−CD45RA+ cells formed very few colonies, suggesting that these cells possess limited myeloid differentiation potential.

All colonies derived from individual cells were then harvested, dissociated, and plated in complete methylcellulose in order to determine replating efficiency, an in vitro surrogate for self-renewal (FIG. 2B). 70% of colonies derived from CD90+CD45RA− cells were able to form new colonies (in most cases, hundreds) upon replating. 33% of colonies derived from CD90−CD45RA− cells were able to form new colonies (in most cases, fewer than 50). None of the colonies derived from CD90+CD45RA− cells were able to form new colonies; however, very few colonies formed in the first plating (n=6). Thus, the CD90−CD45RA− subpopulation is able to form all myeloid cells, but has reduced capacity for self-renewal compared to the CD90+CD45RA− subpopulation, which is presumed to contain HSC.

In Vitro Proliferation and Differentiation Identifies a Hierarchy Among the CD90/CD45RA Subpopulations. The CD90/CD45RA subpopulations were also assayed for in vitro proliferation in serum-free liquid culture. Single cells of each population were sorted into individual wells of a 96-well plate containing serum-free media supplemented with Flt-3 ligand, SCF, TPO, IL-3, and IL-6 and cultured for 2 weeks. At the end of the culture period, live cells were counted. CD90+CD45RA− cells proliferated extensively with a mean recovery of 345,000 cells; CD90−CD45RA− cells proliferated to a lesser degree with a mean recovery of 67,500 cells; CD90−CD45RA+ cells proliferated poorly with few live cells recovered (FIG. 2C). These results support the observed differences in methylcellulose colony size and suggest that the CD90− subpopulations are less primitive than the CD90+ subpopulation presumed to contain HSC.

In order to examine the potential hierarchical relationships between the CD90/CD45RA subpopulations within the Lin−CD34+CD38− fraction, each population was sorted in bulk into serum-free media supplemented with cytokines as described above. After four days in culture, the cells were re-analyzed for expression of CD90 and CD45RA (FIG. 2D). While CD90+CD45RA− cells gave rise to all three subpopulations, CD90−CD45RA− cells gave rise to both CD90− subpopulations, but not CD90+ cells. CD90−CD45RA+ cells gave rise principally to itself only. Together, these data establish an in vitro differentiation hierarchy in which CD90+CD45RA− cells give rise to CD90−CD45RA− cells, which in turn give rise to CD90−CD45RA+ cells.

Figure 3:
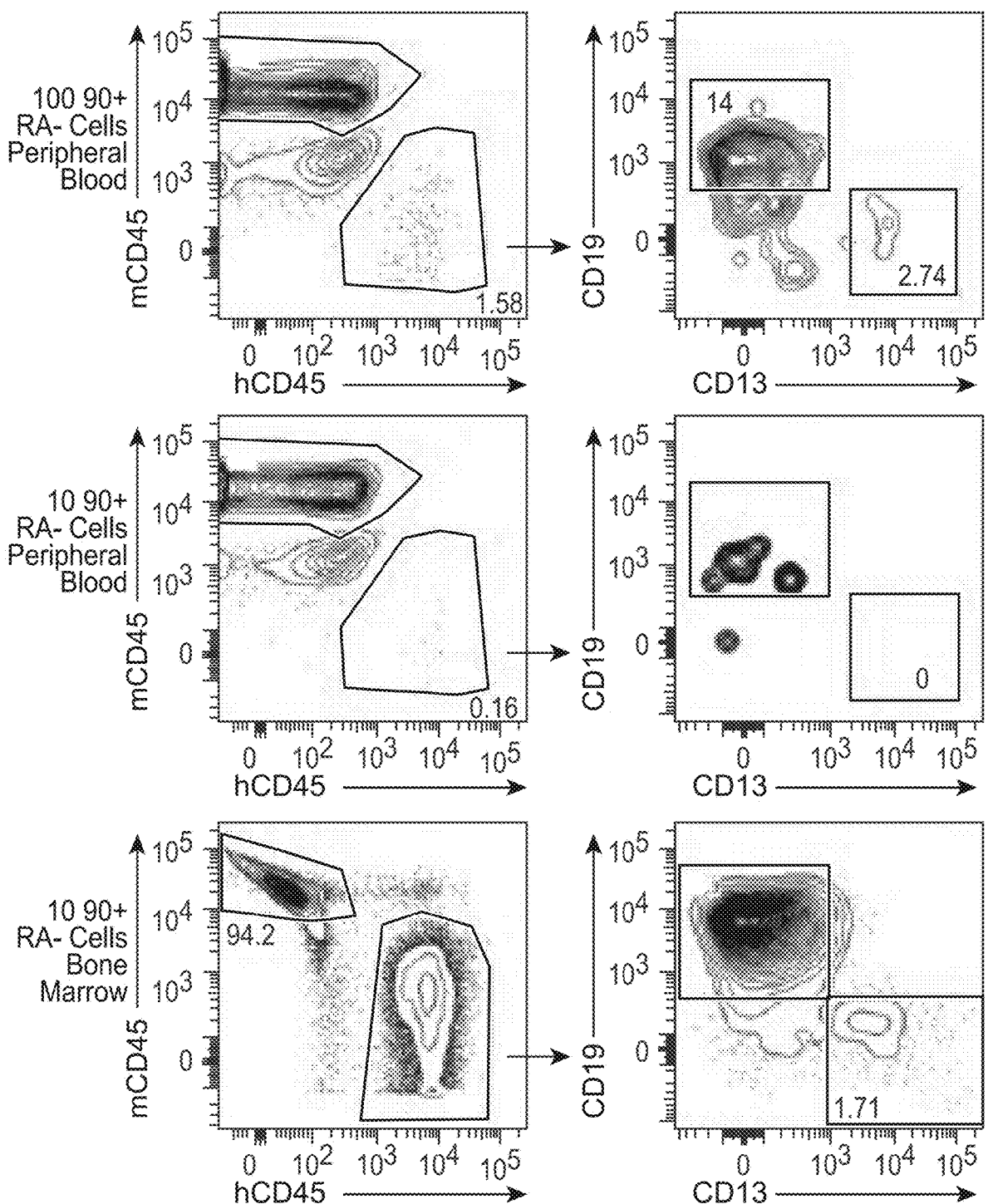
FIG. 3: Long-Term In Vivo Multipotent Human Hematopoiesis with Transplantation of as few as 10 Lin−CD34+CD38−CD90+CD45RA− Cord Blood Cells. A. In vivo engraftment of 100 or 10 CD90+CD45RA− cells. 100 or 10 FACS-purified CD90+CD45RA− cells were transplanted into NOG newborn mice as described. 12 weeks later peripheral blood and/or bone marrow was harvested and analyzed by flow cytometry for the presence of human CD45+ hematopoietic cells, myeloid cells (hCD45+CD13+), and B lymphoid cells (hCD45+CD19+) cells. The right plots are gated on human CD45+ cells. B. Wright-Giemsa stained cytosine preparations from CD90+CD45RA− engrafted mice. Human CD45+ cells were purified by FACS from peripheral blood (panels 1-3) or bone marrow (panel 4) of mice engrafted with CD90+CD45RA− cells. In the peripheral blood, (1) lymphocytes, (2) neutrophils, and (3) monocytes were detected; in the bone marrow (4) lymphocytes and maturing myeloid cells were detected. (100×)
Figure 3:
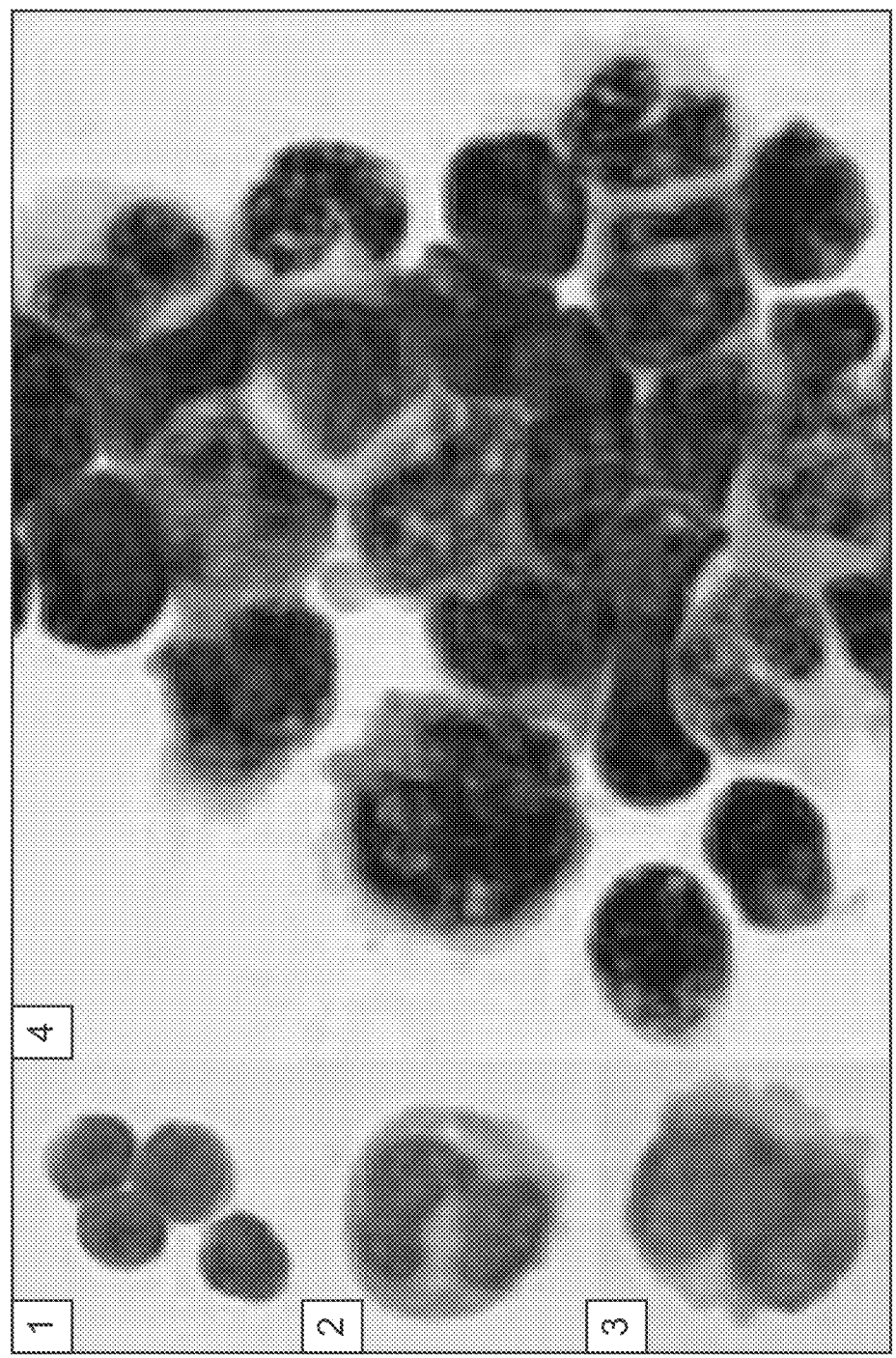

Long-Term In Vivo Multipotent Human Hematopoiesis with Transplantation of as few as 10 Lin−CD34+CD38−CD90+CD45RA− Cord Blood Cells. Newborn NOD/SCID/IL-2$^\gamma$-null (NOG) mice were used in xenotransplantation assays to determine the differentiation potential and self-renewal ability of the CD90/CD45RA subpopulations. Transplantation of 100 purified CD90+CD45RA− cells resulted in circulating human CD45+ hematopoietic cells at 12 weeks, including both CD13+ myeloid cells, and CD19+ B cells, but not CD3+ T cells (FIG. 3A). Several of these mice were followed beyond 12 weeks (maximum 30 weeks), and all continued to have detectable human myeloid cells at similar levels in the peripheral blood (data not shown), indicating continued human engraftment. In order to isolate this activity to as few cells as possible, 10 purified CD90+CD45RA− cells were transplanted. At 12 weeks, few circulating human CD45+ cells were detected, and no CD13+ myeloid cells were present (FIG. 3A); however, analysis of the bone marrow showed significant human engraftment with both myeloid and lymphoid cells (FIG. 3A). Successful long-term human engraftment was observed in 3 out of 10 mice transplanted with 10 CD90+CD45RA− cells, with the 3 successful engraftments coming from independent cord blood samples.

Both CD13+ myeloid cells and CD19+ B cells were detected in the blood and bone marrow of engrafted mice, indicating that CD90+CD45RA− cells possess lymphoid and myeloid potential, and are likely multipotent. Analysis of the spleen from engrafted mice identified human CD45+ CD3+ T cells, and staining of the bone marrow with glycophorin-A and CD61/41 identified human erythroid cells and platelets. To confirm this flow cytometry-derived lineage analysis, human CD45+ cells from both peripheral blood and bone marrow were FACS-purified and cytospin preparations were stained with Wright-Giemsa. These stains confirmed the presence of mature human lymphocytes, neutrophils, and monocytes in the peripheral blood (FIG. 3B, panels 1-3). In the bone marrow, both lymphocytes and maturing myeloid cells were readily detected (FIG. 3B, panel 4). Collectively, these data indicate that Lin−CD34+ CD38−CD90+CD45RA− cord blood cells are capable of establishing long-term in vivo multipotent human hematopoiesis and that this activity can be isolated to as few as 10 cells.

Figure 4:
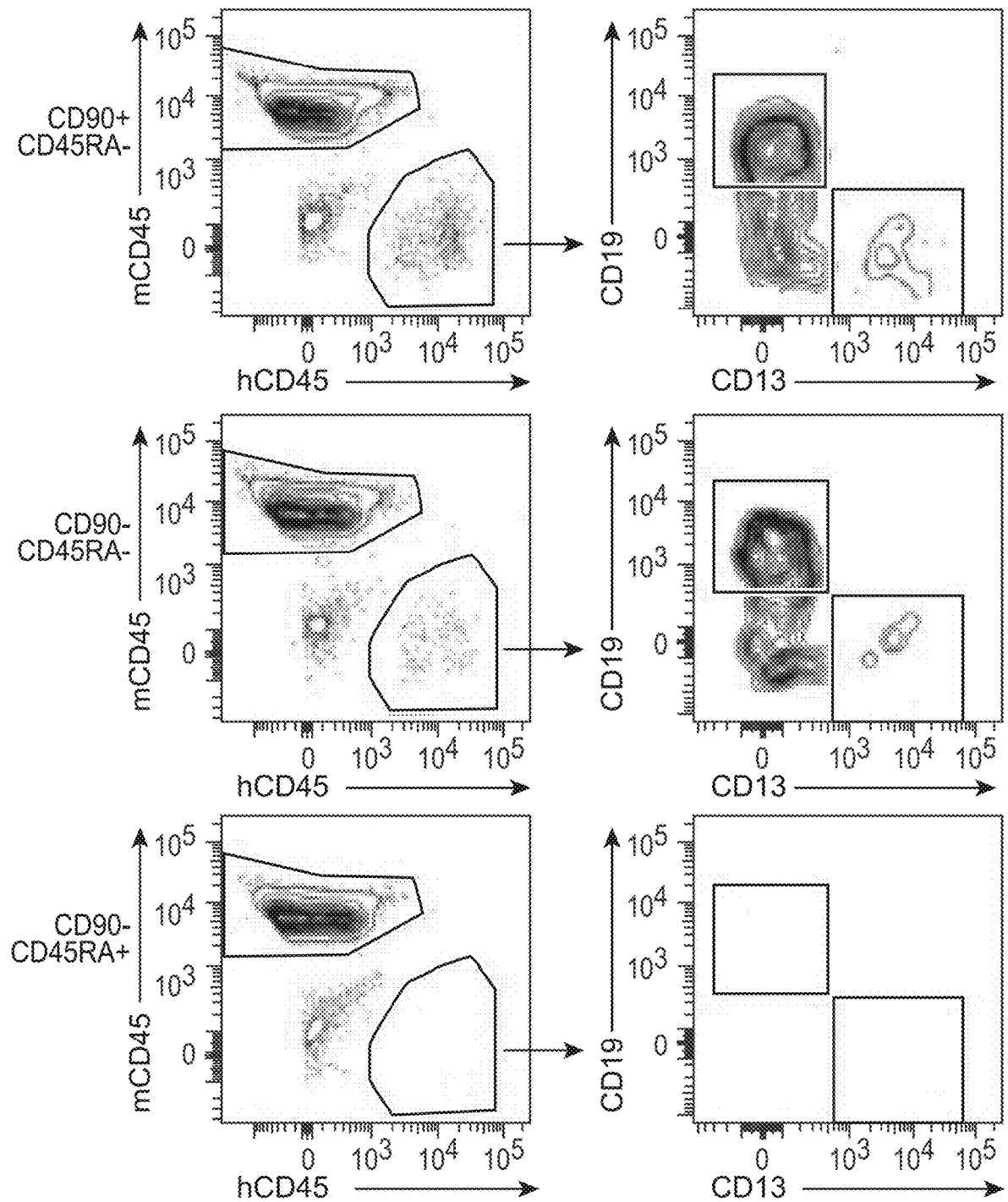
FIG. 4: Human Lymphoid and Myeloid Cells Reconstitute the Peripheral Blood of CD90/CD45RA Transplanted Mice. A. Peripheral blood engraftment and lineage analysis of CD90/CD45RA transplanted mice. 500 FACS-purified cells of each CD90/CD45RA subpopulation: CD90+CD45RA− (top panels), CD90−CD45RA− (middle panels), and CD90−CD45RA+(bottom panels), were transplanted into NOG newborn mice as described. 12 weeks later peripheral blood was harvested and analyzed by flow cytometry for the presence of human CD45+ hematopoietic cells, myeloid cells (hCD45+CD13+), and B lymphoid cells (hCD45+CD19+) cells. The right plots are gated on human CD45+ cells. B. Summary of long-term (>12 weeks) peripheral blood engraftment of CD90/CD45RA subpopulations. C. Peripheral blood engraftment per 100 transplanted cells. The percent human chimerism (left) and percent human myeloid cells (right) per 100 transplanted cells is indicated for each engrafted mouse. Each circle or triangle represents an individual mouse and the bar indicates the average. On average, CD90+CD45RA− mice developed 7 fold more human chimerism than CD90−CD45RA− mice, and this difference was statistically significant (p=0.02). The 7 fold difference in percent human myeloid cells approached, but did not achieve statistical significance (p=0.08).
Figure 4:
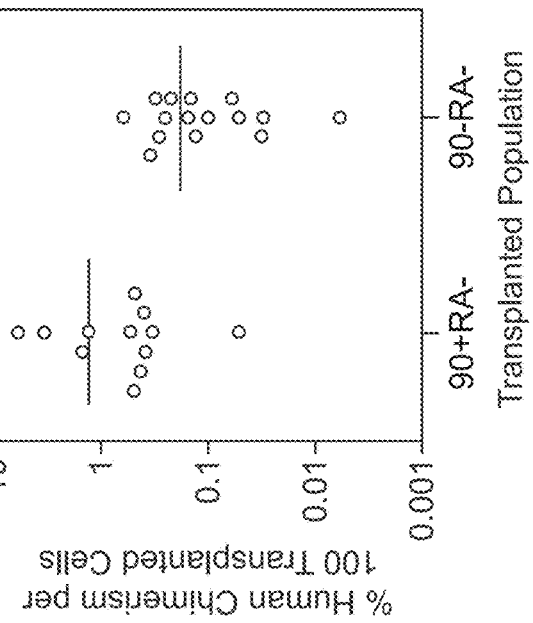

Long-Term In Vivo Multipotent Human Hematopoiesis Requires Transplantation of More CD90−CD45RA− Cells Than CD90+CD45RA− Cells. All three CD90/CD45RA subpopulations of cord blood were purified by FACS and transplanted into NOG mice. Transplantation of both the CD90+CD45RA− and the CD90−CD45RA− subpopulations resulted in detectable human myeloid and B lymphoid cells in the peripheral blood 12 weeks after transplantation (FIG. 4A). No human cells were detected in the peripheral blood of mice transplanted with the CD90−CD45RA+ subpopulation, even at time points as early as 4 weeks after transplantation (FIG. 4A). Multiple transplantation experiments were conducted with independent cord blood samples resulting in transplantation of between 100 and 4440 cells of each population (FIG. 4B). The cumulative data from these experiments showed that 12 of 13 mice (92%) transplanted with CD90+CD45RA− cells, and 15 of 17 mice (88%) transplanted with CD90−CD45RA− cells contained human CD45+ cells in the peripheral blood at least 12 weeks after transplantation (FIG. 4B). In the engrafted mice, the average human CD45+ chimerism was 3.7% for the CD90+ CD45RA− transplants compared to 4.0% for the CD90− CD45RA− transplants; the percentage of myeloid cells among human CD45+ cells was 6.7% for the CD90+ CD45RA− transplants compared to 7.1% for the CD90− CD45RA− transplants (FIG. 4B). Because different cell numbers were used in each of these transplantation experiments, the engraftment per 100 transplanted cells was determined. The CD90+CD45RA− engrafted mice averaged 7 fold greater human chimerism and 7 fold greater human myeloid cells than the CD90−CD45RA− engrafted mice (FIG. 4C). The difference in human chimerism was statistically significant with p=0.02, while the difference in human myeloid cells approached statistical significance with p=0.08.

Figure 5:
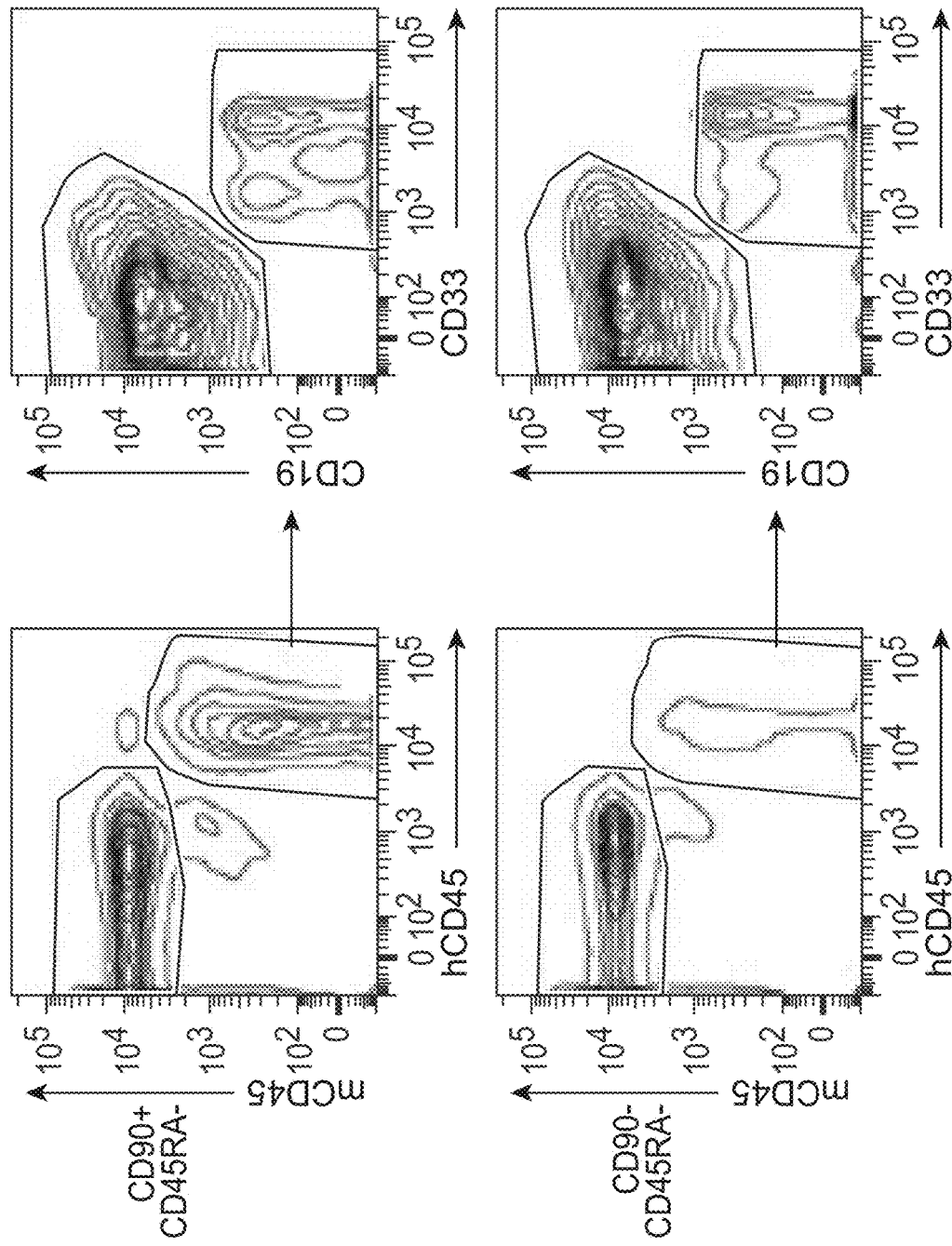
FIG. 5: Human Lymphoid and Myeloid Cells Reconstitute the Bone Marrow of CD90+CD45RA− Transplanted Mice More Efficiently than CD90−CD45RA− Transplanted Mice. A. Bone marrow engraftment and lineage analysis of CD90/CD45RA transplanted mice. 500 FACS-purified CD90+CD45RA− cells (top panels) and CD90−CD45RA− cells (bottom panels) were transplanted into NOG newborn mice as described. 12 weeks later bone marrow was analyzed by flow cytometry for the presence of human CD45+ hematopoietic cells, myeloid cells (hCD45+CD33+), and B lymphoid cells (hCD45+CD19+) cells. The right plots are gated on human CD45+ cells. B. Summary of long-term (>12 weeks) bone marrow engraftment of CD90/CD45RA subpopulations. C. Bone marrow engraftment per 100 transplanted cells. The percent human chimerism (left) and percent human myeloid cells (right) per 100 transplanted cells is indicated for each engrafted mouse. Each circle or triangle represents an individual mouse and the bar indicates the average. On average, CD90+CD45RA− mice developed 9 fold more human chimerism than CD90−CD45RA− mice, and this difference was statistically significant (p=0.001). The 9 fold difference in percent human myeloid cells approached, but did not achieve statistical significance (p=0.07). D. Summary of long-term (>11 weeks) bone marrow engraftment of limiting numbers (<100 cells) of CD90/CD45RA subpopulations. 50 or 70 double FACS-purified CD90+CD45RA− or CD90−CD45RA− cells were transplanted into NOG newborn mice as described. At least 11 weeks later bone marrow was analyzed by flow cytometry for the presence of human CD45+ hematopoietic cells, myeloid cells (hCD45+CD33+), B cells (hCD45+CD19+) cells, and T cells (hCD45+CD3+). In 1 out of 5 mice transplanted with CD90−CD45RA− cells, a small population of T cells (0.2%) was detected in the bone marrow, in the absence of myeloid and B cells. The difference in successful engraftment was statistically significant (p=0.008).
Figure 5:
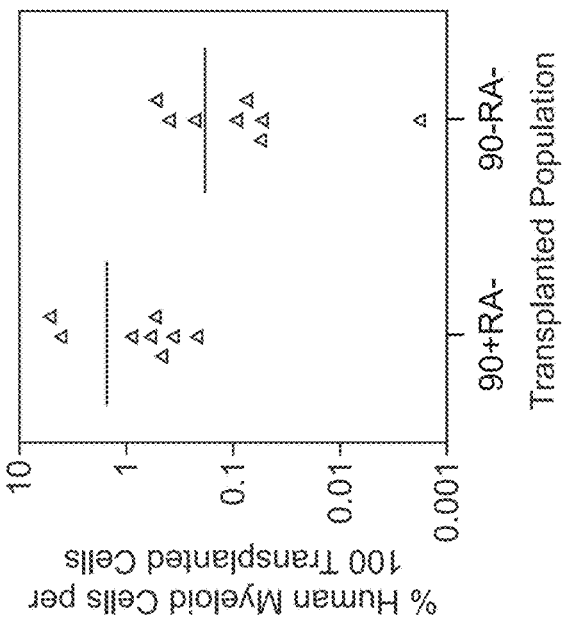
Figure 5:
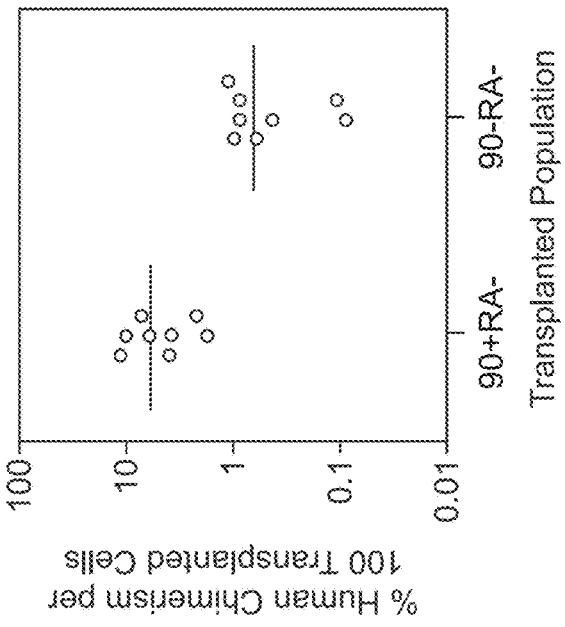

Analysis of the bone marrow of transplanted mice revealed human myeloid and B cells 12 weeks after transplantation of CD90+CD45RA− and CD90−CD45RA− cells (FIG. 5A). No human cells were detected in the bone marrow of mice transplanted with the CD90−CD45RA+ population. Cumulative data showed that 8 of 8 mice (100%) transplanted with CD90+CD45RA− cells, and 8 of 9 mice (89%) transplanted with CD90−CD45RA− cells contained human CD45+ cells in the bone marrow at least 12 weeks after transplantation (FIG. 5B). In the engrafted mice, the average human chimerism was 19.9% for the CD90+ CD45RA− transplants compared to 4.4% for the CD90− CD45RA− transplants; the percent myeloid of total human CD45+ cells was 24.3% for the CD90+CD45RA− transplants compared to 26.6% for the CD90−CD45RA− transplants (FIG. 5B). In order to normalize for cell number, bone marrow engraftment per 100 transplanted cells was determined. The CD90+CD45RA− engrafted mice averaged 9 fold greater human chimerism and 9 fold greater human myeloid cells than the CD90−CD45RA− engrafted mice (FIG. 5C). The difference in human chimerism was statistically significant with p=0.001, while the difference in human myeloid cells approached statistical significance with p=0.07.

Analysis of the spleens of CD90+CD45RA− and CD90− CD45RA− transplanted mice identified human CD45+ cells consisting of rare myeloid cells, numerous B cells, and occasional T cells. No human cells were detected in the spleens of mice transplanted with CD90−CD45RA+ cells. Significant numbers of T cells were detected in only a subset of mice transplanted with either engrafting population (Supplementary FIG. 2). Determining splenic engraftment per 100 transplanted cells revealed that CD90+CD45RA− engrafted mice averaged 7 fold greater human chimerism than the CD90−CD45RA− engrafted mice, and this difference was statistically significant; however, no statistically significant difference was detected in the T cell percentage. Finally, bone marrow from mice engrafted with CD90− CD45RA− cells was found to contain GPA-positive human erythroid cells and CD61/CD41-positive human platelets (data not shown), indicating that these cells are multipotent.

To investigate the minimum number of cells required for successful engraftment, 50 or 70 CD90−CD45RA− or CD90+CD45RA− cells were double FACS-purified from 2 independent cord blood samples and transplanted into NOG mice. At least 11 weeks later, bone marrow was analyzed for human engraftment. All mice (n=4) transplanted with CD90+CD45RA− cells contained human myeloid and B cells, while no mice (n=5) transplanted with CD90− CD45RA− cells did (FIG. 5D). This difference was statistically significant with p=0.008. One of the CD90− CD45RA− transplanted mice did contain a small population (0.2%) of human T cells, indicating that it must have engrafted at an early time point. To directly investigate early engraftment, 50 double FACS-purified cells were transplanted into NOG newborn mice. 4 weeks later, bone marrow of all transplanted mice, both CD90+CD45RA− (n=2) and CD90−CD45RA− (n=2), contained human myeloid and B cells.

In summary, both the CD90+CD45RA− and CD90− CD45RA− subpopulations are capable of establishing long-term in vivo multipotent human hematopoiesis, with similar percentages of myeloid and lymphoid cell production. However, the CD90−CD45RA− cells have a lower engraftment capacity as they require transplantation of more cells for long-term engraftment and generate fewer human cells per cell-equivalent transplant.

Figure 6:
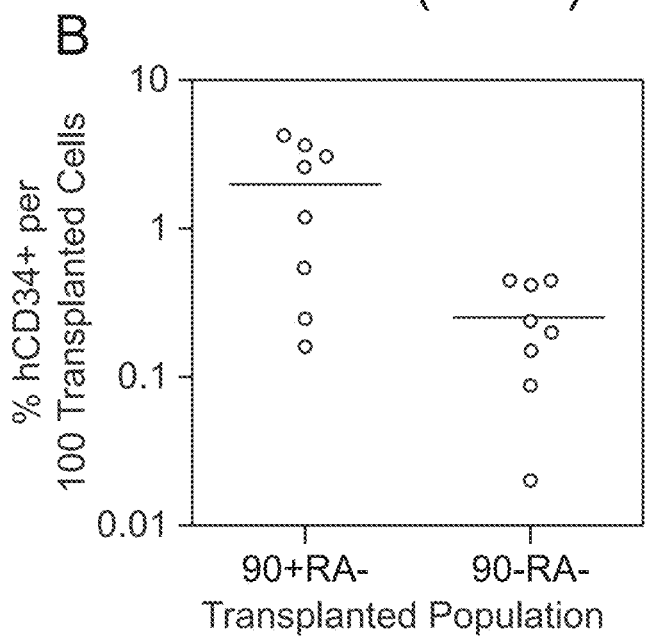
FIG. 6: In Vivo Analysis of Human CD34+ Cells Identifies a Hierarchy Among the CD90/CD45RA Subpopulations. A. Summary of long-term (>12 weeks) human CD34+ bone marrow engraftment of CD90/CD45RA subpopulations. B. Bone marrow human CD34+ engraftment per 100 transplanted cells. The percentage of human CD34+ cells in total bone marrow per 100 transplanted cells is indicated for each engrafted mouse. Each circle represents an individual mouse and the bar indicates the average. On average, CD90+CD45RA− mice contained 8 fold more human CD34+ cells than CD90−CD45RA− mice, and this difference was statistically significant (p=0.01). C. Analysis of CD90/CD45RA expression on Lin−CD34+CD38− bone marrow cells in CD90/CD45RA transplanted mice. 500 FACS-purified CD90+CD45RA− cells (top panels) and CD90−CD45RA− cells (bottom panels) were transplanted into NOG newborn mice as described. 12 weeks later bone marrow was analyzed by flow cytometry for the expression of lineage markers, CD34, CD38, CD90, and CD45RA. The left plots are gated on Lin−CD34+ cells, and the right plots are gated on Lin−CD34+CD38− cells. D. CD90/CD45RA subpopulations within engrafted bone marrow. The percentage of CD90+CD45RA− (left), CD90−CD45RA− (middle), and CD90−CD45RA+(right) cells out of Lin−CD34+ CD38− bone marrow cells from mice engrafted with CD90+ CD45RA− and CD90−CD45RA− cells is indicated. Each circle, triangle, or square represents an individual mouse. Only mice with greater than 10 Lin−CD34+CD38− cells were included (n=7 transplanted with CD90+CD45RA− cells and n=4 transplanted with CD90−CD45RA− cells).
Figure 6:
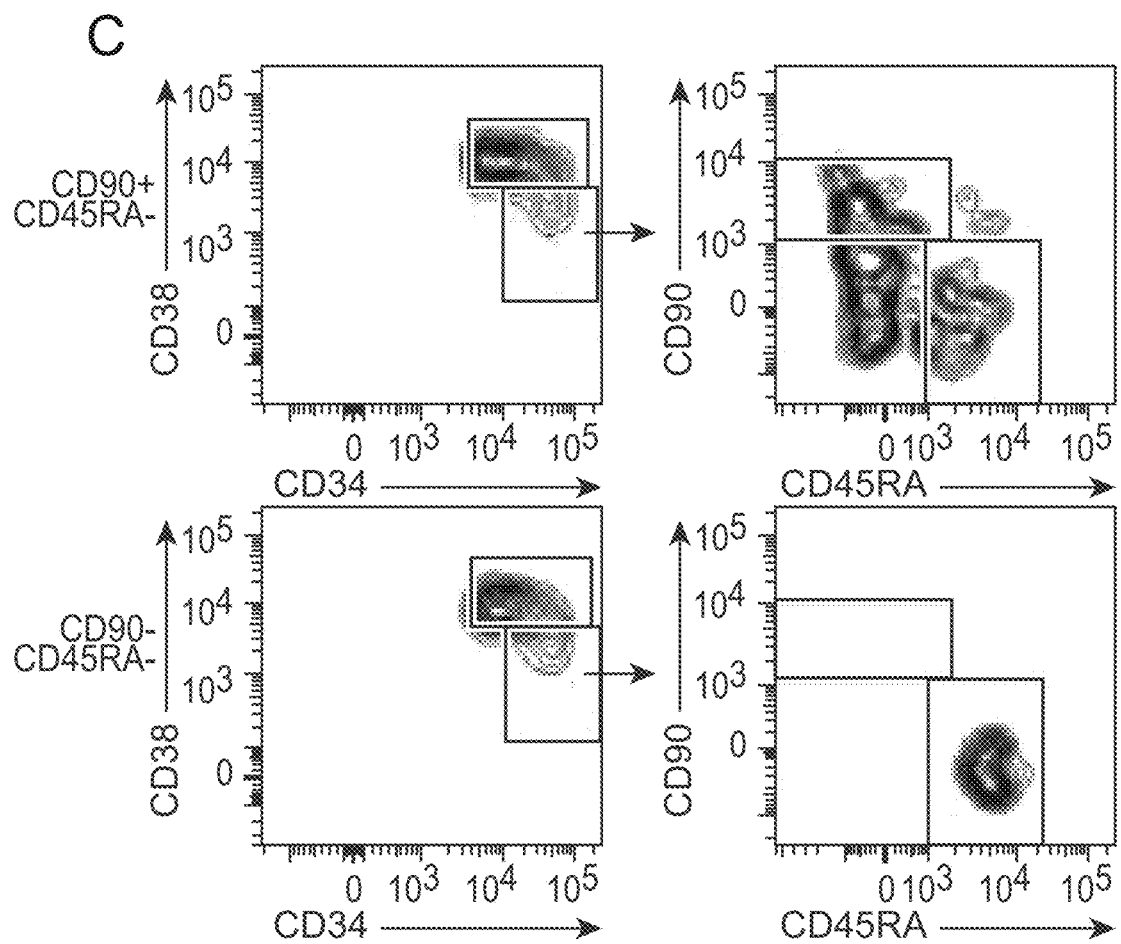
Figure 6:
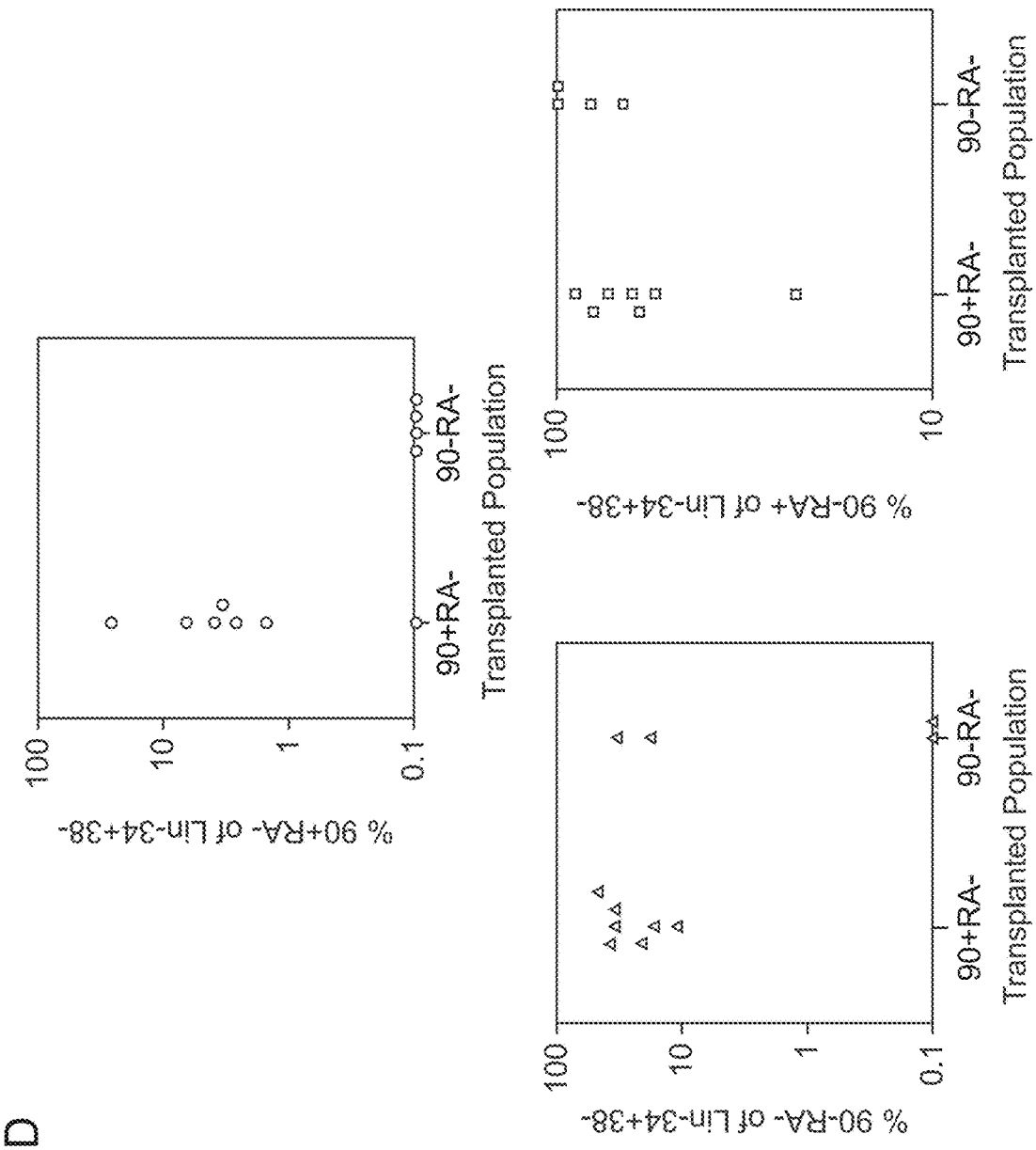

In Vivo Analysis of Human CD34+ Cells Identifies a Hierarchy Among the CD90/CD45RA Subpopulations. In order to assess the hierarchical relationships among the CD90/CD45RA subpopulations in vivo, human CD34+ progenitor cells from the bone marrows of engrafted mice were analyzed 12 weeks after transplantation. In mice transplanted with CD90+CD45RA− cells the bone marrow contained, on average, 6.4% human CD34+ cells compared to 1.3% human CD34+ cells in mice transplanted with CD90−CD45RA− cells (FIG. 6A). CD34+ engraftment per 100 transplanted cells averaged 8 fold greater in CD90+CD45RA− engrafted mice than CD90−CD45RA− engrafted mice, and this difference was statistically significant (FIG. 6B). This 8 fold statistically significant difference was also present when comparing the percentage of Lin−CD34+ cells in total bone marrow (data not shown). Within the engrafted Lin−CD34+ fraction, there were no differences between CD90+CD45RA− and CD90−CD45RA− engrafted mice with respect to the percentages of CD34+CD38+ or CD34+CD38− cells (FIG. 6A). Thus, CD90−CD45RA− cells appear to be able to generate progenitor cells in similar proportions to CD90+CD45RA− cells, but are less efficient in doing so in vivo.

Human Lin−CD34+CD38− cells in the bone marrow of engrafted mice were also analyzed for the expression of CD90 and CD45RA. All three CD90/CD45RA subpopulations were detected in the bone marrow of mice transplanted with CD90+CD45RA− cells; however, only the two CD90− subpopulations were detected in mice transplanted with CD90−CD45RA− cells (FIG. 6C, D). In some mice transplanted with CD90−CD45RA− cells, only CD90−CD45RA+ cells were detected. Together, these data establish an in vivo differentiation hierarchy among Lin−CD34+ CD38− cord blood cells proceeding from CD90+CD45RA− to CD90−CD45RA− to CD90−CD45RA+ cells.

Figure 7:
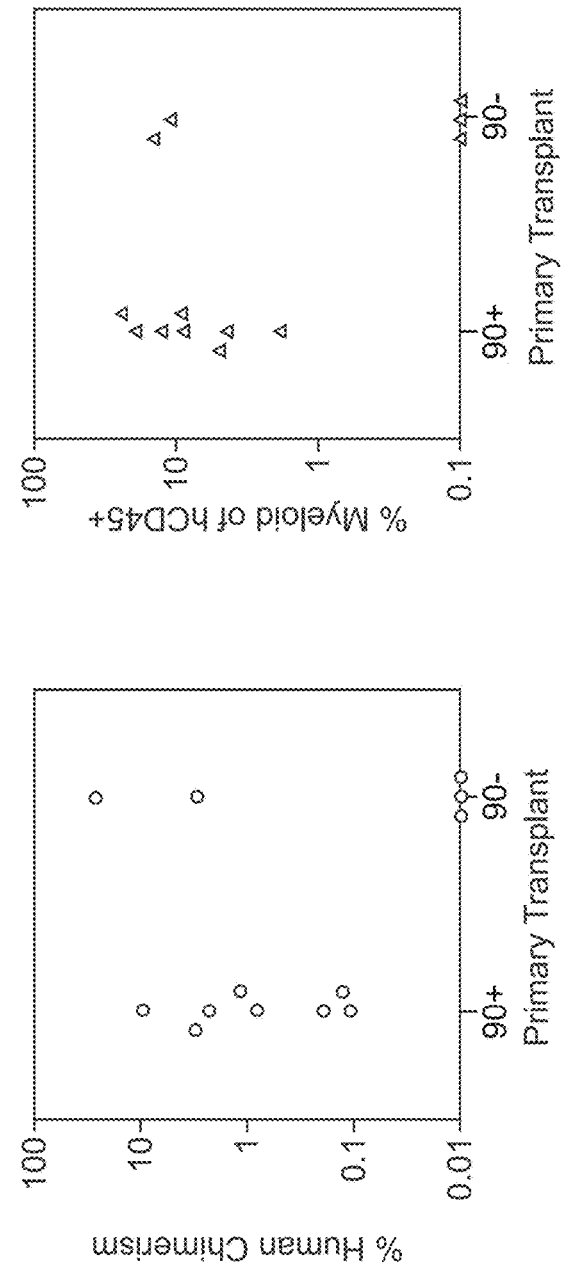
FIG. 7: Enrichment of Secondary Transplant Ability in the CD90+CD45RA Subpopulation. A. Summary of long-term (>10 weeks) bone marrow engraftment in secondary transplants from mice engrafted with either CD90+ or CD90− subpopulations. The difference in successful secondary engraftment, 12 of 12 (100%) for CD90+ versus 3 of 8 (37.5%) for CD90−, was statistically significant with p=0.004. B. Bone marrow engraftment in secondary recipients from experiment 1. Primary mice were transplanted with 2000 cells of the indicated population. The percent human chimerism (left) and percent myeloid cells of total human CD45+ cells (right) is indicated for each secondary mouse. Each circle or triangle represents an individual mouse. C. Bone marrow engraftment in secondary recipients from experiment 2. Primary mice were transplanted with 500 cells of the indicated population. The percent human chimerism (left) and percent myeloid cells of total human CD45+ cells (right) is indicated for each secondary mouse. Each circle or triangle represents an individual mouse.

Enrichment of Secondary Transplant Ability in the CD90+CD45RA− Subpopulation. Self-renewal is the key property distinguishing HSC from MPP, and is defined by the ability to sustain long-term hematopoiesis and generate successful secondary transplants. Since both the CD90+CD45RA− and CD90−CD45RA− subpopulations demonstrated the ability to establish long-term in vivo multipotent hematopoiesis, we next assessed their ability to generate successful secondary transplants. Human CD34+ cells were purified from whole bone marrow of primary engrafted mice and equal numbers of CD34+ cells were transplanted into NOG newborn mice. Bone marrows from these secondary recipients were analyzed at least 10 weeks after transplantation. In one experiment, 130,000 human CD34+ cells were transplanted into secondary recipients. Human CD45+ cells and human myeloid cells were detected in 8 of 8 mice (100%) from CD90+ primary transplants, but only 2 of 5 mice (40%) from CD90− primary transplants (FIG. 7A,B). In a second experiment, 70,000 human CD34+ cells were transplanted into secondary recipients. Human CD45+ cells and human myeloid cells were detected in 4 of 4 mice (100%) from CD90+ primary transplants, but only 1 of 3 mice (40%) from CD90− primary transplants (FIG. 7A,C). This difference, 12 of 12 (100%) for CD90+ versus 3 of 8 (37.5%) for CD90−, was statistically significant with p=0.004. These data indicate that the CD90+CD45RA− subpopulation is enriched for the ability to generate successful secondary transplants compared to the CD90−CD45RA− subpopulation.

HSC are defined by two key functional properties: (1) multipotency, defined as the ability to form all differentiated blood cells, and (2) long-term self-renewal, defined as the ability to give rise to progeny identical to the parent through cell division. It is this property of self-renewal that distinguishes HSC from multipotent progenitors, and is experimentally demonstrated through the ability to generate successful secondary transplants. We show here that both CD90+CD45RA− and CD90−CD45RA− cord blood cells are able to establish long-term multipotent hematopoiesis in vivo, and that the CD90+CD45RA− subpopulation is enriched for the ability to generate successful secondary transplants. We conclude that the CD90+CD45RA− subpopulation contains HSC, while the CD90−CD45RA− subpopulation contains candidate multipotent progenitors. This represents the first identification and prospective isolation of a population of candidate human multipotent progenitors.

Both the CD90+CD45RA− and CD90−CD45RA− cells are able to establish multipotent long-term human hematopoiesis in vivo; however, the CD90−CD45RA− subpopulation requires more cells to accomplish this as indicated by the failure of 50 and 70 cell transplants to long-term engraft, unlike the CD90+CD45RA− subpopulation which engrafts long-term with as few as 10 cells. The fact that 50 CD90−CD45RA− cells show myeloid and B lymphoid engraftment at 4 weeks, but not 12 weeks, indicates that this fraction contains non-HSC multipotent cells. Thus, we have demonstrated that CD90−CD45RA− cells are multipotent, exhibit a reduced and incomplete capacity for self-renewal, and lie downstream of CD90+CD45RA− cells in the hematopoietic hierarchy. We conclude that CD90−CD45RA− cells are a multipotent hematopoietic progenitor.

Hematopoiesis proceeds through an organized hierarchy in which lineage potential becomes increasingly restricted and a given population can only give rise to downstream populations. We investigated the hierarchical relationships between the CD90/CD45RA subpopulations of Lin−CD34+ CD38− cord blood and found that both in vitro and in vivo, the CD90+CD45RA− population gives rise to itself and both the CD90−CD45RA− and CD90−CD45RA+ subpopulations. CD90−CD45RA− cells do not give rise to CD90+ cells, but can form both CD90− subpopulations. In vitro the CD90−CD45RA+ cells give rise principally to itself only. These results establish a hierarchy among Lin−CD34+ CD38− cord blood cells in which CD90+CD45RA− cells are upstream of CD90−CD45RA− cells, which are upstream of CD90−CD45RA+ cells.

CD90 and CD45RA identify a third population within the Lin−CD34+CD38− fraction of cord blood and bone marrow, the CD90−CD45RA+ subpopulation. Transplantation with up to 900 of these cells does not result in any circulating human hematopoietic cells at 4 weeks after transplantation, and there are no detectable human cells in the bone marrow at 12 weeks. Furthermore, these cells have extremely poor methylcellulose colony forming ability, yielding only 6 colonies from 180 plated cells, suggesting that they possess limited myeloid differentiation potential. These cells also did not proliferate in liquid culture under conditions able to promote the growth of the other two subpopulations. It is interesting to note, that cells with this immunophenotype can be found within the bone marrow of mice engrafted with either the CD90+CD45RA− or CD90−CD45RA− subpopulation. Thus, it is likely that they contribute to ongoing human hematopoiesis, but at this time cannot be placed within the hematopoietic hierarchy.

Numerous xenotransplantation experiments have reported the successful enrichment of human HSC activity in Lin−CD34+CD38−/lo fractions of human hematopoietic progenitors through the demonstration of long-term multipotent engraftment and successful secondary transplantation. In published reports, successful secondary engraftment has required primary transplantation of large numbers of cells, minimally thousands and usually many more. We report here long-term in vivo human engraftment and successful secondary engraftment with transplantation of 500 purified Lin−CD34+CD38−CD90+CD45RA− cord blood cells. The major differences between our results and previous reports are: (1) the use of the NOG newborn mice, which appear to be well-suited for human hematopoietic engraftment, and (2) the combination of Lin−CD34+CD38−CD90+ CD45RA− markers for HSC purification. With this immunophenotype and xenotransplantation assay, we have directly isolated cord blood HSC activity to fewer cells than in previous reports.

Implications for Human Acute Myeloid Leukemia. Analogous to normal hematopoiesis, human acute myeloid leukemia (AML) is organized as a hierarchy initiated by leukemia stem cells (LSC) that are able to self-renew and give rise to all the cells within the leukemia (Tan et al. (2006) Lab Invest 86, 1203-1207; Wang and Dick (2005) Trends Cell Biol 15, 494-501). In a series of xenotransplantation experiments, Dick and colleagues first demonstrated the existence of human AML LSC and localized them to the Lin−CD34+ CD38− fraction of AML (Bonnet and Dick (1997) Nat Med 3, 730-737; Lapidot et al. (1994) Nature 367, 645-648). Based on these observations, a model was proposed in which HSC are the cell of origin for AML LSC. However, subsequent experiments indicated that AML LSC, unlike HSC, do not express CD90 (Miyamoto et al. (2000) Proc Natl Acad Sci USA 97, 7521-7526). There are two hypotheses to account for this difference: (1) AML LSC are indeed derived from HSC, but have aberrantly lost expression of CD90, or (2) AML LSC do not derive from HSC but instead come from a downstream progenitor that lacks expression of CD90.

Evidence supporting the second hypothesis comes from previous studies of AML1-ETO translocation-associated AML in atom bomb survivors from Hiroshima (Miyamoto et al., 2000). The AML LSC were contained in the Lin−CD34+ CD38−CD90− fraction (Blair et al. (1997) Blood 89, 3104-3112). However, when the bone marrow of long-term disease-free survivors was examined, the AML1-ETO translocation was detected in Lin−CD34+CD38−CD90+ non-leukemic HSC. This demonstrates that pre-leukemic genetic changes can take place within HSC, but ultimate transformation to AML LSC requires additional mutations that do not occur in HSC, but instead take place in a CD90− downstream population.

Why does this matter? If the normal counterpart to long-term self-renewing AML LSC is not capable of long-term self-renewal itself, then AML LSC must have undergone mutational or epigenetic activation of a self-renewal pathway. These changes, when identified, become targets for therapeutic intervention to eradicate the LSC. Evidence for aberrant activation of self-renewal in LSC comes from studies of human blast crisis CML, where normally non-self-renewing cells transform into LSC in part through activation of the Wnt/beta-catenin pathway (Jamieson et al. (2004) N Engl J Med 351, 657-667). Through comparisons between AML LSC and the newly identified MPP, genetic and/or epigenetic events than lead to the transformation of MPP into AML LSC are identified.

Experimental Procedures

Human Samples. Normal human bone marrow mononuclear cells were purchased from AllCells Inc. (Emeryville, Calif.). Human cord blood was collected from placentas and/or umbilical cords obtained from the Stanford Medical Center, according to an IRB-approved protocol (Stanford IRB #4637). Mononuclear cells were prepared using Ficoll-Paque Plus (GE Healthcare, Fairfield, Conn.), and cryopreserved in 90% FBS/10% DMSO. All experiments were conducted with cryopreserved cord blood cells that were thawed and washed with IMDM containing 10% FBS. In some cases, CD34+ cells were enriched using MACS (Miltenyi Biotec, Germany) or Robosep (Stem Cell Technologies, Canada) immunomagnetic beads.

Flow Cytometry Analysis and Cell Sorting. A panel of antibodies was used for analysis and sorting of progenitor subpopulations, as well as lineage analysis of human chimerism/engraftment, and used to stain cell suspensions (Supplementary Methods). Cells were either analyzed or sorted using a FACSAria cytometer (BD Biosciences). Analysis of flow cytometry data was performed using FlowJo Software (Treestar, Ashland, Oreg.). Raw engraftment data is provided in Supplementary FIG. 3. Statistical analysis using Student's t-test or Fisher's exact test was performed with Microsoft Excel and/or GraphPad Prism (San Diego, Calif.) software.

In Vitro Assays: Cytology, Methylcellulose, and Liquid Culture. For cytologic analysis, sorted cells were centrifuged onto slides using a Shandon Cytocentrifuge 4 (Thermo Scientific, Waltham, Mass.), and stained with Wright-Giemsa. Photomicrographs were taken using a 100× objective under oil.

Methylcellulose colony formation was assayed by clone-sorting single cells into individual wells of a 96-well plate, each containing 100 µl of complete methylcellulose (Methocult GF+ H4435, Stem Cell Technologies). Plates were incubated for 12-14 days at 37° C., then scored based on morphology. All colonies were harvested, dissociated by resuspending in sterile PBS, and replated into individual wells of a 24-well plate, each containing 500 µl of complete methylcellulose. Plates were incubated for 12-14 days at 37° C., after which replating was determined by assessing colony formation. Statistical analysis using Student's t-test was performed with Microsoft Excel and/or GraphPad Prism (San Diego, Calif.) software.

In vitro proliferation was assayed by clone-sorting single cells into individual wells of a 96-well plate, each containing 100 µl of StemSpan media (Stem Cell Technologies), supplemented with 40 µg/ml human LDL (Sigma-Aldrich) and cytokines (R&D Systems, Minneapolis, Minn.): 100 ng/ml Flt-3 ligand, 100 ng/ml SCF, 50 ng/ml TPO, 20 ng/ml IL-3, and 20 ng/ml IL-6. Plates were incubated for 14 days at 37° C., after which live cells were counted by trypan blue exclusion. For in vitro differentiation assays, cells were sorted in bulk into this same culture media and incubated for 3-4 days at 37° C., after which cells were harvested and analyzed by flow cytometry. Statistical analysis using Student's t-test was performed with Microsoft Excel and/or GraphPad Prism (San Diego, Calif.) software.

Mouse Transplantation. NOD.Cg-Prkdc$^{scid}$Il2rg$^{tm1wjl}$/SzJ mice (NOG) were obtained from The Jackson Laboratory (Bar Harbor, Me.) and bred in a Specific Pathogen-Free environment per Stanford Administrative Panel on Laboratory Animal Care guidelines (Protocol 10725). P0-P2 newborn pups were conditioned with 100 rads of gamma irradiation up to 24 hours prior to transplantation (Ishikawa et al., 2005). Desired cells were resuspended in 20-40 ul of PBS containing 2% FBS and transplanted intravenously via the anterior facial vein using a 30 or 31 gauge needle. For secondary transplants, human CD34+ bone marrow cells from primary engrafted mice were enriched using MACS immunomagnetic beads (Miltenyi Biotec), and transplanted into newborn NOG recipients.

Example 2

Identification of Cell Surface Molecules Preferentially Expressed on Human Acute Myeloid Leukemia Stem Cells Compared to Their Normal Counterparts Prospective Identification of a Human Multipotent Progenitor, the Cell of Origin for AML LSC. Identification of cell surface molecules that are preferentially expressed on AML LSC would be greatly facilitated by determining the cell within the normal hematopoietic hierarchy that undergoes transformation to become an AML LSC. The prevailing view in the field has been that AML LSC arise out of hematopoietic stem cells (HSC), since both stem cell populations are enriched in Lin−CD34+CD38− cells. However, human HSC have been shown to express CD90, while AML LSC are CD90−. Furthermore, HSC from long-term remission t(8;21) AML patients were found to contain the AML1-ETO translocation product, suggesting that the HSC were pre-leukemic, and that full transformation to AML LSC occurred in a downstream progenitor.

While it is certainly possible that HSC are in fact the cell of origin for AML LSC, and that these cells lose expression of CD90 as a consequence of transformation, it is also possible that AML LSC originate from downstream Lin−CD34+CD38−CD90− cells. We utilized a NOD/SCID/IL-2R gamma null (NOG) newborn xenotransplantation model to assay the function of subpopulations of Lin−CD34+CD38− cord blood, identified on the basis of CD90 and CD45RA expression. Lin−CD34+CD38−CD90+ cells produced long-term multi-lineage engraftment and formed successful secondary transplants, and therefore contained HSC. Transplantation of purified Lin−CD34+CD38−CD90−CD45RA− cells resulted in lower levels of multi-lineage engraftment in primary recipients, and a statistically significant reduced ability to form long-term secondary transplants. In fact, with transplantation of 50 purified cells, these cells failed to long-term engraft, unlike the Lin−CD34+CD38−CD90+ HSC. Thus, Lin−CD34+CD38−CD90−CD45RA− cells are multipotent and possess limited self-renewal ability. These cells are termed multipotent progenitors (MPP) and represent the possible cell of origin of AML LSC.

Use of Gene Expression Profiling to Identify Cell Surface Molecules Preferentially Expressed on AML LSC Compared to Their Normal Counterparts, HSC and MPP. Cell surface molecules preferentially expressed on human acute myeloid leukemia stem cells (AML LSC) compared to their normal counterparts have therapeutic applications outlined below. One strategy to identify such molecules has been to generate gene expression profiles of AML LSC and normal HSC and MPP, and compare them for differentially expressed genes.

Figure 8:
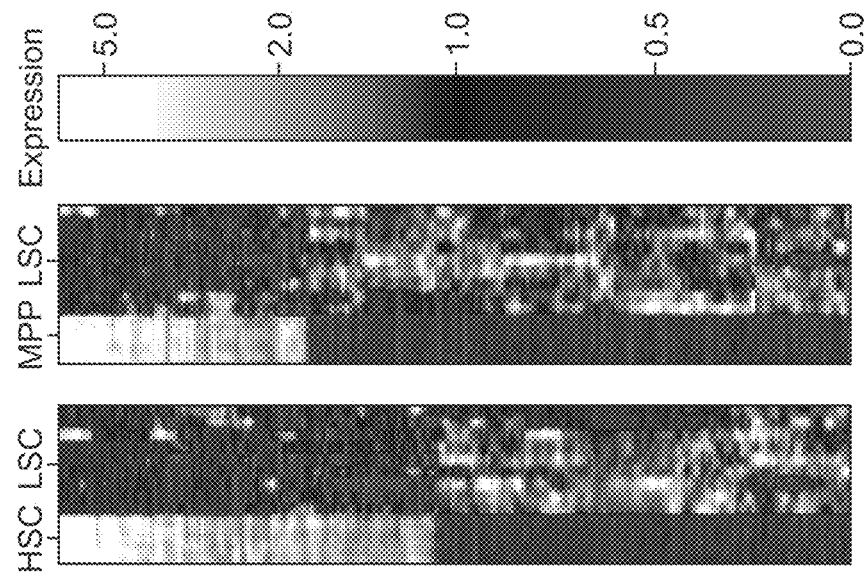
FIG. 8: Differential Gene Expression Between AML LSC and Normal Bone Marrow HSC and MPP (A) Heat maps demonstrating genes found to be differentially expressed at least 2 fold between bone marrow HSC (n=4) and AML LSC (n=9) or bone marrow MPP (n=4) and AML LSC (n=9). Expression relative to the median is indicated for genes with p<0.05 and a FDR of 5%. (B) Selected list of transmembrane proteins found to be at least 2-fold more highly expressed in AML LSC than HSC of MPP. NS: not significant.
Figure 7:
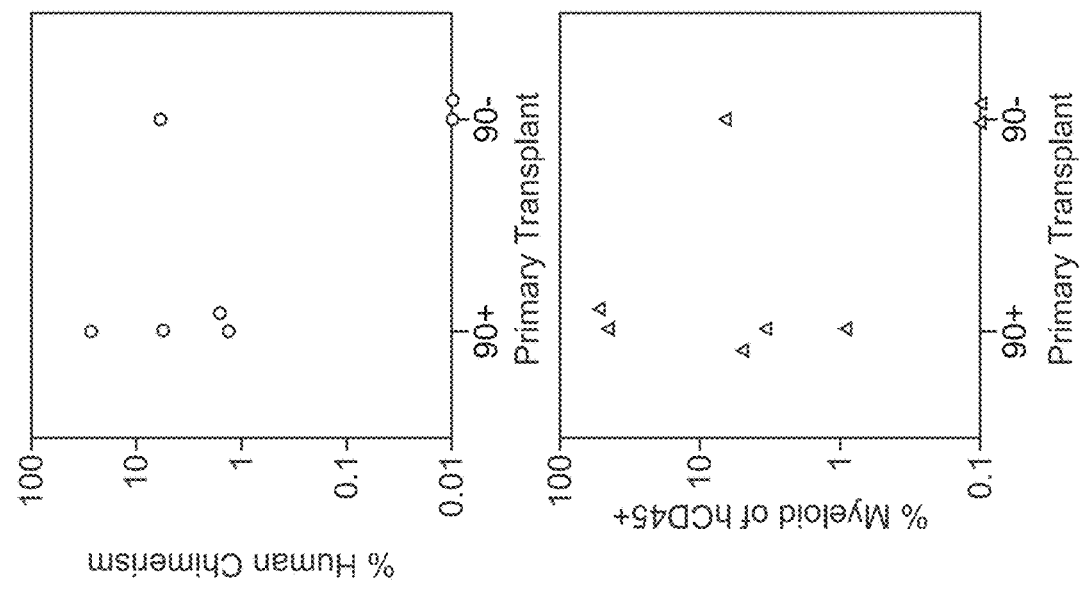

Normal bone marrow HSC and MPP (n=4) and AML LSC (n=9) were purified by FACS. Total RNA was prepared, amplified, and hybridized to Affymetrix human DNA microarrays. Statistical analysis identified 4037 genes differentially expressed between HSC and LSC, and 4208 genes differentially expressed between MPP and LSC, with $p<0.05$ and a False Discovery Rate of 5% (FIG. 8A). Investigation of these differentially expressed genes identified 288 and 318 cell surface molecules preferentially expressed in AML LSC by at least 2-fold compared to HSC and MPP, respectively. Selected members of this list, including many with the greatest preferential expression in AML LSC are indicated (FIG. 8B, Table 1).

TABLE 1

| Fold Change | Genbank | Gene Symbol | Description |
|---|---|---|---|
| 94.34 | M27331 | TRGC2 | T cell receptor gamma constant 2 |
| 57.47 | NM_005816 | CD96 | CD96 antigen |
| 47.17 | AI862120 | MAMDC2 | MAM domain containing 2 |
| 32.36 | AF348078 | SUCNR1 | succinate receptor 1 |
| 32.05 | M16768 | TRGC2 | T cell receptor gamma constant 2 |
| 30.96 | NM_002182 | IL1RAP | interleukin 1 receptor accessory protein |
| 29.85 | M13231 | TRGC2 | T cell receptor gamma constant 2 |
| 27.55 | NM_003332 | TYROBP | TYRO protein tyrosine kinase binding protein |
| 26.88 | NM_004271 | LY86 | lymphocyte antigen 86 |
| 20.96 | NM_014879 | P2RY14 | purinergic receptor P2Y, G-protein coupled, 14 |
| 18.38 | BC020749 | CD96 | CD96 antigen |
| 18.38 | NM_005048 | PTHR2 | parathyroid hormone receptor 2 |
| 17.73 | AI625747 | ADRB1 | Adrenergic, beta-1-, receptor |
| 17.36 | NM_015376 | RASGRP3 | RAS guanyl releasing protein 3 (calcium and DAG-regulated) |
| 16.84 | U62027 | C3AR1 | complement component 3a receptor 1 |
| 14.49 | AW025572 | HAVCR2 | hepatitis A virus cellular receptor 2 |
| 12.48 | AF285447 | HCST | hematopoietic cell signal transducer |
| 11.92 | AI805323 | LGR7 | leucine-rich repeat-containing G protein-coupled receptor 7 |
| 11.67 | NM_001197 | BIK | BCL2-interacting killer (apoptosis-inducing) |
| 11.53 | NM_018092 | NETO2 | neuropilin (NRP) and tolloid (TLL)-like 2 |
| 11.07 | N74607 | AQP3 | aquaporin 3 |
| 10.88 | BF439675 | CD69 | CD69 antigen (p60, early T-cell activation antigen) |
| 10.48 | NM_001769 | CD9 | CD9 antigen (p24) |
| 10.32 | AF167343 | IL1RAP | interleukin 1 receptor accessory protein |
| 9.52 | AA814140 | C5orf18 | chromosome 5 open reading frame 18 |
| 8.77 | NM_005582 | CD180 | CD180 antigen |
| 7.46 | AF039686 | GPR34 | G protein-coupled receptor 34 |
| 7.30 | AI056776 | ITGA6 | Integrin, alpha 6 |
| 7.19 | AJ277151 | TNFRSF4 | tumor necrosis factor receptor superfamily, member 4 |
| 6.99 | AI738675 | SELPLG | Selectin P ligand |
| 6.85 | AA888858 | PDE3B | Phosphodiesterase 3B, cGMP-inhibited |
| 6.80 | AU149572 | ADCY2 | adenylate cyclase 2 (brain) |

TABLE 1-continued

| Fold Change | Genbank | Gene Symbol | Description |
|---|---|---|---|
| 6.80 | NM_002299 | LCT | lactase |
| 6.58 | NM_005296 | GPR23 | G protein-coupled receptor 23 |
| 6.45 | NM_004106 | FCER1G | Fc fragment of IgE, high affinity receptor |
| 6.29 | AI741056 | SELPLG | selectin P ligand |
| 6.25 | AW406569 | MGC15619 | |
| 6.06 | M81695 | ITGAX | integrin, alpha X |
| 5.92 | NM_003494 | DYSF | dysferlin |
| 5.85 | AI860212 | PAG1 | phosphoprotein associated with glycosphingolipid microdomains 1 |
| 5.75 | NM_013447 | EMR2 | egf-like module containing, mucin-like, hormone receptor-like 2 |
| 5.62 | NM_017806 | LIME1 | Lck interacting transmembrane adaptor 1 |
| 5.62 | AK092824 | AMN | Amnionless homolog (mouse) |
| 5.59 | AF345567 | GPR174 | G protein-coupled receptor 174 |
| 5.29 | BC041928 | IL1RAP | Interleukin 1 receptor accessory protein |
| 5.26 | L03419 | FCGR1A | Fc fragment of IgG, high affinity Ia, receptor (CD64); Fc-gamma receptor I B2 |
| 5.24 | BG230586 | SLC7A6 | solute carrier family 7 (cationic amino acid transporter, y + system), member 6 |
| 5.18 | AF015524 | CCRL2 | chemokine (C-C motif) receptor-like 2 |
| 5.13 | AA631143 | SLC45A3 | solute carrier family 45, member 3 |
| 5.10 | AJ240085 | TRAT1 | T cell receptor associated transmembrane adaptor 1 |
| 5.05 | AW183080 | GPR92 | G protein-coupled receptor 92 |
| 5.03 | NM_002120 | HLA-DOB | major histocompatibility complex, class II, DO beta |
| 5.03 | NM_015364 | LY96 | lymphocyte antigen 96 |
| 4.90 | NM_020399 | GOPC | golgi associated PDZ and coiled-coil motif containing |
| 4.88 | AK026133 | SEMA4B | semaphorin |
| 4.88 | BC041664 | VMD2 | vitelliform macular dystrophy 2 |
| 4.85 | NM_152592 | C14orf49 | chromosome 14 open reading frame 49 |
| 4.85 | AA923524 | RASGRP4 | RAS guanyl releasing protein 4 |
| 4.85 | BC008777 | ITGAL | integrin, alpha L) |
| 4.67 | AF014403 | PPAP2A | phosphatidic acid phosphatase type 2A |
| 4.65 | AK097698 | SORCS2 | Sortilin-related VPS10 domain containing receptor 2 |
| 4.63 | X14355 | FCGR1A | Fc fragment of IgG, high affinity Ia, receptor (CD64) |
| 4.55 | NM_001629 | ALOX5AP | arachidonate 5-lipoxygenase-activating protein |
| 4.50 | AU155968 | C18orf1 | chromosome 18 open reading frame 1 |
| 4.44 | AK075092 | HERV-FRD | HERV-FRD provirus ancestral Env polyprotein |
| 4.42 | NM_020960 | GPR107 | G protein-coupled receptor 107 |
| 4.37 | BC000039 | FAM26B | family with sequence similarity 26, member B |
| 4.35 | NM_153701 | IL12RB1 | interleukin 12 receptor, beta 1 |
| 4.35 | AI762344 | PTGER1 | prostaglandin E receptor 1 (subtype EP1), 42 kDa |
| 4.31 | NM_006459 | SPFH1 | SPFH domain family, member 1 |
| 4.27 | NM_003126 | SPTA1 | spectrin, alpha, erythrocytic 1 (elliptocytosis 2) |
| 4.22 | AL518391 | AQP1 | aquaporin 1 (channel-forming integral protein, 28 kDa) |
| 4.12 | AK026188 | PCDHGC3 | protocadherin gamma subfamily C |
| 4.10 | AU146685 | EDG2 | Endothelial differentiation, lysophosphatidic acid G-protein-coupled receptor, 2 |
| 4.05 | BE673587 | SLC14A1 | Solute carrier family 14 (urea transporter), member 1 (Kidd blood group) |
| 4.02 | BF129969 | TSPAN2 | tetraspanin 2 |
| 4.00 | AW243272 | KCNK5 | Potassium channel, subfamily K, member 5 |
| 3.98 | T68858 | DHRS3 | Dehydrogenase/reductase (SDR family) member 3 |
| 3.94 | AI827849 | VTI1A | Vesicle transport through interaction with t-SNAREs homolog 1A (yeast) |
| 3.86 | AL134012 | NRXN2 | Neurexin 2 |
| 3.83 | BG230614 | CD47 | CD47 antigen |
| 3.80 | AI869717 | MGC15523 | MGC15523 |
| 3.80 | AI458583 | SIMP | Source of immunodominant MHC-associated peptides |
| 3.79 | NM_002183 | IL3RA | interleukin 3 receptor, alpha (low affinity) |
| 3.79 | AA608820 | NRXN2 | neurexin 2 |
| 3.73 | NM_000206 | IL2RG | interleukin 2 receptor |
| 3.72 | BC002737 | VAMP2 | synaptobrevin 2 |
| 3.72 | BC005884 | BID | BH3 interacting domain death agonist; BH3 interacting domain death agonist |
| 3.68 | AI688418 | PLXNA2 | plexin A2 |
| 3.68 | BC003105 | PTP4A3 | protein tyrosine phosphatase type IVA, member 3 |
| 3.68 | NM_001772 | CD33 | CD33 antigen (gp67) |
| 3.65 | BC007524 | SPAG9 | sperm associated antigen 9 |
| 3.64 | AI344200 | SLC25A35 | solute carrier family 25, member 35 |
| 3.64 | B0005253 | KLHL20 | kelch-like 20 (Drosophila) |
| 3.60 | AI335263 | NETO2 | neuropilin (NRP) and tolloid (TLL)-like 2 |
| 3.58 | BF381837 | C20orf52 | chromosome 20 open reading frame 52 |
| 3.51 | NM_002886 | RAP2A | RAP2A |
| 3.50 | NM_007063 | TBC1D8 | TBC1 domain family, member 8 (with GRAM domain) |
| 3.45 | AK027160 | BCL2L11 | BCL2-like 11 (apoptosis facilitator) |
| 3.44 | BF055366 | EDG2 | endothelial differentiation, lysophosphatidic acid G-protein-coupled receptor, 2 |

TABLE 1-continued

| Fold Change | Genbank | Gene Symbol | Description |
|---|---|---|---|
| 3.42 | NM_003608 | GPR65 | G protein-coupled receptor 65 |
| 3.41 | AI675453 | PLXNA3 | plexin A3 |
| 3.40 | AV734194 | DPP8 | dipeptidylpeptidase 8 |
| 3.38 | B0000232 | C5orf18 | chromosome 5 open reading frame 18 |
| 3.36 | B0001956 | KIAA1961 | KIAA1961 gene |
| 3.34 | NM_013332 | HIG2 | hypoxia-inducible protein 2 |
| 3.31 | BC029450 | SLC33A1 | Solute carrier family 33 (acetyl-CoA transporter), member 1 |
| 3.30 | AW008505 | C18orf1 | chromosome 18 open reading frame 1 |
| 3.29 | BF693956 | CD47 | CD47 antigen |
| 3.28 | BF677986 | KIAA1961 | KIAA1961 gene |
| 3.27 | AI433691 | CACNA2D4 | calcium channel, voltage-dependent, alpha 2/delta subunit 4 |
| 3.26 | AB014573 | NPHP4 | nephronophthisis 4 |
| 3.25 | AL582804 | LY9 | lymphocyte antigen 9 |
| 3.25 | BG236280 | CD86 | CD86 antigen |
| 3.24 | AA639289 | 5LC26A7 | Solute carrier family 26, member 7 |
| 3.24 | NM_005211 | CSF1R | colony stimulating factor 1 receptor |
| 3.24 | AI051254 | TRPM2 | transient receptor potential cation channel, subfamily M, member 2 |
| 3.23 | AW292816 | ABHD2 | abhydrolase domain containing 2 |
| 3.23 | BC040275 | RASGRF1 | Ras protein-specific guanine nucleotide-releasing factor 1 |
| 3.22 | NM_021911 | GABRB2 | gamma-aminobutyric acid (GABA) A receptor, beta 2 |
| 3.19 | AI660619 | SLC7A6 | solute carrier family 7 (cationic amino acid transporter, y + system), member 6 |
| 3.19 | NM_001860 | SLC31A2 | solute carrier family 31 (copper transporters), member 2 |
| 3.18 | NM_015680 | C2orf24 | chromosome 2 open reading frame 24 |
| 3.17 | AW058600 | SLC36A1 | solute carrier family 36 |
| 3.16 | AU145049 | HIP1 | Huntingtin interacting protein 1 |
| 3.15 | NM_005770 | SERF2 | small EDRK-rich factor 2 |
| 3.15 | NM_003566 | EEA1 | Early endosome antigen 1, 162 kD |
| 3.14 | NM_020041 | SLC2A9 | solute carrier family 2 (facilitated glucose transporter), member 9 |
| 3.14 | W90718 | SLC24A4 | solute carrier family 24 |
| 3.13 | AI423165 | TICAM2 | toll-like receptor adaptor molecule 2 |
| 3.12 | AI674647 | SPPL2A | signal peptide peptidase-like 2A |
| 3.11 | NM_004121 | GGTLA1 | gamma-glutamyltransferase-like activity 1 |
| 3.10 | NM_004546 | NDUFB2 | NADH dehydrogenase (ubiquinone) 1 beta subcomplex, 2, 8 kDa |
| 3.05 | X15786 | RET | ret proto-oncogene (multiple endocrine neoplasia and medullary thyroid carcinoma 1, Hirschsprung disease) |
| 3.05 | AF181660 | MPZL1 | myelin protein zero-like 1 |
| 3.05 | BG230614 | CD47 | CD47 antigen (Rh-related antigen, integrin-associated signal transducer) |
| 3.00 | AI571996 | STAM2 | signal transducing adaptor molecule (SH3 domain and ITAM motif) 2 |
| 2.99 | NM_000201 | ICAM1 | intercellular adhesion molecule 1 (CD54), human rhinovirus receptor |
| 2.93 | NM_025244 | TSGA10 | testis specific, 10 |
| 2.93 | AU147538 | PRKCE | Protein kinase C, epsilon |
| 2.92 | NM_024576 | OGFRL1 | opioid growth factor receptor-like 1 |
| 2.91 | AI248055 | ABCC4 | ATP-binding cassette, sub-family C (CFTR/MRP), member 4 |
| 2.86 | AA503877 | CEPT1 | Choline/ethanolamine phosphotransferase 1 |
| 2.84 | BC030993 | FLJ21127 | Hypothetical protein FLJ21127 |
| 2.82 | AA829818 | LY86 | Lymphocyte antigen 86 |
| 2.82 | NM_001859 | SLC31A1 | solute carrier family 31 (copper transporters), member 1 |
| 2.81 | M74721 | CD79A | CD79A antigen (immunoglobulin-associated alpha) |
| 2.79 | AI986112 | MGAT4B | Mannosyl (alpha-1,3-)-glycoprotein beta-1,4-N-acetylglucosaminyltransferase, isoenzyme B |
| 2.79 | NM_030930 | UNC93B1 | unc-93 homolog B1 (C. elegans); unc-93 homolog B1 (C. elegans) |
| 2.79 | X74039 | PLAUR | plasminogen activator, urokinase receptor |
| 2.78 | BF514291 | LY86 | Lymphocyte antigen 86 |
| 2.75 | BC005253 | KLHL20 | kelch-like 20 (Drosophila) |
| 2.73 | AB036432 | AGER | advanced glycosylation end product-specific receptor |
| 2.71 | NM_007245 | ATXN2L | ataxin 2-like |
| 2.71 | NM_016072 | GOLT1B | golgi transport 1 homolog B (S. cerevisiae) |
| 2.71 | AI453548 | ZDHHC8 | zinc finger, DHHC-type containing 8 |
| 2.70 | AI636233 | TMEM8 | transmembrane protein 8 (five membrane-spanning domains) |
| 2.69 | BE502509 | T3JAM | TRAF3 interacting protein 3 |
| 2.69 | AW117765 | PEX13 | peroxisome biogenesis factor 13 |
| 2.69 | AW052216 | IL17RB | Interleukin 17 receptor B |
| 2.67 | NM_003853 | IL18RAP | interleukin 18 receptor accessory protein |

TABLE 1-continued

| Fold Change | Genbank | Gene Symbol | Description |
|---|---|---|---|
| 2.66 | NM_002490 | NDUFA6 | NADH dehydrogenase (ubiquinone) 1 alpha subcomplex, 6,14 kDa |
| 2.65 | NM_016639 | TNFRSF12A | tumor necrosis factor receptor superfamily, member 12A |
| 2.65 | AI363185 | FLJ20255 | Hypothetical protein FLJ20255 |
| 2.65 | NM_052931 | SLAMF6 | SLAM family member 6 |
| 2.65 | AW571669 | TNFRSF19L | tumor necrosis factor receptor superfamily, member 19-like |
| 2.64 | AA654142 | CEECAM1 | cerebral endothelial cell adhesion molecule 1 |
| 2.62 | AW510783 | TMEM63A | transmembrane protein 63A |
| 2.61 | W95007 | ACSL4 | Acyl-CoA synthetase long-chain family member 4 |
| 2.60 | S76475 | NTRK3 | neurotrophic tyrosine kinase, receptor, type 3 |
| 2.60 | AJ130713 | SIGLEC7 | sialic acid binding Ig-like lectin 7 |
| 2.56 | NM_003775 | EDG6 | endothelial differentiation, G-protein-coupled receptor 6 |
| 2.55 | AI978986 | MAMDC4 | MAM domain containing 4 |
| 2.54 | AF010447 | MR1 | major histocompatibility complex, class I-related |
| 2.54 | NM_006068 | TLR6 | toll-like receptor 6 |
| 2.53 | AF041811 | NTRK3 | neurotrophic tyrosine kinase, receptor, type 3 |
| 2.53 | AW953521 | SERF2; HYPK | small EDRK-rich factor 2; Huntingtin interacting protein K |
| 2.51 | AW293276 | CD53 | CD53 antigen |
| 2.49 | AK023058 | PLXNA2 | Plexin A2 |
| 2.49 | AI125204 | C6orf128 | chromosome 6 open reading frame 128 |
| 2.49 | NM_000392 | ABCC2 | ATP-binding cassette, sub-family C (CFTR/MRP), member 2 |
| 2.46 | B0032474 | TIRAP | toll-interleukin 1 receptor (TIR) domain containing adaptor protein |
| 2.44 | NM_031211 | IMAA | SLC7A5 pseudogene |
| 2.44 | AI797836 | CD5 | CD5 antigen (p56-62) |
| 2.41 | W72082 | C1QR1 | complement component 1 |
| 2.40 | AA708616 | DPP9 | dipeptidylpeptidase 9 |
| 2.40 | BM987094 | DLGAP4 | discs, large (Drosophila) homolog-associated protein 4 |
| 2.40 | AL713719 | LOC283501 | ATPase, Class VI, type 11A |
| 2.39 | AI628734 | PRLR | prolactin receptor |
| 2.39 | NM_012110 | CHIC2 | cysteine-rich hydrophobic domain 2 |
| 2.38 | AK022002 | TFR2 | transferrin receptor 2 |
| 2.37 | NM_001555 | IGSF1 | immunoglobulin superfamily, member 1 |
| 2.36 | AA426091 | C19orf15 | chromosome 19 open reading frame 15 |
| 2.36 | BE547542 | GOPC | golgi associated PDZ and coiled-coil motif containing |
| 2.36 | NM_004231 | ATP6V1F | ATPase, H + transporting, lysosomal 14 kDa, V1 subunit F |
| 2.36 | AJ130712 | SIGLEC7 | sialic acid binding Ig-like lectin 7 |
| 2.36 | NM_017905 | TMCO3 | transmembrane and coiled-coil domains 3 |
| 2.35 | AB054985 | CACNB1 | calcium channel, voltage-dependent, beta 1 subunit |
| 2.35 | NM_005003 | NDUFAB1 | NADH dehydrogenase (ubiquinone) 1, alpha/beta subcomplex, 1, 8 kDa |
| 2.35 | NM_001251 | CD68 | CD68 antigen |
| 2.35 | AA700869 | PSCD2 | Pleckstrin homology, Sec7 and coiled-coil domains 2 (cytohesin-2) |
| 2.35 | U94903 | CD44 | CD44 antigen (homing function and Indian blood group system) |
| 2.35 | NM_003841 | TNFRSF10C | tumor necrosis factor receptor superfamily, member 10c, decoy without an intracellular domain |
| 2.33 | NM_004541 | NDUFA1 | NADH dehydrogenase (ubiquinone) 1 alpha subcomplex, 1, 7.5 kDa |
| 2.33 | BE567130 | KLRK1 | Killer cell lectin-like receptor subfamily K, member 1 |
| 2.31 | NM_017460 | CYP3A4 | cytochrome P450, family 3, subfamily A, polypeptide 4 |
| 2.31 | AI339536 | DSC1 | Desmocollin 1 |
| 2.31 | NM_001783 | CD79A | CD79A antigen (immunoglobulin-associated alpha); CD79A antigen (immunoglobulin-associated alpha) |
| 2.30 | AA333161 | VTI1A | vesicle transport through interaction with t-SNAREs homolog 1A (yeast) |
| 2.30 | AW134823 | CD6 | CD6 antigen ; CD6 antigen |
| 2.30 | AL137537 | ATP8B2 | ATPase, Class I, type 8B, member 2 |
| 2.29 | AI671983 | SLC2A9 | solute carrier family 2 (facilitated glucose transporter), member 9 |
| 2.29 | AA018187 | C22orf3 | chromosome 22 open reading frame 3 |
| 2.29 | AL117415 | ADAM33 | ADAM metallopeptidase domain 33 |
| 2.29 | NM_002588 | PCDHGC3 | protocadherin gamma subfamily C |
| 2.29 | NM_020960 | GPR107 | G protein-coupled receptor 107 |
| 2.29 | AK074635 | GENX-3414 | Genethonin 1 |
| 2.29 | BE138575 | ITGB5 | Integrin, beta 5 |
| 2.28 | NM_003830 | SIGLEC5 | sialic acid binding Ig-like lectin 5; sialic acid binding Ig-like lectin 5 |
| 2.28 | NM_013319 | UBIAD1 | UbiA prenyltransferase domain containing 1 |
| 2.28 | M63889 | FGFR1 | fibroblast growth factor receptor 1 (fms-related tyrosine kinase 2, Pfeiffer syndrome) |
| 2.27 | H67156 | MSCP | Solute carrier family 25, member 37 |

TABLE 1-continued

| Fold Change | Genbank | Gene Symbol | Description |
|---|---|---|---|
| 2.27 | BC006215 | SMEK2 | KIAA1387 protein; KIAA1387 protein |
| 2.27 | AL109653 | SLITRK2 | SLIT and NTRK-like family, member 2 |
| 2.27 | NM_007011 | ABHD2 | abhydrolase domain containing 2 |
| 2.26 | AI767210 | MGC11332 | Hypothetical protein MGC11332 |
| 2.26 | BF723605 | NRCAM | Neuronal cell adhesion molecule |
| 2.26 | R08129 | CDA08 | T-cell immunomodulatory protein |
| 2.26 | AF052059 | SEL1L | sel-1 suppressor of lin-12-like (C. elegans) |
| 2.26 | NM_005729 | PPIF | peptidylprolyl isomerase F (cyclophilin F) |
| 2.25 | BE858032 | ARL2L1 | ADP-ribosylation factor-like 2-like 1 |
| 2.25 | AI950390 | C14orf118 | Chromosome 14 open reading frame 118 |
| 2.24 | NM_017767 | SLC39A4 | solute carrier family 39 (zinc transporter), member 4 |
| 2.24 | AL110273 | SPTAN1 | Spectrin, alpha, non-erythrocytic 1 (alpha-fodrin) |
| 2.24 | AI077660 | CDA08 | T-cell immunomodulatory protein |
| 2.23 | AA488687 | SLC7A11 | solute carrier family 7, (cationic amino acid transporter, y + system) member 11 |
| 2.23 | NM_000634 | IL8RA | interleukin 8 receptor, alpha |
| 2.22 | AL390177 | MGC34032 | Solute carrier family 44, member 5 |
| 2.21 | NM_001531 | MR1 | major histocompatibility complex, class I-related |
| 2.21 | NM_003183 | ADAM17 | ADAM metallopeptidase domain 17 (tumor necrosis factor, alpha, converting enzyme) |
| 2.20 | AC003999 | SCAP2 | src family associated phosphoprotein 2 |
| 2.20 | BC014416 | SLC33A1 | solute carrier family 33 (acetyl-CoA transporter), member 1 |
| 2.20 | AF226731 | ADORA3 | adenosine A3 receptor |
| 2.19 | AI608725 | ICAM1 | intercellular adhesion molecule 1 (CD54), human rhinovirus receptor |
| 2.19 | U41163 | SLC6A8; FLJ43855 | solute carrier family 6 (neurotransmitter transporter, creatine), member 8; similar to sodium- and chloride-dependent creatine transporter |
| 2.19 | AU147799 | LRRC15 | leucine rich repeat containing 15 |
| 2.18 | AW337166 | LOC255104 | Transmembrane and coiled-coil domains 4 |
| 2.18 | NM_006505 | PVR | poliovirus receptor |
| 2.18 | AI638420 | CLIC4 | chloride intracellular channel 4 |
| 2.18 | AI167482 | SCUBE3 | Signal peptide, CUB domain, EGF-like 3 |
| 2.18 | AI739514 | HAS3 | hyaluronan synthase 3 |
| 2.18 | NM_005971 | FXYD3 | FXYD domain containing ion transport regulator 3 |
| 2.17 | AL022398 | TRAF3IP3 | TRAF3 interacting protein 3 |
| 2.17 | U90940 | FCGR2C | Fc fragment of IgG, low affinity IIc, receptor for (CD32) |
| 2.16 | BC023540 | SORCS1 | Sortilin-related VPS10 domain containing receptor 1 |
| 2.16 | AV713913 | OSTM1 | osteopetrosis associated transmembrane protein 1 |
| 2.15 | NM_024505 | NOX5 | NADPH oxidase, EF-hand calcium binding domain 5 |
| 2.15 | BC006178 | SEC22L3 | SEC22 vesicle trafficking protein-like 3 (S. cerevisiae); SEC22 vesicle trafficking protein-like 3 (S. cerevisiae) |
| 2.15 | BG151527 | GRIK5 | glutamate receptor, ionotropic, kainate 5 |
| 2.14 | AW001754 | NEGRI | neuronal growth regulator 1 |
| 2.14 | NM_013979 | BNIP1 | BCL2/adenovirus E1B 19 kDa interacting protein 1 |
| 2.14 | NM_018643 | TREM1 | triggering receptor expressed on myeloid cells 1 |
| 2.12 | NM_005284 | GPR6 | G protein-coupled receptor 6 |
| 2.11 | AA454190 | ZDHHC20 | zinc finger, DHHC-type containing 20 |
| 2.11 | AB048796 | TMPRSS13 | transmembrane protease, serine 13 |
| 2.11 | AL044520 | NYD-SP21 | testes development-related NYD-SP21 |
| 2.11 | BE463930 | TMAP1 | Matrix-remodelling associated 7 |
| 2.10 | NM_152264 | SLC39A13 | solute carrier family 39 (zinc transporter), member 13 |
| 2.08 | AL530874 | EPHB2 | EPH receptor B2 |
| 2.07 | NM_018668 | VPS33B | vacuolar protein sorting 33B (yeast) |
| 2.07 | NM_024531 | GPR172A | G protein-coupled receptor 172A |
| 2.07 | NM_023038 | ADAM19 | ADAM metallopeptidase domain 19 (meltrin beta) |
| 2.07 | BC001281 | TNFRSF10B | tumor necrosis factor receptor superfamily, member 10b |
| 2.07 | AF217749 | PCDHB9 | protocadherin beta 9 |
| 2.06 | AB030077 | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| 2.06 | AL137432 | SUSD1 | sushi domain containing 1 |
| 2.05 | NM_004518 | KCNQ2 | potassium voltage-gated channel, KQT-like subfamily, member 2 |
| 2.04 | AI672363 | VPS33B | vacuolar protein sorting 33B (yeast) |
| 2.04 | NM_006671 | SLC1A7 | solute carrier family 1 (glutamate transporter), member 7 |
| 2.03 | AA215519 | DLGAP1 | Discs, large (Drosophila) homolog-associated protein 1 |
| 2.02 | NM_004648 | PTPNS1 | protein tyrosine phosphatase, non-receptor type substrate 1 |
| 2.02 | NM_002564 | P2RY2 | purinergic receptor P2Y, G-protein coupled, 2 |
| 2.01 | BF511678 | SCUBE3 | Signal peptide, CUB domain, EGF-like 3 |
| 2.01 | BC013385 | CLEC7A | C-type lectin domain family 7, member A |

TABLE 2

| Fold Change | Genbank | Gene Symbol | Description |
|---|---|---|---|
| 57.47 | NM_005816 | CD96 | CD96 antigen |
| 32.36 | AF348078 | SUCNR1 | succinate receptor 1 |
| 30.96 | NM_002182 | IL1RAP | interleukin 1 receptor accessory protein |
| 27.55 | NM_003332 | TYROBP | TYRO protein tyrosine kinase binding protein |
| 26.88 | NM_004271 | LY86 | lymphocyte antigen 86 |
| 20.96 | NM_014879 | P2RY14 | purinergic receptor P2Y, G-protein coupled, 14 |
| 18.38 | NM_005048 | PTHR2 | parathyroid hormone receptor 2 |
| 17.73 | AI625747 | ADRB1 | Adrenergic, beta-1-, receptor |
| 17.36 | NM_015376 | RASGRP3 | RAS guanyl releasing protein 3 (calcium and DAG-regulated) |
| 16.84 | U62027 | C3AR1 | complement component 3a receptor 1 |
| 14.49 | AW025572 | HAVCR2 | hepatitis A virus cellular receptor 2 |
| 12.48 | AF285447 | HCST | hematopoietic cell signal transducer |
| 11.92 | AI805323 | LGR7 | leucine-rich repeat-containing G protein-coupled receptor 7 |
| 11.67 | NM_001197 | BIK | BCL2-interacting killer (apoptosis-inducing) |
| 11.53 | NM_018092 | NETO2 | neuropilin (NRP) and tolloid (TLL)-like 2 |
| 11.07 | N74607 | AQP3 | aquaporin 3 |
| 10.48 | NM_001769 | CD9 | CD9 antigen (p24) |
| 8.77 | NM_005582 | CD180 | CD180 antigen |
| 7.46 | AF039686 | GPR34 | G protein-coupled receptor 34 |
| 7.19 | AJ277151 | TNFRSF4 | tumor necrosis factor receptor superfamily, member 4 |
| 6.85 | AA888858 | PDE3B | Phosphodiesterase 3B, cGMP-inhibited |
| 6.80 | AU149572 | ADCY2 | adenylate cyclase 2 (brain) |
| 6.80 | NM_002299 | LCT | lactase |
| 6.58 | NM_005296 | GPR23 | G protein-coupled receptor 23 |
| 6.45 | NM_004106 | FCER1G | Fc fragment of IgE, high affinity I, receptor for; gamma polypeptide |
| 6.25 | AW406569 | MGC15619 | hypothetical protein MGC15619 |
| 6.06 | M81695 | ITGAX | integrin, alpha X (antigen CD11C (p150), alpha polypeptide) |
| 5.92 | NM_003494 | DYSF | dysferlin, limb girdle muscular dystrophy 2B (autosomal recessive) |
| 5.75 | NM_013447 | EMR2 | egf-like module containing, mucin-like, hormone receptor-like 2 |
| 5.62 | NM_017806 | LIME1 | Lck interacting transmembrane adaptor 1 |
| 5.62 | AK092824 | AMN | Amnionless homolog (mouse) |
| 5.59 | AF345567 | GPR174 | G protein-coupled receptor 174 |
| 5.26 | L03419 | FCGR1A; LOC440607 | Fc fragment of IgG, high affinity Ia, receptor (CD64); Fc-gamma receptor I B2 |
| 5.18 | AF015524 | CCRL2 | chemokine (C-C motif) receptor-like 2 |
| 5.13 | AA631143 | SLC45A3 | solute carrier family 45, member 3 |
| 5.10 | AJ240085 | TRAT1 | T cell receptor associated transmembrane adaptor 1 |
| 5.05 | AW183080 | GPR92 | G protein-coupled receptor 92 |
| 5.03 | NM_002120 | HLA-DOB | major histocompatibility complex, class II, DO beta |
| 5.03 | NM_015364 | LY96 | lymphocyte antigen 96 |

TABLE 3

| Fold Change | Genbank | Gene Symbol | Description |
|---|---|---|---|
| 57.47 | NM_005816 | CD96 | CD96 antigen |
| 32.36 | AF348078 | SUCNR1 | succinate receptor 1 |
| 30.96 | NM_002182 | IL1RAP | interleukin 1 receptor accessory protein |
| 27.55 | NM_003332 | TYROBP | TYRO protein tyrosine kinase binding protein |
| 26.88 | NM_004271 | LY86 | lymphocyte antigen 86 |
| 20.96 | NM_014879 | P2RY14 | purinergic receptor P2Y, G-protein coupled, 14 |
| 18.38 | NM_005048 | PTHR2 | parathyroid hormone receptor 2 |
| 17.73 | AI625747 | ADRB1 | Adrenergic, beta-1-, receptor |
| 17.36 | NM_015376 | RASGRP3 | RAS guanyl releasing protein 3 (calcium and DAG-regulated) |
| 16.84 | U62027 | C3AR1 | complement component 3a receptor 1 |
| 14.49 | AW025572 | HAVCR2 | hepatitis A virus cellular receptor 2 |
| 12.48 | AF285447 | HCST | hematopoietic cell signal transducer |
| 11.92 | AI805323 | LGR7 | leucine-rich repeat-containing G protein-coupled receptor 7 |
| 11.67 | NM_001197 | BIK | BCL2-interacting killer (apoptosis-inducing) |
| 11.53 | NM_018092 | NETO2 | neuropilin (NRP) and tolloid (TLL)-like 2 |
| 11.07 | N74607 | AQP3 | aquaporin 3 |
| 10.88 | BF439675 | CD69 | CD69 antigen (p60, early T-cell activation antigen) |
| 10.48 | NM_001769 | CD9 | CD9 antigen (p24) |
| 9.52 | AA814140 | C5orf18 | chromosome 5 open reading frame 18 |

TABLE 3-continued

| Fold Change | Genbank | Gene Symbol | Description |
|---|---|---|---|
| 8.77 | NM_005582 | CD180 | CD180 antigen |
| 7.46 | AF039686 | GPR34 | G protein-coupled receptor 34 |
| 7.30 | AI056776 | ITGA6 | Integrin, alpha 6 |
| 7.19 | AJ277151 | TNFRSF4 | tumor necrosis factor receptor superfamily, member 4 |
| 6.99 | AI738675 | SELPLG | Selectin P ligand |
| 6.85 | AA888858 | PDE3B | Phosphodiesterase 3B, cGMP-inhibited |
| 6.80 | AU149572 | ADCY2 | adenylate cyclase 2 (brain) |
| 6.80 | NM_002299 | LCT | lactase |
| 6.58 | NM_005296 | GPR23 | G protein-coupled receptor 23 |
| 6.45 | NM_004106 | FCER1G | Fc fragment of IgE, high affinity I, receptor for; gamma polypeptide |
| 6.25 | AW406569 | MGC15619 | hypothetical protein MGC15619 |
| 6.06 | M81695 | ITGAX | integrin, alpha X (antigen CD110 (p150), alpha polypeptide) |
| 5.92 | NM_003494 | DYSF | dysferlin, limb girdle muscular dystrophy 2B (autosomal recessive) |
| 5.85 | AI860212 | PAG1 | phosphoprotein associated with glycosphingolipid microdomains 1 |
| 5.75 | NM_013447 | EMR2 | egf-like module containing, mucin-like, hormone receptor-like 2 |
| 5.62 | NM_017806 | LIME1 | Lck interacting transmembrane adaptor 1 |
| 5.62 | AK092824 | AMN | Amnionless homolog (mouse) |
| 5.59 | AF345567 | GPR174 | G protein-coupled receptor 174 |
| 5.26 | L03419 | FCGR1A; LOC440607 | Fc fragment of IgG, high affinity Ia, receptor (CD64); Fc-gamma receptor I B2 |
| 5.24 | BG230586 | SLC7A6 | solute carrier family 7 (cationic amino acid transporter, y + system), member 6 |
| 5.18 | AF015524 | CCRL2 | chemokine (C-C motif) receptor-like 2 |
| 5.13 | AA631143 | SLC45A3 | solute carrier family 45, member 3 |
| 5.10 | AJ240085 | TRAT1 | T cell receptor associated transmembrane adaptor 1 |
| 5.05 | AW183080 | GPR92 | G protein-coupled receptor 92 |
| 5.03 | NM_002120 | HLA-DOB | major histocompatibility complex, class II, DO beta |
| 5.03 | NM_015364 | LY96 | lymphocyte antigen 96 |
| 4.90 | NM_020399 | GOPC | golgi associated PDZ and coiled-coil motif containing |
| 4.88 | AK026133 | SEMA4B | sema domain, immunoglobulin domain (Ig), transmembrane domain (TM) and short cytoplasmic domain, (semaphorin) 4B |
| 4.88 | BC041664 | VMD2 | vitelliform macular dystrophy 2 (Best disease, bestrophin) |
| 4.85 | NM_152592 | C14orf49 | chromosome 14 open reading frame 49 |
| 4.85 | AA923524 | RASGRP4 | RAS guanyl releasing protein 4 |
| 4.85 | B0008777 | ITGAL | integrin, alpha L (antigen CD11A (p180) |
| 4.67 | AF014403 | PPAP2A | phosphatidic acid phosphatase type 2A |
| 4.65 | AK097698 | SORCS2 | Sortilin-related VPS10 domain containing receptor 2 |
| 4.63 | X14355 | FCGR1A | Fc fragment of IgG, high affinity Ia, receptor (CD64) |
| 4.55 | NM_001629 | ALOX5AP | arachidonate 5-lipoxygenase-activating protein |
| 4.50 | AU155968 | C18orf1 | chromosome 18 open reading frame 1 |
| 4.44 | AK075092 | HERV-FRD | HERV-FRD provirus ancestral Env polyprotein |
| 4.42 | NM_020960 | GPR107 | G protein-coupled receptor 107 |
| 4.37 | BC000039 | FAM26B | family with sequence similarity 26, member B |
| 4.35 | NM_153701 | IL12RB1 | interleukin 12 receptor, beta 1 |
| 4.35 | AI762344 | PTGER1 | prostaglandin E receptor 1 (subtype EP1), 42 kDa |
| 4.31 | NM_006459 | SPFH1 | SPFH domain family, member 1 |
| 4.27 | NM_003126 | SPTA1 | spectrin, alpha, erythrocytic 1 (elliptocytosis 2) |
| 4.22 | AL518391 | AQP1 | aquaporin 1 (channel-forming integral protein, 28 kDa) |
| 4.12 | AK026188 | PCDHGC3 | protocadherin gamma subfamily C |
| 4.10 | AU146685 | EDG2 | Endothelial differentiation, lysophosphatidic acid G-protein-coupled receptor, 2 |
| 4.05 | BE673587 | SLC14A1 | Solute carrier family 14 (urea transporter), member 1 (Kidd blood group) |
| 4.02 | BF129969 | TSPAN2 | tetraspanin 2 |
| 4.00 | AW243272 | KCNK5 | Potassium channel, subfamily K, member 5 |
| 3.98 | T68858 | DHRS3 | Dehydrogenase/reductase (SDR family) member 3 |
| 3.94 | AI827849 | VTI1A | Vesicle transport through interaction with t-SNAREs homolog 1A (yeast) |
| 3.86 | AL134012 | NRXN2 | Neurexin 2 |
| 3.83 | BG230614 | CD47 | CD47 antigen (Rh-related antigen, integrin-associated signal transducer) |
| 3.80 | AI869717 | MGC15523 | hypothetical protein MGC15523 |
| 3.80 | AI458583 | SIMP | Source of immunodominant MHC-associated peptides |
| 3.79 | NM_002183 | IL3RA | interleukin 3 receptor, alpha (low affinity) |
| 3.79 | AA608820 | NRXN2 | neurexin 2 |

TABLE 3-continued

| Fold Change | Genbank | Gene Symbol | Description |
|---|---|---|---|
| 3.73 | NM_000206 | IL2RG | interleukin 2 receptor, gamma (severe combined immunodeficiency) |
| 3.72 | BC002737 | VAMP2 | vesicle-associated membrane protein 2 (synaptobrevin 2) |
| 3.72 | BC005884 | BID | BH3 interacting domain death agonist; BH3 interacting domain death agonist |
| 3.68 | AI688418 | PLXNA2 | plexin A2 |
| 3.68 | BC003105 | PTP4A3 | protein tyrosine phosphatase type IVA, member 3 |
| 3.68 | NM_001772 | CD33 | CD33 antigen (gp67) |
| 3.66 | AI955119 | VAMP2 | vesicle-associated membrane protein 2 (synaptobrevin 2) |
| 3.65 | B0007524 | SPAG9 | sperm associated antigen 9 |
| 3.64 | AI344200 | SLC25A35 | solute carrier family 25, member 35 |
| 3.64 | BC005253 | KLHL20 | kelch-like 20 (Drosophila) |
| 3.58 | BF381837 | C20orf52 | chromosome 20 open reading frame 52 |
| 3.51 | NM_002886 | RAP2A; RAP2B | RAP2A, member of RAS oncogene family; RAP2B, member of RAS oncogene family |
| 3.50 | NM_007063 | TBC1D8 | TBC1 domain family, member 8 (with GRAM domain) |
| 3.45 | AK027160 | BCL2L11 | BCL2-like 11 (apoptosis facilitator) |
| 3.44 | BF055366 | EDG2 | endothelial differentiation, lysophosphatidic acid G-protein-coupled receptor, 2 |
| 3.42 | NM_003608 | GPR65 | G protein-coupled receptor 65 |
| 3.41 | AI675453 | PLXNA3 | plexin A3 |
| 3.40 | AV734194 | DPP8 | dipeptidylpeptidase 8 |
| 3.36 | BC001956 | KIAA1961 | KIAA1961 gene |
| 3.34 | NM_013332 | HIG2 | hypoxia-inducible protein 2 |
| 3.31 | BC029450 | SLC33A1 | Solute carrier family 33 (acetyl-CoA transporter), member 1 |
| 3.28 | BF677986 | KIAA1961 | KIAA1961 gene |
| 3.27 | AI433691 | CACNA2D4 | calcium channel, voltage-dependent, alpha 2/delta subunit 4 |
| 3.26 | AB014573 | NPHP4 | nephronophthisis 4 |
| 3.25 | AL582804 | LY9 | lymphocyte antigen 9 |
| 3.25 | BG236280 | CD86 | CD86 antigen (CD28 antigen ligand 2, B7-2 antigen) |
| 3.24 | AA639289 | SLC26A7 | Solute carrier family 26, member 7 |
| 3.24 | NM_005211 | CSF1R | colony stimulating factor 1 receptor, formerly McDonough feline sarcoma viral (v-fms) oncogene homolog; colony stimulating factor 1 receptor, formerly McDonough feline sarcoma viral (v-fms) oncogene homolog |
| 3.24 | AI051254 | TRPM2 | transient receptor potential cation channel, subfamily M, member 2 |
| 3.23 | AW292816 | ABHD2 | abhydrolase domain containing 2 |
| 3.23 | B0040275 | RASGRF1 | Ras protein-specific guanine nucleotide-releasing factor 1 |
| 3.22 | NM_021911 | GABRB2 | gamma-aminobutyric acid (GABA) A receptor, beta 2 |
| 3.19 | AI660619 | SLC7A6 | solute carrier family 7 (cationic amino acid transporter, y + system), member 6 |
| 3.19 | NM_001860 | SLC31A2 | solute carrier family 31 (copper transporters), member 2 |
| 3.18 | NM_015680 | C2orf24 | chromosome 2 open reading frame 24 |
| 3.17 | AW058600 | SLC36A1 | solute carrier family 36 (proton/amino acid symporter), member 1 |
| 3.16 | AU145049 | HIP1 | Huntingtin interacting protein 1 |
| 3.15 | NM_005770 | SERF2 | small EDRK-rich factor 2 |
| 3.15 | NM_003566 | EEA1 | Early endosome antigen 1, 162 kD |
| 3.14 | NM_020041 | SLC2A9 | solute carrier family 2 (facilitated glucose transporter), member 9 |
| 3.14 | W90718 | SLC24A4 | solute carrier family 24 (sodium/potassium/calcium exchanger), member 4 |
| 3.13 | AI423165 | TICAM2 | toll-like receptor adaptor molecule 2 |
| 3.12 | AI674647 | SPPL2A | signal peptide peptidase-like 2A |
| 3.11 | NM_004121 | GGTLA1 | gamma-glutamyltransferase-like activity 1 |
| 3.10 | NM_004546 | NDUFB2 | NADH dehydrogenase (ubiquinone) 1 beta subcomplex, 2, 8 kDa |
| 3.05 | X15786 | RET | ret proto-oncogene (multiple endocrine neoplasia and medullary thyroid carcinoma 1, Hirschsprung disease) |
| 3.05 | AF181660 | MPZL1 | myelin protein zero-like 1 |
| 3.00 | AI571996 | STAM2 | signal transducing adaptor molecule (SH3 domain and ITAM motif) 2 |
| 2.99 | NM_000201 | ICAM1 | intercellular adhesion molecule 1 (CD54), human rhinovirus receptor |
| 2.93 | NM_025244 | TSGA10 | testis specific, 10 |
| 2.93 | AU147538 | PRKCE | Protein kinase C, epsilon |
| 2.92 | NM_024576 | OGFRL1 | opioid growth factor receptor-like 1 |

TABLE 3-continued

| Fold Change | Genbank | Gene Symbol | Description |
|---|---|---|---|
| 2.91 | AI248055 | ABCC4 | ATP-binding cassette, sub-family C (CFTR/MRP), member 4 |
| 2.86 | AA503877 | CEPT1 | Choline/ethanolamine phosphotransferase 1 |
| 2.84 | BC030993 | FLJ21127 | Hypothetical protein FLJ21127 |
| 2.82 | NM_001859 | SLC31A1 | solute carrier family 31 (copper transporters), member 1 |
| 2.81 | M74721 | CD79A | CD79A antigen (immunoglobulin-associated alpha) |
| 2.79 | AI986112 | MGAT4B | Mannosyl (alpha-1,3-)-glycoprotein beta-1,4-N-acetylglucosaminyltransferase, isoenzyme B |
| 2.79 | NM_030930 | UNC93B1 | unc-93 homolog B1 (C. elegans); unc-93 homolog B1 (C. elegans) |
| 2.79 | X74039 | PLAUR | plasminogen activator, urokinase receptor |
| 2.75 | BC005253 | KLHL20 | kelch-like 20 (Drosophila) |
| 2.73 | AB036432 | AGER | advanced glycosylation end product-specific receptor |
| 2.71 | NM_007245 | ATXN2L | ataxin 2-like |
| 2.71 | NM_016072 | GOLT1B | golgi transport 1 homolog B (S. cerevisiae) |
| 2.71 | AI453548 | ZDHHC8 | zinc finger, DHHC-type containing 8 |
| 2.70 | AI636233 | TMEM8 | transmembrane protein 8 (five membrane-spanning domains) |
| 2.69 | BE502509 | T3JAM | TRAF3 interacting protein 3 |
| 2.69 | AW117765 | PEX13 | peroxisome biogenesis factor 13 |
| 2.69 | AW052216 | IL17RB | Interleukin 17 receptor B |
| 2.67 | NM_003853 | IL18RAP | interleukin 18 receptor accessory protein |
| 2.66 | NM_002490 | NDUFA6 | NADH dehydrogenase (ubiquinone) 1 alpha subcomplex, 6, 14 kDa |
| 2.65 | NM_016639 | TNFRSF12A | tumor necrosis factor receptor superfamily, member 12A |
| 2.65 | AI363185 | FLJ20255 | Hypothetical protein FLJ20255 |
| 2.65 | NM_052931 | SLAMF6 | SLAM family member 6 |
| 2.65 | AW571669 | TNFRSF19L | tumor necrosis factor receptor superfamily, member 19-like |
| 2.64 | AA654142 | CEECAM1 | cerebral endothelial cell adhesion molecule 1 |
| 2.62 | AW510783 | TMEM63A | transmembrane protein 63A |
| 2.61 | W95007 | ACSL4 | Acyl-CoA synthetase long-chain family member 4 |
| 2.60 | S76475 | NTRK3 | neurotrophic tyrosine kinase, receptor, type 3 |
| 2.60 | AJ130713 | SIGLEC7 | sialic acid binding Ig-like lectin 7 |
| 2.56 | NM_003775 | EDG6 | endothelial differentiation, G-protein-coupled receptor 6 |
| 2.55 | AI978986 | MAMDC4 | MAM domain containing 4 |
| 2.54 | AF010447 | MR1 | major histocompatibility complex, class I-related |
| 2.54 | NM_006068 | TLR6 | toll-like receptor 6 |
| 2.53 | AF041811 | NTRK3 | neurotrophic tyrosine kinase, receptor, type 3 |
| 2.53 | AW953521 | SERF2; HYPK | small EDRK-rich factor 2; Huntingtin interacting protein K |
| 2.51 | AW293276 | CD53 | CD53 antigen |
| 2.49 | AK023058 | PLXNA2 | Plexin A2 |
| 2.49 | AI125204 | C6orf128 | chromosome 6 open reading frame 128 |
| 2.49 | NM_000392 | ABCC2 | ATP-binding cassette, sub-family C (CFTR/MRP), member 2 |
| 2.46 | BC032474 | TIRAP | toll-interleukin 1 receptor (TIR) domain containing adaptor protein |
| 2.44 | NM_031211 | IMAA; LOC388221; LOC440345; LOC440354; LOC595101; LOC641298 | SLC7A5 pseudogene; SLC7A5 pseudogene; NPIP-like locus; NPIP-like locus; hypothetical protein LOC440345; hypothetical protein LOC440345; PI-3-kinase-related kinase SMG-1 pseudogene; PI-3-kinase-related kinase SMG-1 pseudogene; PI-3-kinase-related kinase SMG-1 pseudogene; PI-3-kinase-related kinase SMG-1-like locus; PI-3-kinase-related kinase SMG-1-like locus |
| 2.44 | AI797836 | CD5 | CD5 antigen (p56-62) |
| 2.41 | W72082 | C1QR1 | complement component 1, q subcomponent, receptor 1; complement component 1, q subcomponent, receptor 1 |
| 2.40 | AA708616 | DPP9 | dipeptidylpeptidase 9 |
| 2.40 | BM987094 | DLGAP4 | discs, large (Drosophila) homolog-associated protein 4 |
| 2.40 | AL713719 | LOC283501 | ATPase, Class VI, type 11A |
| 2.39 | AI628734 | PRLR | prolactin receptor |
| 2.39 | NM_012110 | CHIC2 | cysteine-rich hydrophobic domain 2 |
| 2.38 | AK022002 | TFR2 | transferrin receptor 2 |
| 2.37 | NM_001555 | IGSF1 | immunoglobulin superfamily, member 1 |
| 2.36 | AA426091 | C19orf15 | chromosome 19 open reading frame 15 |
| 2.36 | BE547542 | GOPC | golgi associated PDZ and coiled-coil motif containing |
| 2.36 | NM_004231 | ATP6V1F | ATPase, H + transporting, lysosomal 14 kDa, V1 subunit F |

TABLE 3-continued

| Fold Change | Genbank | Gene Symbol | Description |
|---|---|---|---|
| 2.36 | AJ130712 | SIGLEC7 | sialic acid binding Ig-like lectin 7 |
| 2.36 | NM_017905 | TMCO3 | transmembrane and coiled-coil domains 3 |
| 2.35 | AB054985 | CACNB1 | calcium channel, voltage-dependent, beta 1 subunit |
| 2.35 | NM_005003 | NDUFAB1 | NADH dehydrogenase (ubiquinone) 1, alpha/beta subcomplex, 1, 8 kDa |
| 2.35 | NM_001251 | CD68 | CD68 antigen |
| 2.35 | AA700869 | PSCD2 | Pleckstrin homology, Sec7 and coiled-coil domains 2 (cytohesin-2) |
| 2.35 | U94903 | CD44 | CD44 antigen (homing function and Indian blood group system) |
| 2.35 | NM_003841 | TNFRSF10C | tumor necrosis factor receptor superfamily, member 10c, decoy without an intracellular domain |
| 2.33 | NM_004541 | NDUFA1 | NADH dehydrogenase (ubiquinone) 1 alpha subcomplex, 1, 7.5 kDa |
| 2.33 | BE567130 | KLRK1 | Killer cell lectin-like receptor subfamily K, member 1 |
| 2.31 | NM_017460 | CYP3A4 | cytochrome P450, family 3, subfamily A, polypeptide 4 |
| 2.31 | AI339536 | DSC1 | Desmocollin 1 |
| 2.31 | NM_001783 | CD79A | CD79A antigen (immunoglobulin-associated alpha); CD79A antigen (immunoglobulin-associated alpha) |
| 2.30 | AA333161 | VTI1A | vesicle transport through interaction with t-SNAREs homolog 1A (yeast) |
| 2.30 | AW134823 | CD6 | CD6 antigen; CD6 antigen |
| 2.30 | AL137537 | ATP8B2 | ATPase, Class I, type 8B, member 2 |
| 2.29 | AI671983 | SLC2A9 | solute carrier family 2 (facilitated glucose transporter), member 9 |
| 2.29 | AA018187 | C22orf3 | chromosome 22 open reading frame 3 |
| 2.29 | AL117415 | ADAM33 | ADAM metallopeptidase domain 33 |
| 2.29 | NM_002588 | PCDHGC3; PCDHGB4; PCDHGA8; PCDHGA12; PCDHGC5; PCDHGC4; PCDHGB7; PCDHGB6; PCDHGB5; PCDHGB3; PCDHGB2; PCDHGB1; PCDHGA11; PCDHGA10; PCDHGA9; PCDHGA7; PCDHGA6; PCDHGA5; PCDHGA4; PCDHGA3; PCDHGA2; PCDHGA1 | protocadherin gamma subfamily C, 3; protocadherin gamma subfamily B, 4; protocadherin gamma subfamily A, 8; protocadherin gamma subfamily A, 12; protocadherin gamma subfamily C, 5; protocadherin gamma subfamily C, 4; protocadherin gamma subfamily B, 7; protocadherin gamma subfamily B, 6; protocadherin gamma subfamily B, 5; protocadherin gamma subfamily B, 3; protocadherin gamma subfamily B, 2; protocadherin gamma subfamily B, 1; protocadherin gamma subfamily A, 11; protocadherin gamma subfamily A, 10; protocadherin gamma subfamily A, 9; protocadherin gamma subfamily A, 7; protocadherin gamma subfamily A, 6; protocadherin gamma subfamily A, 5; protocadherin gamma subfamily A, 4; protocadherin gamma subfamily A, 3; protocadherin gamma subfamily A, 2; protocadherin gamma subfamily A, 1 |
| 2.29 | NM_020960 | GPR107 | G protein-coupled receptor 107 |
| 2.29 | AK074635 | GENX-3414 | Genethonin 1 |
| 2.29 | BE138575 | ITGB5 | Integrin, beta 5 |
| 2.28 | NM_003830 | SIGLEC5 | sialic acid binding Ig-like lectin 5; sialic acid binding Ig-like lectin 5 |
| 2.28 | NM_013319 | UBIAD1 | UbiA prenyltransferase domain containing 1 |
| 2.28 | M63889 | FGFR1 | fibroblast growth factor receptor 1 (fms-related tyrosine kinase 2, Pfeiffer syndrome) |
| 2.27 | H67156 | MSCP | Solute carrier family 25, member 37 |
| 2.27 | BC006215 | SMEK2 | KIAA1387 protein; KIAA1387 protein |
| 2.27 | AL109653 | SLITRK2 | SLIT and NTRK-like family, member 2 |
| 2.27 | NM_007011 | ABHD2 | abhydrolase domain containing 2 |
| 2.26 | AI767210 | MGC11332 | Hypothetical protein MGC11332 |
| 2.26 | BF723605 | NRCAM | Neuronal cell adhesion molecule |
| 2.26 | R08129 | CDA08 | T-cell immunomodulatory protein |
| 2.26 | AF052059 | SEL1L | sel-1 suppressor of lin-12-like (C. elegans) |
| 2.26 | NM_005729 | PPIF | peptidylprolyl isomerase F (cyclophilin F) |
| 2.25 | BE858032 | ARL2L1 | ADP-ribosylation factor-like 2-like 1 |
| 2.25 | AI950390 | C14orf118 | Chromosome 14 open reading frame 118 |
| 2.24 | NM_017767 | SLC39A4 | solute carrier family 39 (zinc transporter), member 4 |
| 2.24 | AL110273 | SPTAN1 | Spectrin, alpha, non-erythrocytic 1 (alpha-fodrin) |
| 2.24 | AI077660 | CDA08 | T-cell immunomodulatory protein |
| 2.23 | AA488687 | SLC7A11 | solute carrier family 7, (cationic amino acid transporter, y + system) member 11 |
| 2.23 | NM_000634 | IL8RA | interleukin 8 receptor, alpha |
| 2.22 | AL390177 | MGC34032 | Solute carrier family 44, member 5 |

TABLE 3-continued

| Fold Change | Genbank | Gene Symbol | Description |
|---|---|---|---|
| 2.21 | NM_001531 | MR1 | major histocompatibility complex, class I-related |
| 2.21 | NM_003183 | ADAM17 | ADAM metallopeptidase domain 17 (tumor necrosis factor, alpha, converting enzyme) |
| 2.20 | AC003999 | SCAP2 | src family associated phosphoprotein 2 |
| 2.20 | BC014416 | SLC33A1 | solute carrier family 33 (acetyl-CoA transporter), member 1 |
| 2.20 | AF226731 | ADORA3 | adenosine A3 receptor |
| 2.19 | AI608725 | ICAM1 | intercellular adhesion molecule 1 (CD54), human rhinovirus receptor |
| 2.19 | U41163 | SLC6A8; FLJ43855 | solute carrier family 6 (neurotransmitter transporter, creatine), member 8; similar to sodium- and chloride-dependent creatine transporter |
| 2.19 | AU147799 | LRRC15 | leucine rich repeat containing 15 |
| 2.18 | AW337166 | LOC255104 | Transmembrane and coiled-coil domains 4 |
| 2.18 | NM_006505 | PVR | poliovirus receptor |
| 2.18 | AI638420 | CLIC4 | chloride intracellular channel 4 |
| 2.18 | AI167482 | SCUBE3 | Signal peptide, CUB domain, EGF-like 3 |
| 2.18 | AI739514 | HAS3 | hyaluronan synthase 3 |
| 2.18 | NM_005971 | FXYD3 | FXYD domain containing ion transport regulator 3 |
| 2.17 | AL022398 | TRAF3IP3 | TRAF3 interacting protein 3 |
| 2.17 | U90940 | FCGR2C | Fc fragment of IgG, low affinity IIc, receptor for (CD32) |
| 2.16 | B0023540 | SORCS1 | Sortilin-related VPS10 domain containing receptor 1 |
| 2.16 | AV713913 | OSTM1 | osteopetrosis associated transmembrane protein 1 |
| 2.15 | NM_024505 | NOX5 | NADPH oxidase, EF-hand calcium binding domain 5 |
| 2.15 | BC006178 | SEC22L3 | SEC22 vesicle trafficking protein-like 3 (S. cerevisiae); SEC22 vesicle trafficking protein-like 3 (S. cerevisiae) |
| 2.15 | BG151527 | GRIK5 | glutamate receptor, ionotropic, kainate 5 |
| 2.14 | AW001754 | NEGRI | neuronal growth regulator 1 |
| 2.14 | NM_013979 | BNIP1 | BCL2/adenovirus E1B 19 kDa interacting protein 1 |
| 2.14 | NM_018643 | TREM1 | triggering receptor expressed on myeloid cells 1 |
| 2.12 | NM_005284 | GPR6 | G protein-coupled receptor 6 |
| 2.11 | AA454190 | ZDHHC20 | zinc finger, DHHC-type containing 20 |
| 2.11 | AB048796 | TMPRSS13 | transmembrane protease, serine 13 |
| 2.11 | AL044520 | NYD-SP21 | testes development-related NYD-SP21 |
| 2.11 | BE463930 | TMAP1 | Matrix-remodelling associated 7 |
| 2.10 | NM_152264 | SLC39A13 | solute carrier family 39 (zinc transporter), member 13 |
| 2.08 | AL530874 | EPHB2 | EPH receptor B2 |
| 2.07 | NM_018668 | VPS33B | vacuolar protein sorting 33B (yeast) |
| 2.07 | NM_024531 | GPR172A | G protein-coupled receptor 172A |
| 2.07 | NM_023038 | ADAM19 | ADAM metallopeptidase domain 19 (meltrin beta) |
| 2.07 | BC001281 | TNFRSF10B | tumor necrosis factor receptor superfamily, member 10b |
| 2.07 | AF217749 | PCDHB9 | protocadherin beta 9 |
| 2.06 | AB030077 | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| 2.06 | AL137432 | SUSD1 | sushi domain containing 1 |
| 2.05 | NM_004518 | KCNQ2 | potassium voltage-gated channel, KQT-like subfamily, member 2 |
| 2.04 | AI672363 | VPS33B | vacuolar protein sorting 33B (yeast) |
| 2.04 | NM_006671 | SLC1A7 | solute carrier family 1 (glutamate transporter), member 7 |
| 2.03 | AA215519 | DLGAP1 | Discs, large (Drosophila) homolog-associated protein 1 |
| 2.02 | NM_004648 | PTPNS1 | protein tyrosine phosphatase, non-receptor type substrate 1 |
| 2.02 | NM_002564 | P2RY2 | purinergic receptor P2Y, G-protein coupled, 2 |
| 2.01 | BF511678 | SCUBE3 | Signal peptide, CUB domain, EGF-like 3 |
| 2.01 | BC013385 | CLEC7A | C-type lectin domain family 7, member A |

CD47 Facilitates Engraftment, Inhibits Phagocytosis, and is More Highly Expressed on AML LSC. It has long been recognized that the innate immune system, through natural killer (NK) effector cells, functions in the elimination of non-self and aberrant cells. NK cells eliminate target cells recognized by a variety of NK cell-activating receptors that bind ligands present on many normal cells; however, expression of self major histocompatibility complex (MHC) class I molecules can protect a cell by binding to NK inhibitory receptors.

These inhibitory receptors often contain immunoreceptor tyrosine-based inhibitory (ITIM) motifs that recruit and activate the SHP-1 and SHP-2 tyrosine phosphatases, which in turn inhibit signal transduction from the activating receptors. Accumulating evidence indicates that monocyte-derived effector cells, such as macrophages and dendritic cells, are also involved in the elimination of non-self and aberrant cells, mediated by a number of activating receptors. These effector cells also express the inhibitory receptor, signal regulatory protein alpha (SIRPα), which contains an ITIM motif able to recruit and activate the SHP-1 and SHP-2 phosphatases resulting in inhibition of phagocytosis. Several studies have identified CD47 as the ligand for SIRPα. CD47 is a widely expressed transmembrane protein, originally identified as integrin associated protein (IAP) due to its physical association with several integrins.

CD47 has been implicated in a number of processes including platelet activation, cell motility and adhesion, and leukocyte adhesion, migration, and phagocytosis. The CD47-SIRPα interaction has been implicated in the inhibition of phagocytosis from a number of studies. First, CD47-deficient, but not wild type, mouse red blood cells (RBCs) were rapidly cleared from the bloodstream by splenic macrophages when transfused into wild type mice, and this effect was dependent on the CD47-SIRPαinteraction. CD47-deficient, but not wild type, lymphocytes and bone marrow cells were also rapidly cleared upon transplantation into congenic wild type recipients through macrophage and dendritic cell-mediated phagocytosis. Additional evidence suggested that the CD47-SIRPα interaction can inhibit phagocytosis stimulated by the recognition of IgG or complement opsonized cells. Thus, CD47 functions as a critical regulator of macrophage and dendritic cell phagocytosis by binding to SIRPα and delivering a dominant inhibitory signal.

Figure 9:
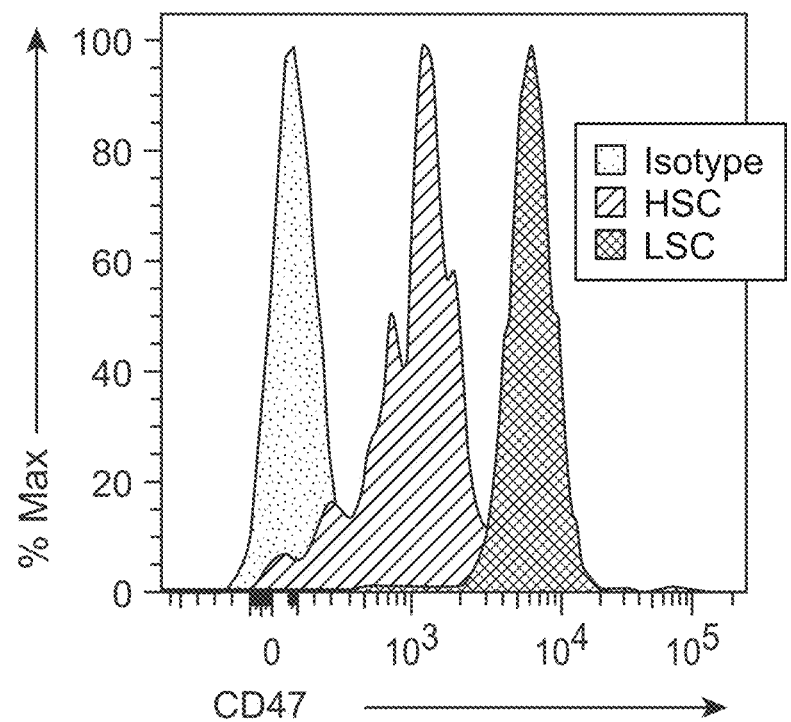
FIG. 9. CD47 is more highly expressed on AML LSC. Mobilized peripheral blood (MPB) HSC and AML LSC were examined for CD47 expression by flow cytometry. (A) Representative flow cytometry plots indicating expression of CD47 relative to an isotype control. (B) Summary of CD47 expression on all samples assayed, with the indicated means.
Figure 9:
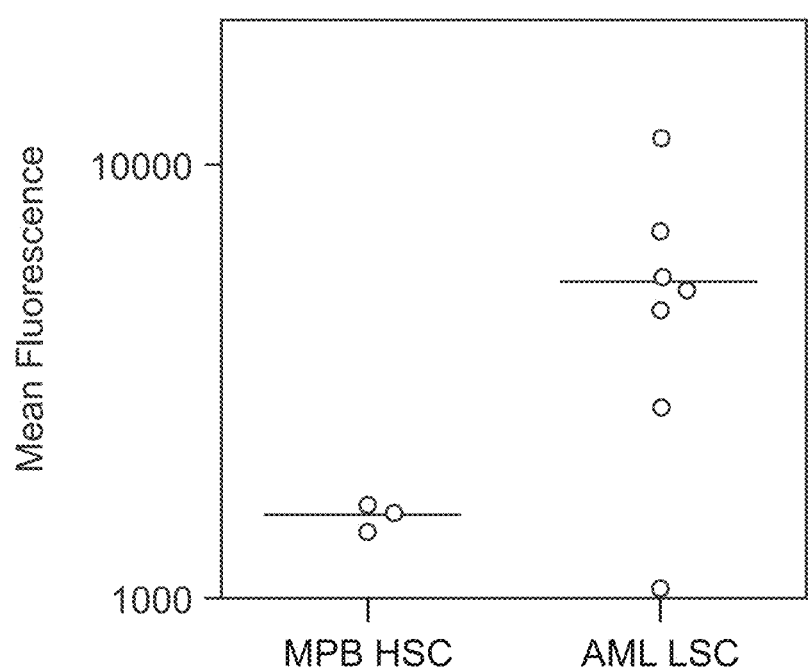

We determined expression of CD47 on human AML LSC and normal HSC by flow cytometry. HSC (Lin−CD34+CD38−CD90+) from three samples of normal human mobilized peripheral blood and AML LSC (Lin−CD34+CD38−CD90−) from seven samples of human AML were analyzed for surface expression of CD47 (FIG. 9). CD47 was expressed at low levels on the surface of normal HSC; however, on average, it was approximately 5-fold more highly expressed on AML LSC, as well as bulk leukemic blasts.

Figure 10:
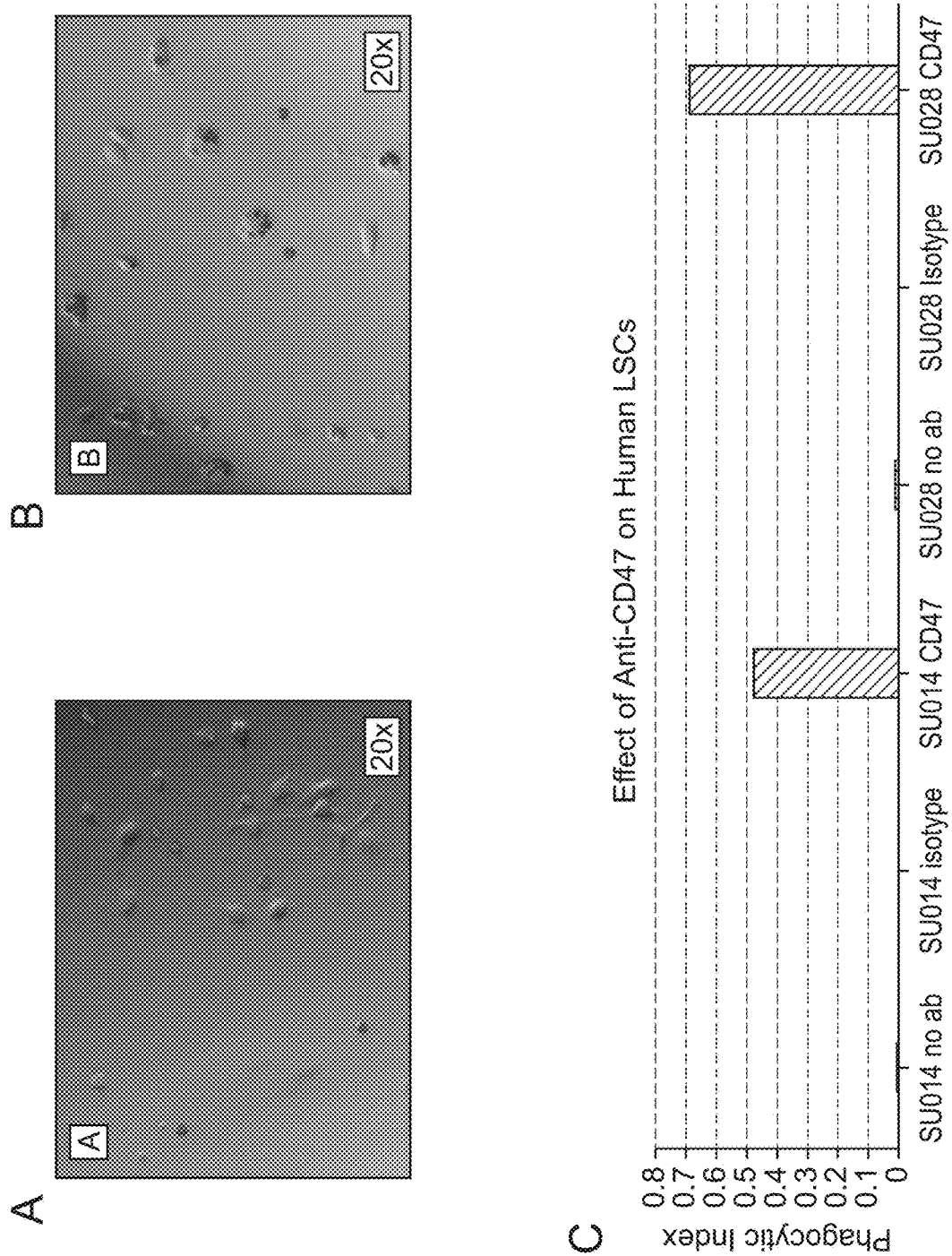
FIG. 10: Anti-CD47 Antibody Stimulates In Vitro Macrophage Phagocytosis of Primary Human AML LSC. AML LSC were purified by FACS from two primary human AML samples, labeled with the fluorescent dye CFSE, and incubated with mouse bone marrow-derived macrophages either in the presence of an isotype control (A) or anti-CD47 antibody (B). These cells were assessed by immunofluorescence microscopy for the presence of fluorescently labeled LSC within the macrophages. (C) The phagocytic index was determined for each condition by calculating the number of ingested cells per 100 macrophages.
Figure 11:
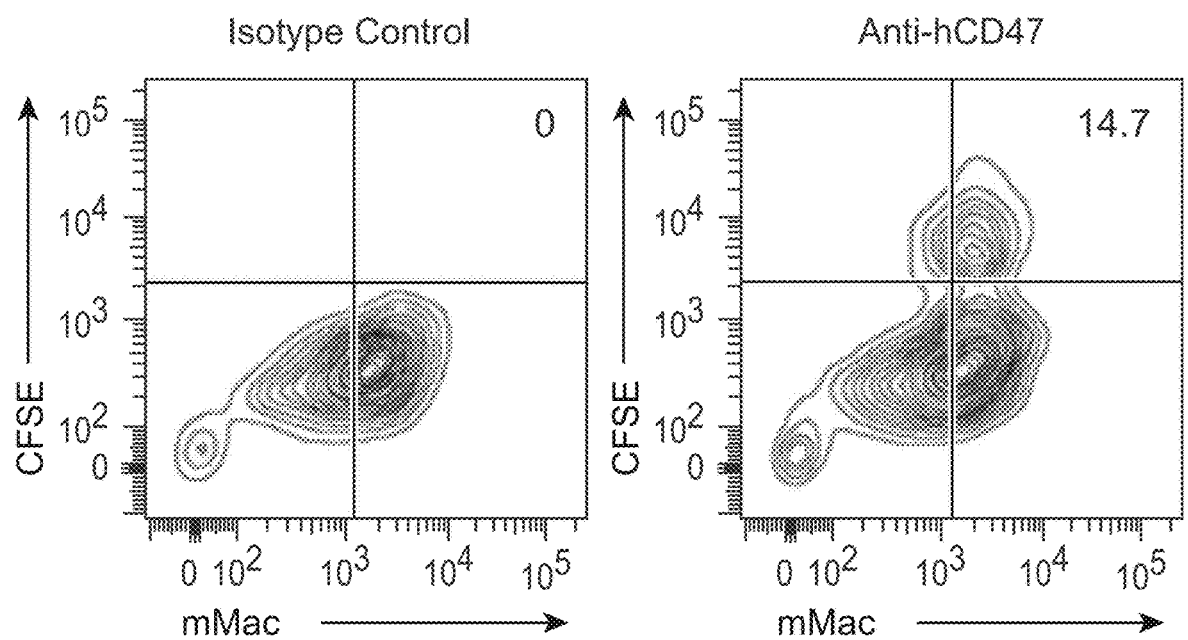
FIG. 11. Anti-CD47 antibody stimulates in vitro macrophage phagocytosis of primary human AML LSC. AML LSC were purified by FACS from two primary human AML samples and labeled with the fluorescent dye CFSE. These cells were incubated with mouse bone marrow-derived macrophages, either in the presence of an isotype matched control (left) or anti-CD47 antibody (right). The macrophages were harvested, stained with a fluorescently labeled anti-mouse macrophage antibody, and analyzed by flow cytometry. mMac+CFSE+ double-positive events identify macrophages that have phagocytosed CFSE-labeled LSC. (A,B) two independent primary AML LSC samples.
Figure 11:
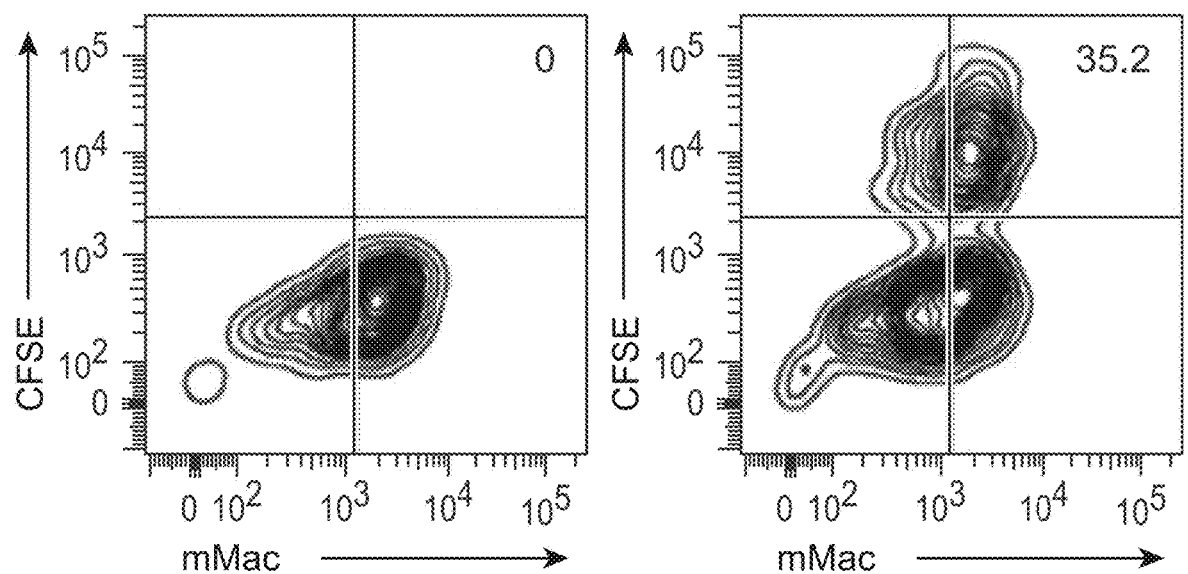

Anti-Human CD47 Monoclonal Antibody Stimulates Phagocytosis and Inhibits Engraftment of AML LSC. In order to test the model that CD47 overexpression on AML LSC prevents phagocytosis of these cells through its interaction with SIRPα on effector cells, we have utilized a monoclonal antibody directed against CD47 known to disrupt the CD47-SIRPα interaction. The hybridoma producing a mouse-anti-human CD47 monoclonal antibody, termed B6H12, was obtained from ATCC and used to produce purified antibody. First, we conducted in vitro phagocytosis assays. Primary human AML LSC were purified by FACS from two samples of human AML, and then loaded with the fluorescent dye CFSE. These cells were incubated with mouse bone marrow-derived macrophages and monitored using immunofluorescence microscopy (FIG. 10) and flow cytometry (FIG. 11) to identify phagocytosed cells. In both cases, no phagocytosis was observed in the presence of an isotype control antibody; however, significant phagocytosis was detected with the addition of the anti-CD47 antibody. Thus, blockage of human CD47 with a monoclonal antibody is capable of stimulating the phagocytosis of these cells by mouse macrophages.

Figure 12:
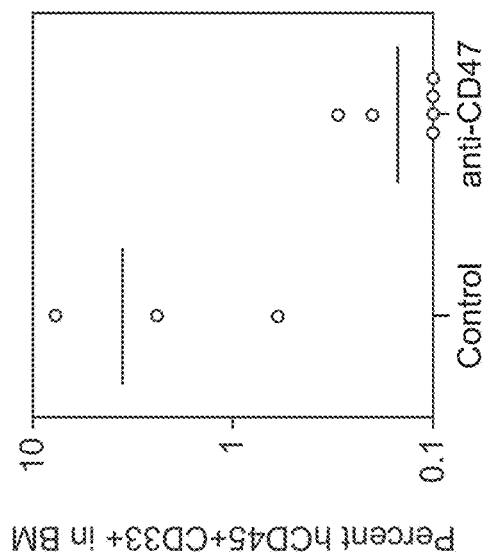
FIG. 12. Anti-CD47 antibody inhibits in vivo engraftment of primary human AML. Two primary human AML samples were untreated (control, n=3) or coated with anti-human CD47 antibody (anti-CD47, n=6) prior to transplantation into newborn NOG mice. 13 weeks later, mice were sacrificed and the bone marrow was analyzed for the presence of human CD45+CD33+ myeloid leukemia cells by flow cytometry.

We next investigated the ability of the anti-CD47 antibody to inhibit AML LSC engraftment in vivo. Two primary human AML samples were either untreated or coated with the anti-CD47 antibody prior to transplantation into NOG newborn mice. 13 weeks later, the mice were sacrificed and analyzed for human leukemia bone marrow engraftment by flow cytometry (FIG. 12). The control mice demonstrated leukemic engraftment while mice transplanted with the anti-CD47-coated cells showed little to no engraftment. These data indicate that blockade of human CD47 with a monoclonal antibody is able to inhibit AML LSC engraftment.

CD96 is a Human Acute Myeloid Leukemia Stem Cell-Specific Cell Surface Molecule. CD96, originally termed Tactile, was first identified as a T cell surface molecule that is highly upregulated upon T cell activation. CD96 is expressed at low levels on resting T and NK cells and is strongly upregulated upon stimulation in both cell types. It is not expressed on other hematopoietic cells, and examination of its expression pattern showed that it is only otherwise present on some intestinal epithelia. The cytoplasmic domain of CD96 contains a putative ITIM motif, but it is not known if this functions in signal transduction. CD96 promotes adhesion of NK cells to target cells expressing CD155, resulting in stimulation of cytotoxicity of activated NK cells.

Preferential Cell Surface Expression of Molecules Identified from Gene Expression Analysis. Beyond CD47 and CD96, several of the molecules listed in FIG. 8B are known to be expressed on AML LSC, including: CD123, CD44, and CD33. The remaining molecules have not been previously reported or identified as preferentially expressed on human AML LSC compared to their normal counterparts. We have examined cell surface expression of two of these molecules by flow cytometry to determine if there is preferential expression on AML LSC compared to normal HSC.

Figure 13:
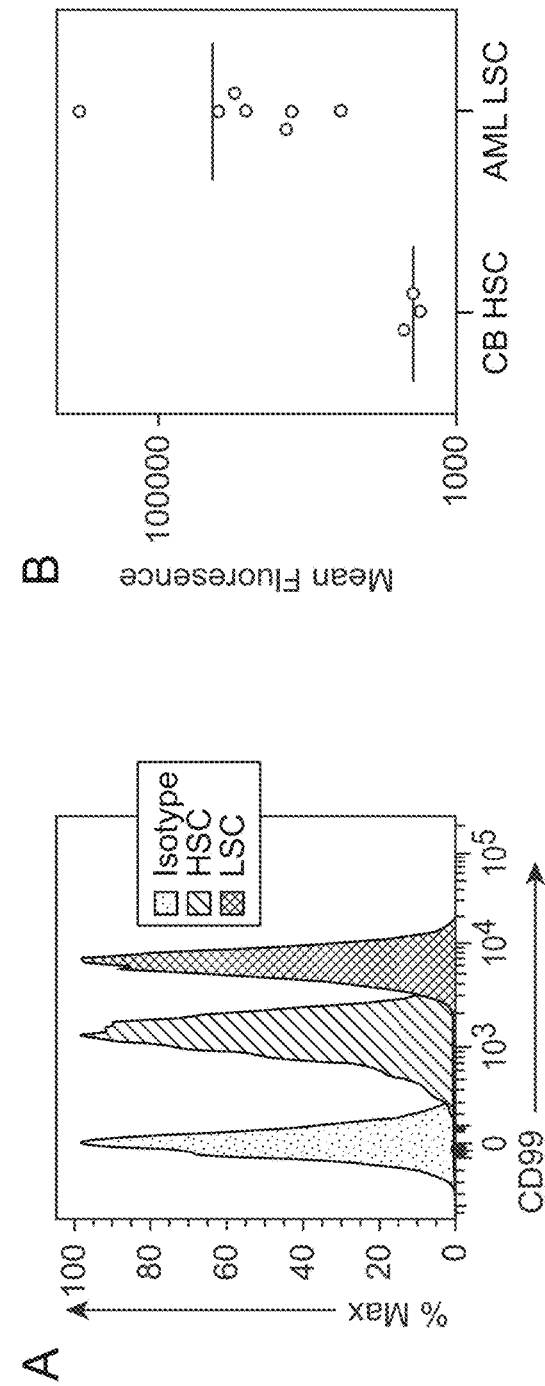
FIG. 13. CD99 is highly expressed on AML LSC. Cord blood (CB) HSC and AML LSC were examined for CD99 expression by flow cytometry. (A) representative flow cytometry plots indicating expression of CD99 relative to an isotype matched control. (B) summary of CD99 expression on all samples assayed.
Figure 14:
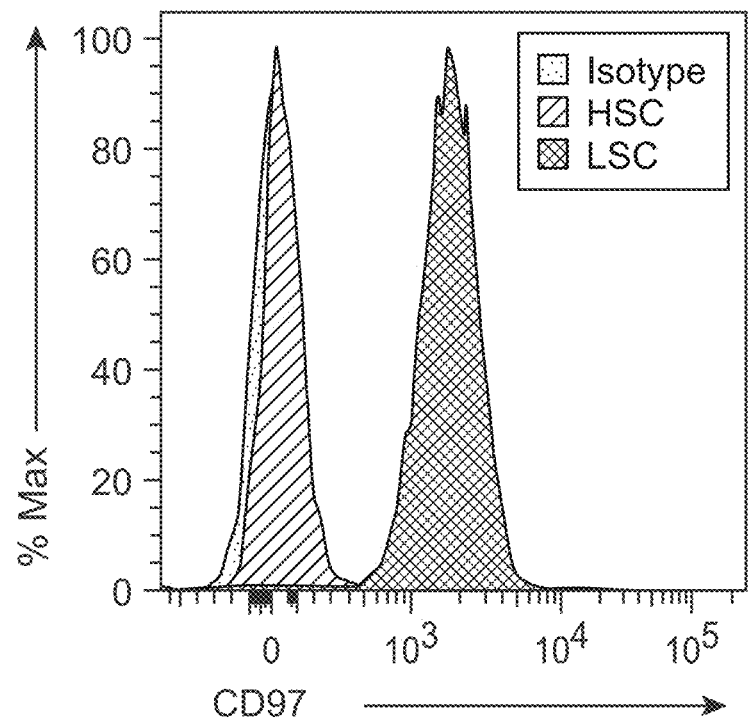
FIG. 14. CD97 is preferentially expressed on LSC. Cord blood HSC (Lin−CD34+CD38− CD90+, n=3) and AML LSC (Lin−CD34+CD38−CD90+, n=7) were examined for CD97 expression by flow cytometry. (A) representative flow cytometry plots indicating expression of CD97 relative to an isotype matched control. (B) Summary of CD97 expression on all samples assayed.
Figure 14:
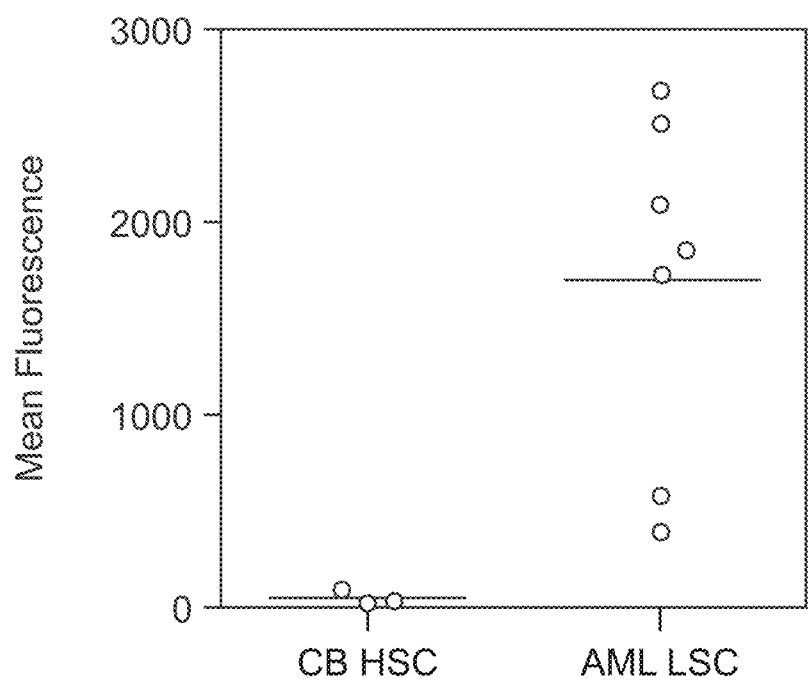

CD99 is a surface glycoprotein with highest expression on T cells where it may function in cellular adhesion. CD99 expression on HSC (Lin−CD34+CD38−CD90+) from three samples of normal human cord blood and AML LSC (Lin−CD34+CD38−CD90−) from seven samples of human AML was determined by flow cytometry (FIG. 13). CD99 was expressed at low levels on the surface of normal HSC; however, on average, it is approximately 5-fold more highly expressed on AML LSC. CD97 is normally expressed on most mature hematopoietic cells and is upregulated on activated lymphocytes where it may function in cellular migration and adhesion. Gene expression profiling indicates low to absent expression of CD97 in HSC and MPP, with approximately 10-fold higher expression in AML LSC. CD97 expression on normal cord blood HSC and AML LSC was examined by flow cytometry and found to be absent on HSC and high on 5 out of 7 AML LSC samples (FIG. 14).

In order to evaluate the other candidate genes in FIG. 8B, we screened this list for those molecules not likely to be expressed on normal HSC based on raw array expression values. Next, using published reports, we investigated the tissue expression pattern of these genes, in order to identify those with very restricted patterns of expression for which monoclonal antibodies would have few targets besides the leukemia cells. Based on these methods, two promising genes were identified: Parathyroid Hormone Receptor 2 and Hepatitis A Virus Cellular Receptor 2 (also known as TIM-3: T cell immunoglobulin mucin 3). Parathyroid Hormone Receptor 2 (PTHR2) is normally expressed in the pancreas and in some areas of the central nervous system. Its primary ligand is a peptide termed tuberoinfundibular peptide 39 (TIP39). Hepatitis A Virus Cellular Receptor 2 (HAVCR2) is normally expressed on a subset of T lymphocytes. Its primary ligand is a molecule named Galectin-9.

Validation of additional sequences may utilize specific antibodies and testing by flow cytometry, with comparison to normal HSC.

Example 3

Human and Mouse Leukaemias Upregulate CD47 to Evade Macrophage Killing

Tumour progression is characterized by several hallmarks, including growth signal independence, inhibition of apoptosis, and evasion of the immune system, among others. We show here that expression of CD47, a ligand for the macrophage inhibitory signal regulatory protein alpha (SIRPα) receptor, is increased in human and mouse myeloid leukaemia and allows cells to evade phagocytosis and increase their tumorigenic potential. CD47, also known as integrin associated protein (IAP), is an immunoglobulin-like transmembrane pentaspanin that is broadly expressed in mammalian tissues. We provide evidence that CD47 is upregulated in mouse and human myeloid leukaemia stem and progenitor cells, as well as leukemic blasts. Consistent with a biological role for CD47 in myeloid leukaemia development and maintenance, we demonstrate that ectopic over-expression of CD47 allows a myeloid leukaemia cell line to grow in mice that are T, B, and NK-cell deficient, whereas it is otherwise cleared rapidly when transplanted into these recipients. The leukemogenic potential of CD47 is also shown to be dose-dependent, as higher expressing clones have greater tumor forming potential than lower expressing clones. We also show that CD47 functions in promoting leukemogenesis by inhibiting phagocytosis of the leukemic cells by macrophages.

Figure 15:
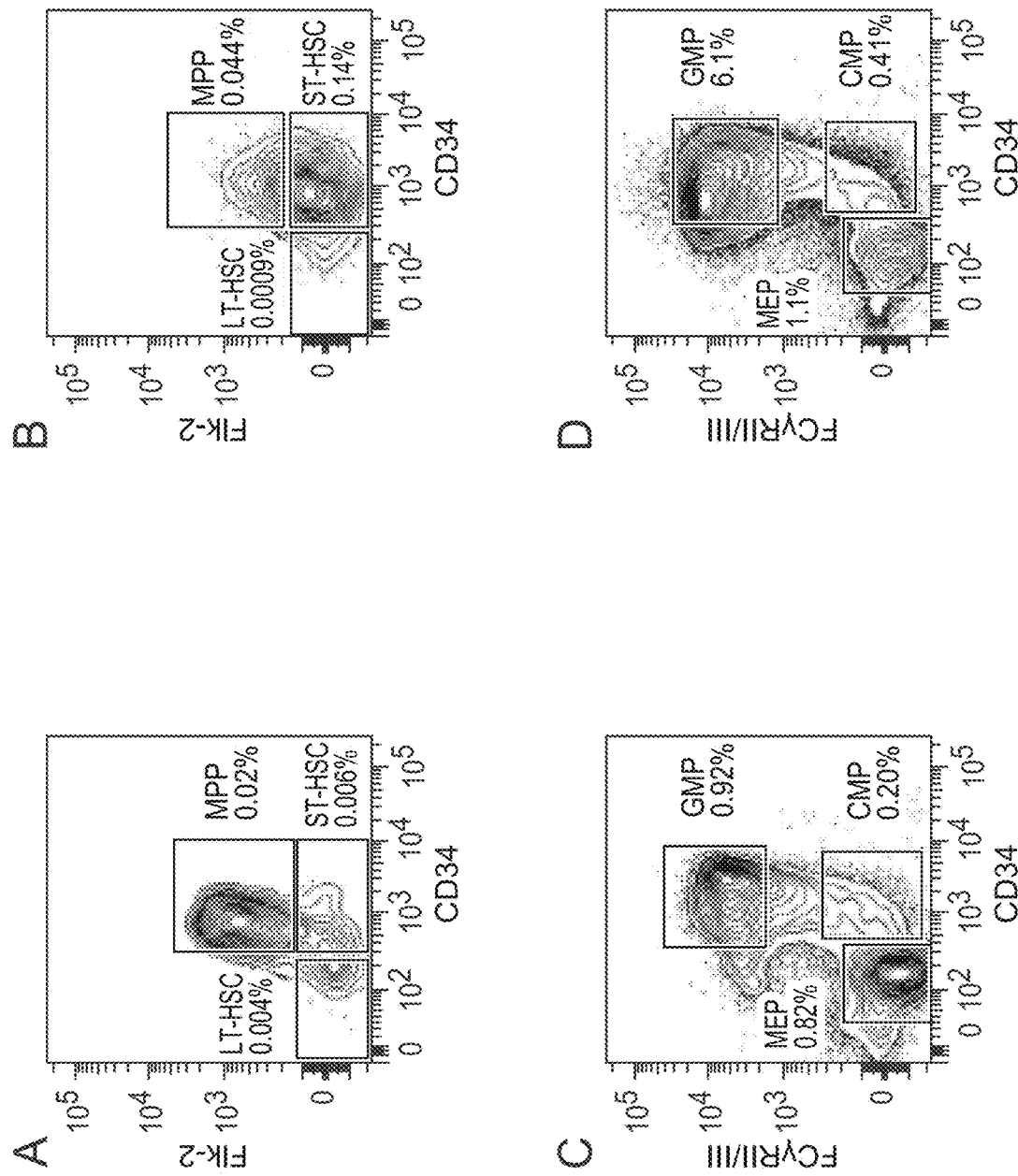
FIG. 15. CD47 is upregulated in murine acute myeloid leukemia. Typical stem and progenitor plots are shown for leukemic hMRP8bcrabl×hMRP8bcl2 cells compared to control non-leukemic animals. Lin− c-Kit+ Sca-1+ gated cells from control bone marrow (a) and leukemic spleen (b) and Lin− c-Kit+ Sca-1− gated cells from control bone marrow (c) and leukemic spleen (d) demonstrate perturbances in normal haematopoiesis in leukemic mice. Frequency is shown as a percentage of entire marrow or spleen mononuclear fraction. (e) Quantitative RT-PCR shows that CD47 is upregulated in leukemic BM cells. Data are shown from 3 sets of mice transplanted with either leukemic or control hRMP8bcrabl×hMRP8bcl2 BM cells and then sacrificed 2-6 weeks later. Results were normalized to beta-actin and 18S rRNA expression. Fold change relative to control transplanted whole Bcl-2+ BM cells was determined. Error bars represent 1 s.d. (f) Histograms show expression of CD47 on gated populations for leukemic (gray) and control (black) mice.
Figure 15:
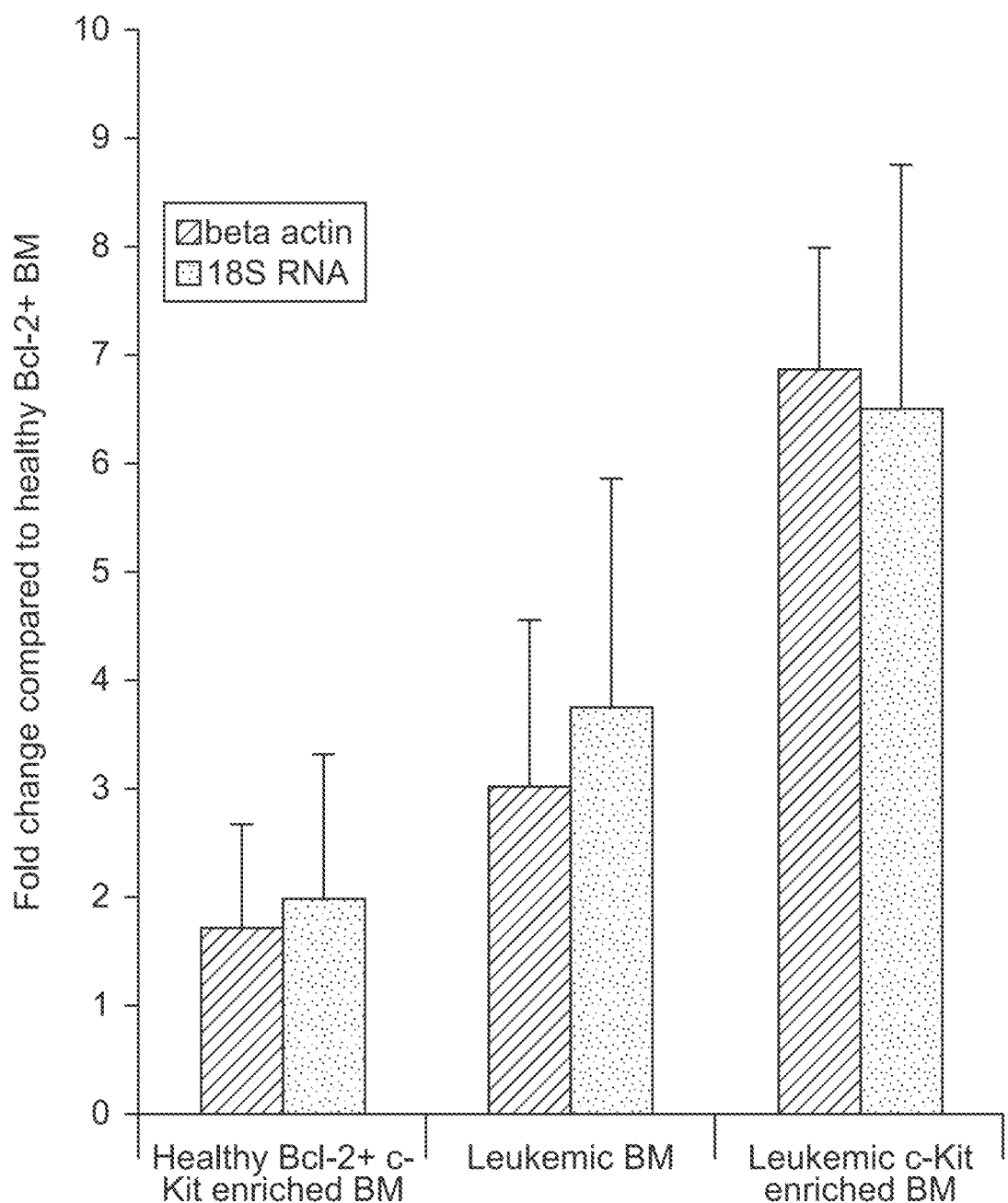

CD47 is significantly upregulated in leukemic $Fas^{lpr/lpr} \times$ hMRP8bcl2 transgenic bone marrow, and in leukemic hMRP8bcr/abl×hMRP8bcl2 mice. Transcripts for CD47 are increased in leukemic hMRP8bcr/abl×hMRP8bcl2 bone marrow 3-4 fold by quantitative RT-PCR and 6-7 fold in c-Kit enriched leukemic marrow relative to healthy hMRP8bcl2+ bone marrow (FIG. 15e). Leukemic spleen had an expansion of the granulocyte macrophage progenitor (GMP) population as well as c-Kit+ Sca-1+ Lin-stem and progenitor subsets relative to control mice, which were of the same genotype as leukemic mice but failed to develop disease (FIGS. 15a-d). Expression levels for CD47 protein were found to begin increasing in leukemic mice relative to control mice at the stage of the Flk2− CD34− c-Kit+Sca-1+Lin− long-term haematopoietic stem cell (LT-HSC) (FIG. 15f). This increased level of expression was maintained in GMP and Mac-1+ blasts, but not megakaryocyte/erythroid restricted progenitors (MEP)(FIG. 15f). The increase in CD47 between leukemic and normal cells was between 3 to 20 fold. All mice that developed leukaemia that we have examined from hMRP8bcr/abl×hMRP8bcl2 primary (n=3) and secondary transplanted mice (n=3), $Fas^{lpr/lpr} \times$ hMRP8bcl2 primary (n=14) and secondary (n=19) mice, and hMRP8bcl2×hMRP8bcl2 primary (n=3) and secondary (n=12) mice had increased CD47 expression. We have also found increased CD47 expression in mice that received p210bcr/abl retrovirally-transduced mouse bone marrow cells that developed leukaemia.

Figure 16:
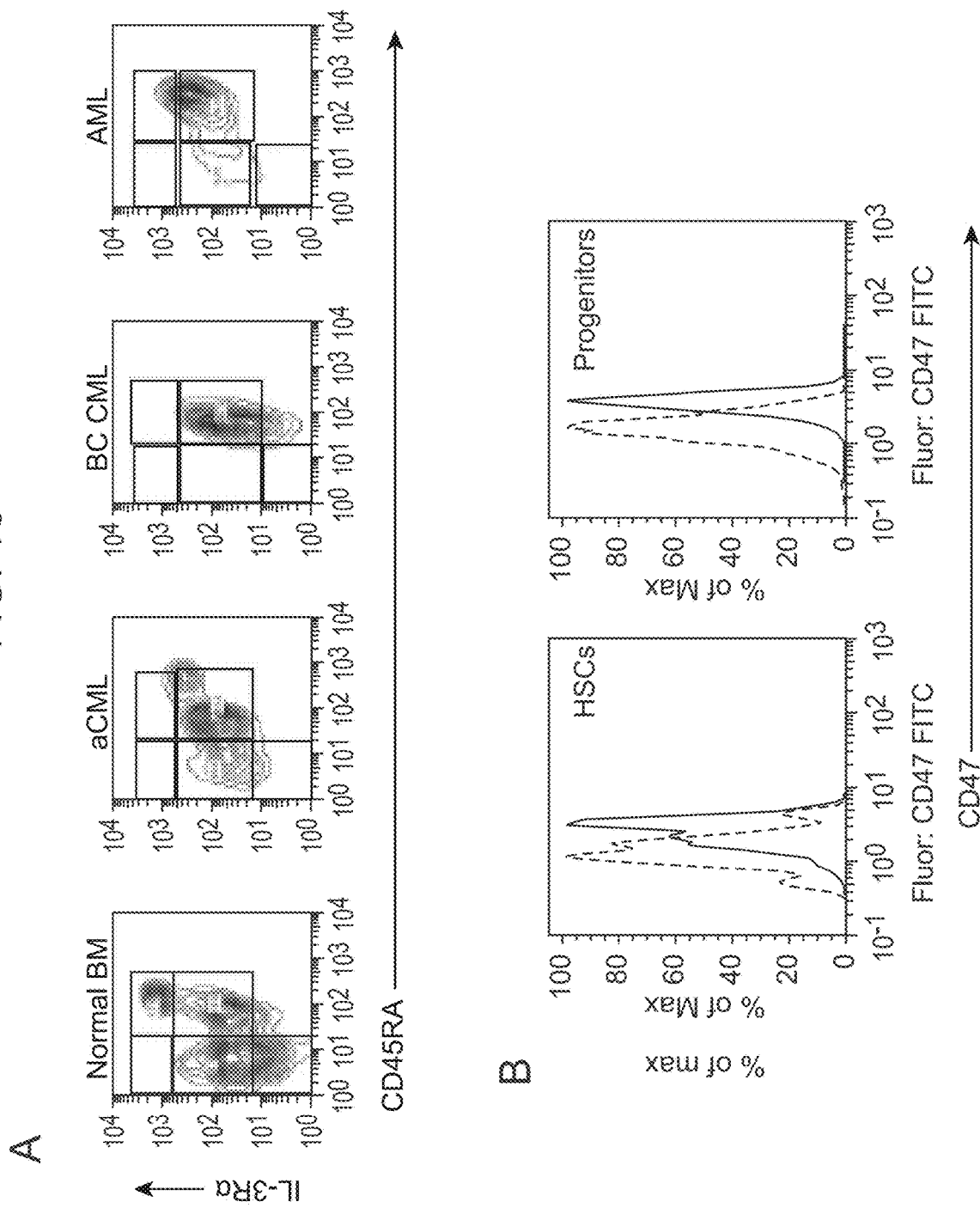
FIG. 16. GMP expansion and CD47 upregulation in human myeloid leukemia. a) Representative FACS plots of myeloid progenitors (CD34+CD38+Lin−) including common myeloid progenitors (CMP), megakaryocyte-erythroid progenitors (MEP) and granulocyte-macrophage progenitors (GMP) in normal bone marrow (BM) versus aCML, BC CML and AML. b) Comparative FACS histograms of CD47 expression by normal (red; n=6) and acute myelogenous leukemic (AML, blue; n=6) haematopoietic stem cells (HSC; CD34+CD38−CD90+Lin−) and progenitors (CD34+ CD38+Lin−). c) Comparative FACS histograms of CD47 expression by normal (red) and chronic myelogenous leukemia haematopoietic stem cells (HSC; CD34+CD38−CD90+Lin) and committed progenitors (CD34+CD38+Lin−). Upper panel: Normal (n=7) versus chronic phase CML (n=4) HSC, progenitors and lineage positive cells. Middle panel: Normal (n=7) versus accelerated phase CML (n=7) HSC, progenitors and lineage positive cells. Lower panel: Normal (n=7) versus blast crisis CML (n=4) HSC, progenitors and lineage positive cells.
Figure 16:
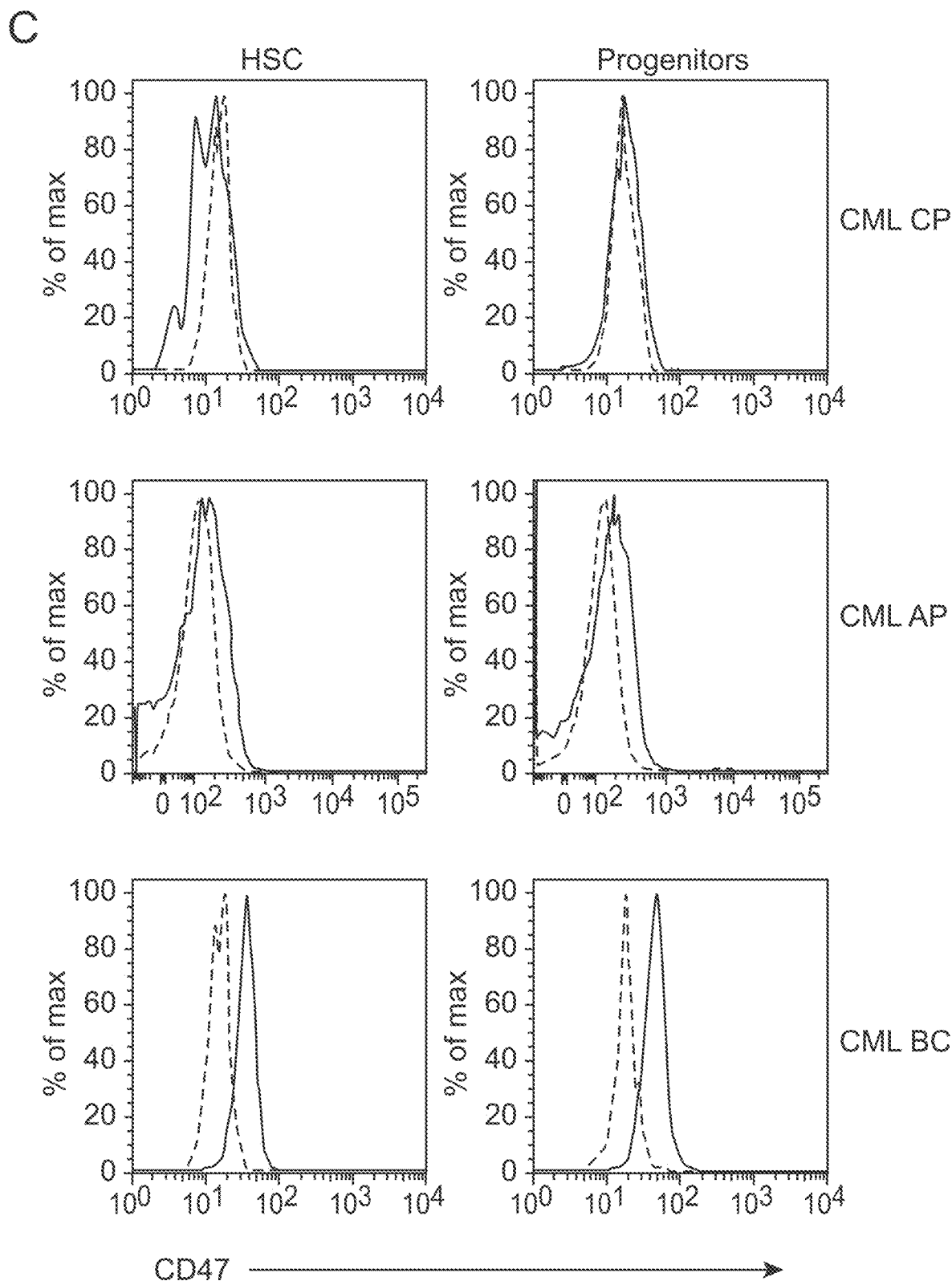
Figure 16:
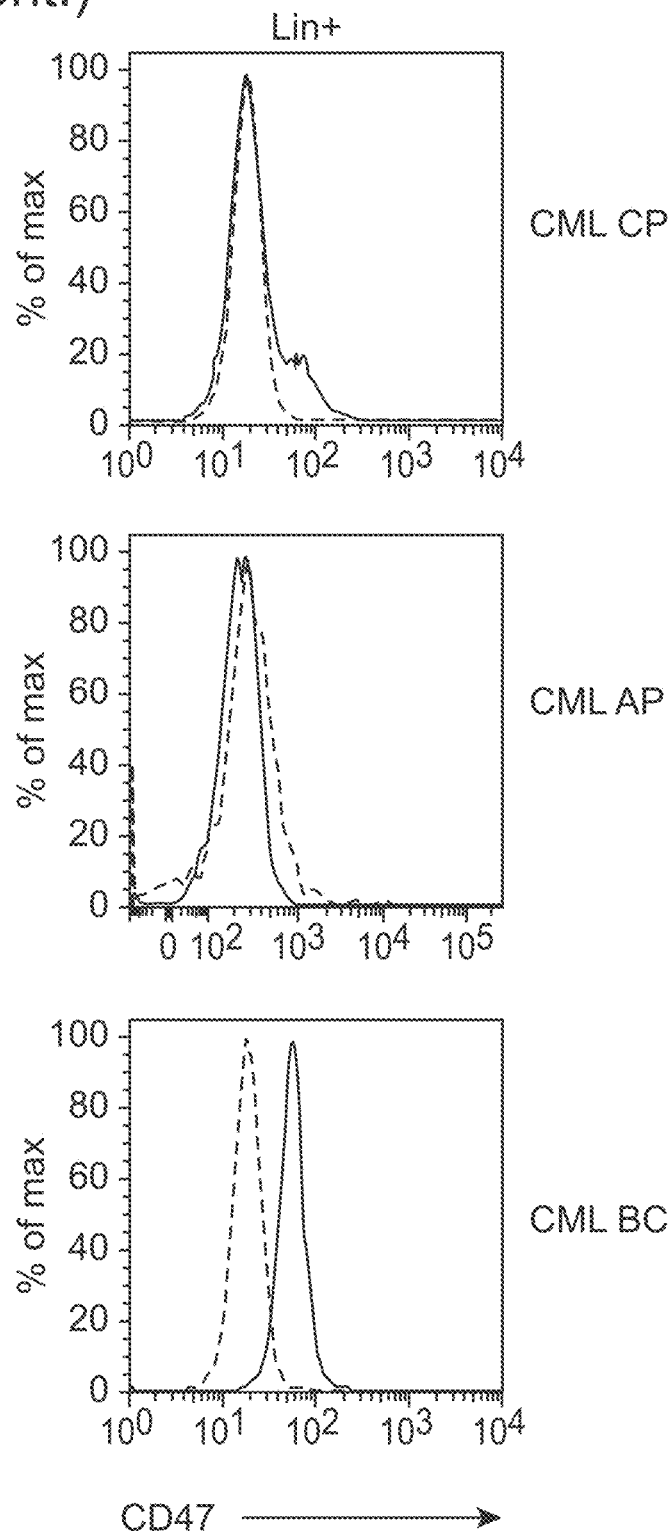

FACS-mediated analysis of human haematopoietic progenitor populations was performed on blood and marrow derived from normal cord blood and mobilized peripheral blood (n=16) and myeloproliferative disorders (MPDs) including polycythemia vera (PV; n=16), myelofibrosis (MF; n=5), essential thrombocythemia (ET; n=7), chronic myelomonocytic leukaemia (CMML; n=11) and atypical chronic myeloid leukaemia (aCML; n=1) as well as blast crisis phase chronic myeloid leukaemia (CML; n=19), chronic phase CML (n=7) and acute myelogenous leukaemia (AML; n=13). This analysis demonstrated that granulocyte-macrophage progenitors (GMP) expanded in MPDs with myeloid skewed differentiation potential including atypical CML, proliferative phase CMML and acute leukaemia including blast crisis CML and AML (FIG. 16a). AML HSC and progenitors uniformly exhibited higher levels of CD47 expression compared with normal controls (FIG. 16b); every sample from BC-CML and AML had elevated levels of CD47. Moreover, progression from chronic phase CML to blast crisis was associated with a significant increase in CD47 expression (FIG. 16c). Using the methods described in this study, we have found that human CD47 protein expression in CML-BC increased 2.2 fold in CD90+ CD34+ CD38− Lin− cells relative to normal (p=6.3×10$^{-5}$), 2.3 fold in CD90− CD34+ CD38− Lin− cells relative to normal (p=4.3×10$^{-5}$), and 2.4 fold in CD 34+ CD38+ Lin− cells (p=7.6×10$^{-6}$) (FIGS. 16b-16c); however, using a newer optimized staining protocol we have observed that CD47 is increased approximately 10 fold in AML and BC-CML compared to normal human HSCs and progenitors.

Figure 17:
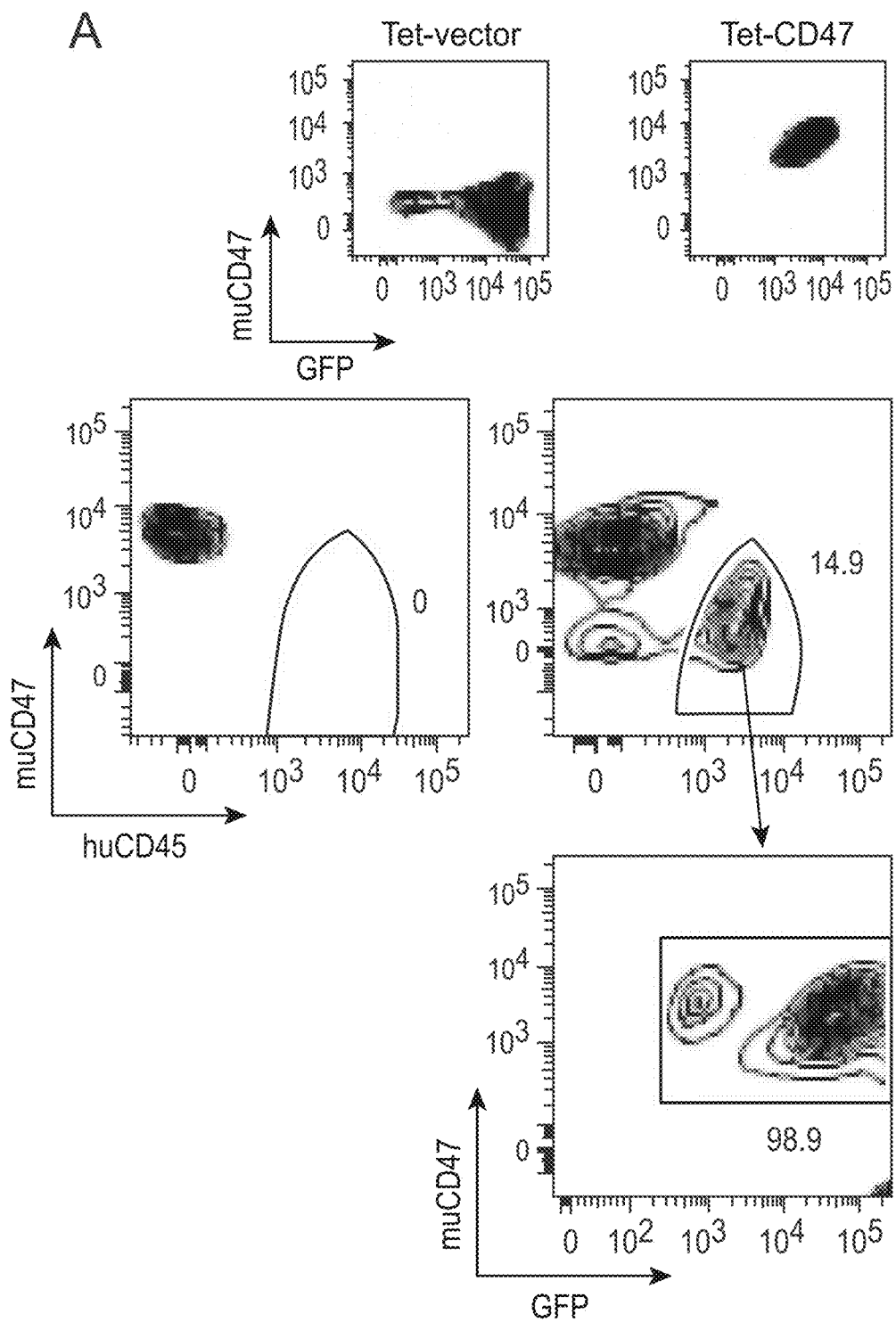
FIG. 17. Over-expression of murine CD47 increases tumorigenicity of MOLM-13 cells. a) MOLM-13 cells were transduced with either control virus or virus expressing murine CD47 cDNA form 2. The resulting cell lines, termed Tet or Tet-CD47, were transplanted competitively into RAG/common gamma chain deficient mice with untransduced MOLM-13 cells ($5 \times 10^5$ Tet (n=6) or Tet-47 (n=8) cells with $5 \times 10^5$ MOLM-13). Mice were analyzed for GFP and human CD45 chimerism when moribund. b) MOLM-13 chimerism in haematopoietic tissues was determined by human CD45 chimerism and measurement of tumour lesion size. c) Survival of mice competitively transplanted with MOLM-13 plus Tet or Tet-CD47 MOLM-13 cells was plotted. Control mice died of large tumour burden at the site of injection but had no engraftment in haematopoietic tissues. d) Hematoxylin and eosin sections of Tet-CD47 MOLM-13 transplanted liver (200×). Periportal (arrow) and sinusoidal (arrowhead) tumor infiltration is evident. e) $1 \times 10^6$ Tet (n=5) or Tet-CD47 MOLM-13 (n=4) cells were injected into the right femur of RAG2−/−, Gc−/− mice and the tissues were analyzed 50-75 days later and chimerism of MOLM-13 cells in bone marrow was determined. f) Survival curve of mice transplanted intrafemorally with Tet or Tet-CD47 MOLM-13 cells. g) Examples of liver tumour formation and hepatomegaly in Tet-CD47 MOLM-13 transplanted mice versus control transplanted mice. GFP fluorescence demonstrates tumour nodule formation as well diffuse infiltration.
Figure 17:
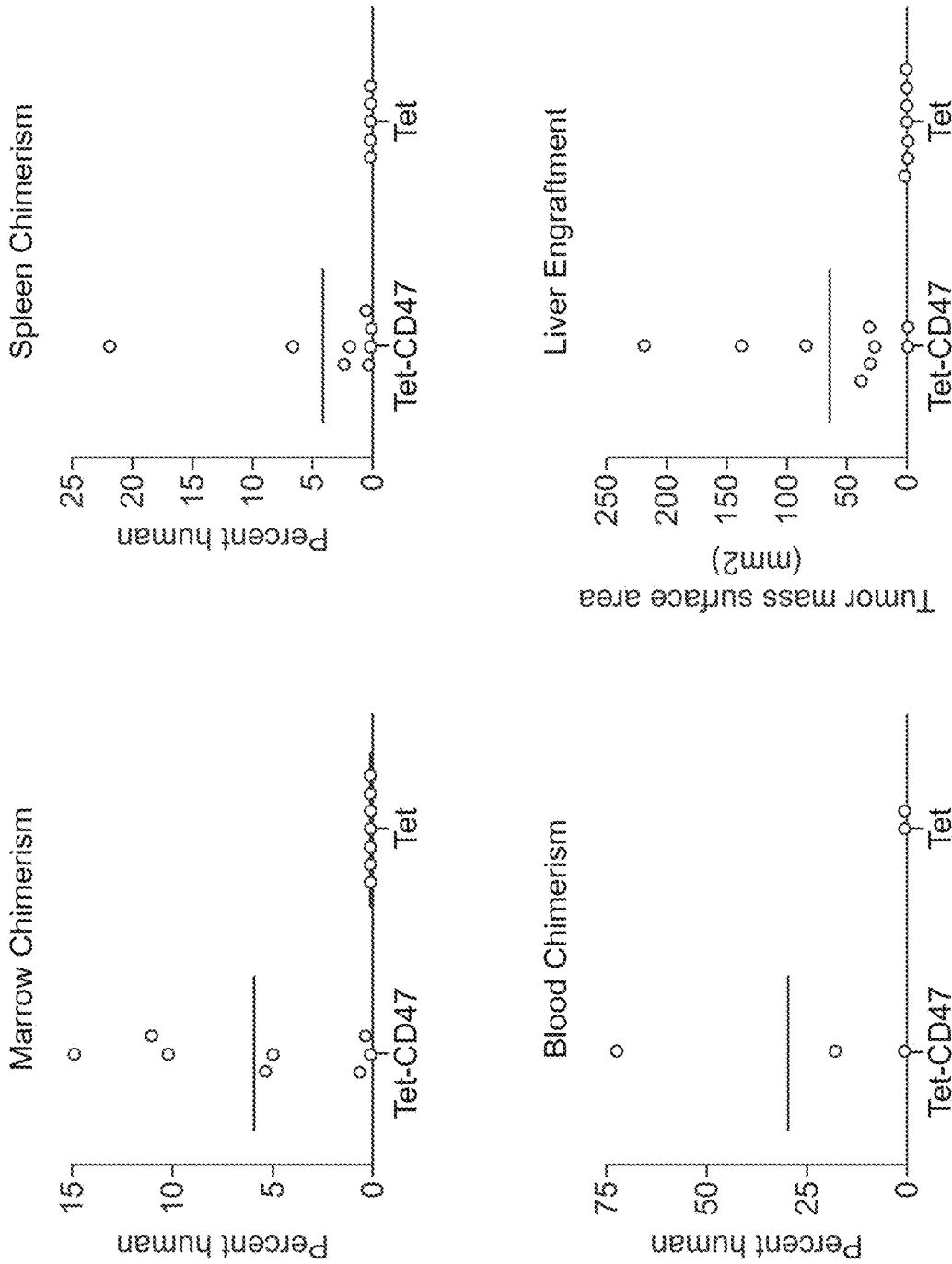
Figure 17:
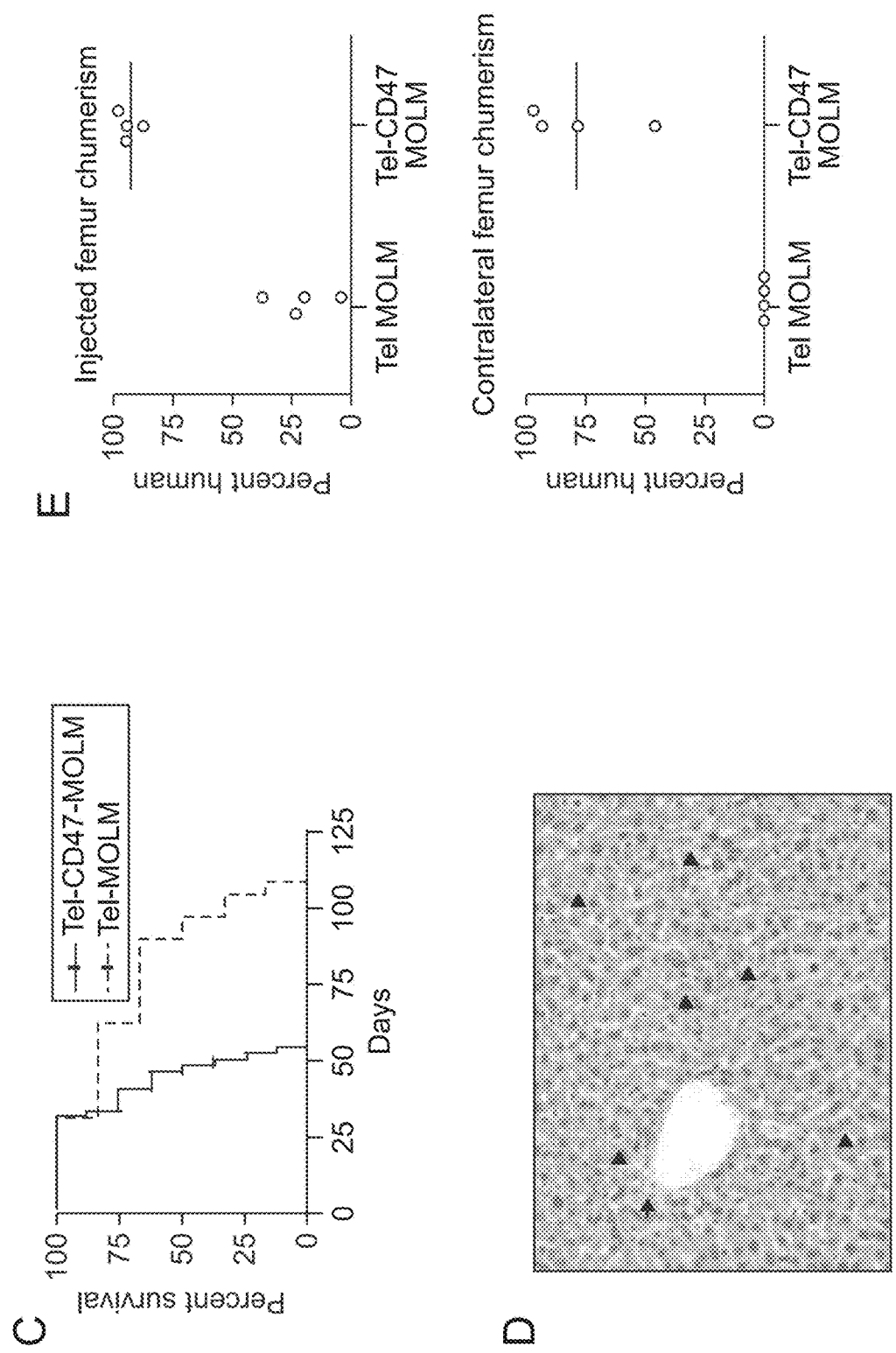
Figure 17:
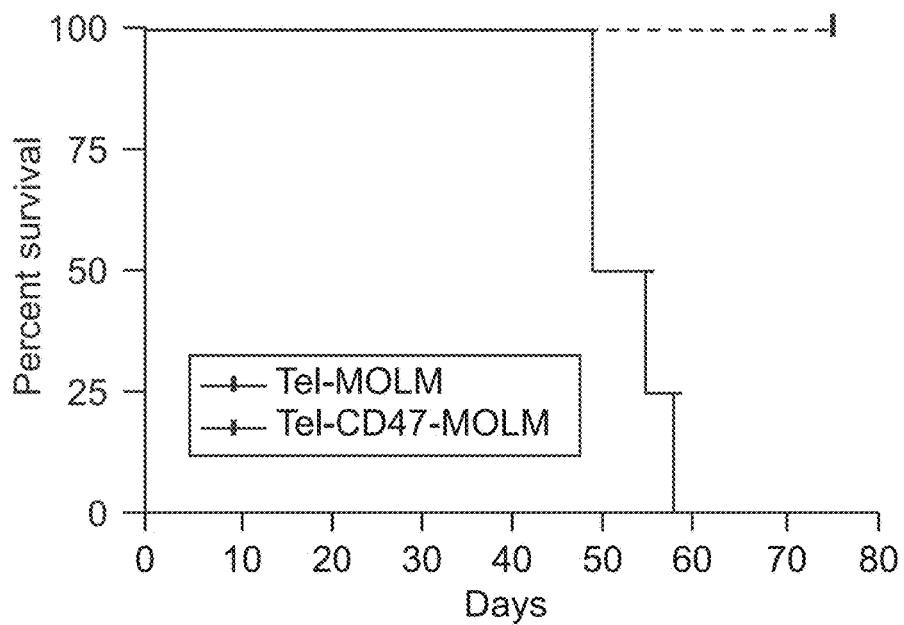
Figure 17:
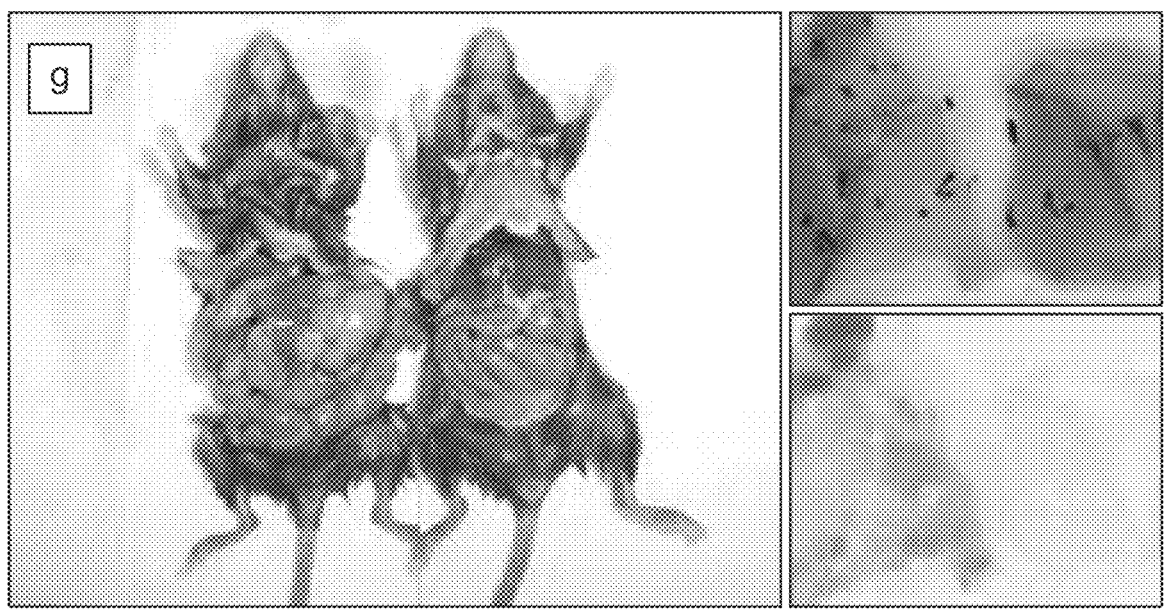

It was then asked whether forced expression of mouse CD47 on human leukemic cells would confer a competitive advantage in forming tumours in mice. MOLM-13 cells, which are derived from a patient with AML 5a, were transduced with Tet-MCS-IRES-GFP (Tet) or Tet-CD47-MCS-IRES-GFP (Tet-CD47) (FIG. 17a), and stable integrants were propagated on the basis of GFP expression. The cells were then transplanted intravenously in a competitive setting with untransduced MOLM-13 cells into T, B, and NK deficient recombination activating gene 2, common gamma chain deficient (RAG2−/−, Gc−/−) mice. Only cells transduced with Tet-CD47 were able to give rise to tumours in these mice, efficiently engrafting bone marrow, spleen and peripheral blood (FIGS. 17a-b). The tumours were also characterized by large tumour burden in the liver (FIGS. 17b, 17g), which is particularly significant because the liver is thought to have the highest number of macrophages of any organ, with estimates that Kupffer cells may comprise 80% of the total tissue macrophage population. These cells also make up 30% of the sinusoidal lining, thereby strategically placing them at sites of entry into the liver. Hence, significant engraftment there would have to disable a macrophage cytotoxic response. In addition to developing tumour nodules, the Tet-CD47 MOLM-13 cells exhibited patterns of hepatic involvement typically seen with human AML, with leukemic cells infiltrating the liver with a sinusoidal and perivenous pattern. (FIG. 17d). Overall, Tet-CD47 MOLM-13 transplanted mice died more quickly than Tet MOLM-13 transplanted mice, which had virtually no engraftment of leukemic cells in hematopoietic tissues (FIG. 17c). Tet-MOLM-13 mice still had significant mortality, most likely due to localized growth at the site of injection (retro-orbital sinus) with extension into the brain.

Since CD47 has been shown to be important for the migration of haematopoietic cells, and is known to modulate binding to extracellular matrix proteins, either by direct interaction or via its effect on integrins, one possibility for the lack of growth of Tet MOLM-13 cells in mice was their inability to migrate to niches. To test this possibility, Tet MOLM-13 or Tet-CD47 MOLM-13 cells were directly injected into the femoral cavity of immunodeficient mice. Tet-CD47 MOLM-13 cells were able to engraft all bones and other haematopoietic tissues of recipient mice, whereas Tet MOLM-13 cells had minimal, if any, engraftment only at the site of injection (FIG. 17e). Mice transplanted in this manner with Tet-CD47 MOLM-13 cells died at approximately 50-60 days post-transplant (n=4), whereas mice that received Tet MOLM-13 (n=5) cells remained alive for at least 75 days without signs of disease at which point they were euthanized for analysis. These results suggest a function other than or in addition to migration or homing for CD47 in MOLM-13 engraftment.

Figure 18:
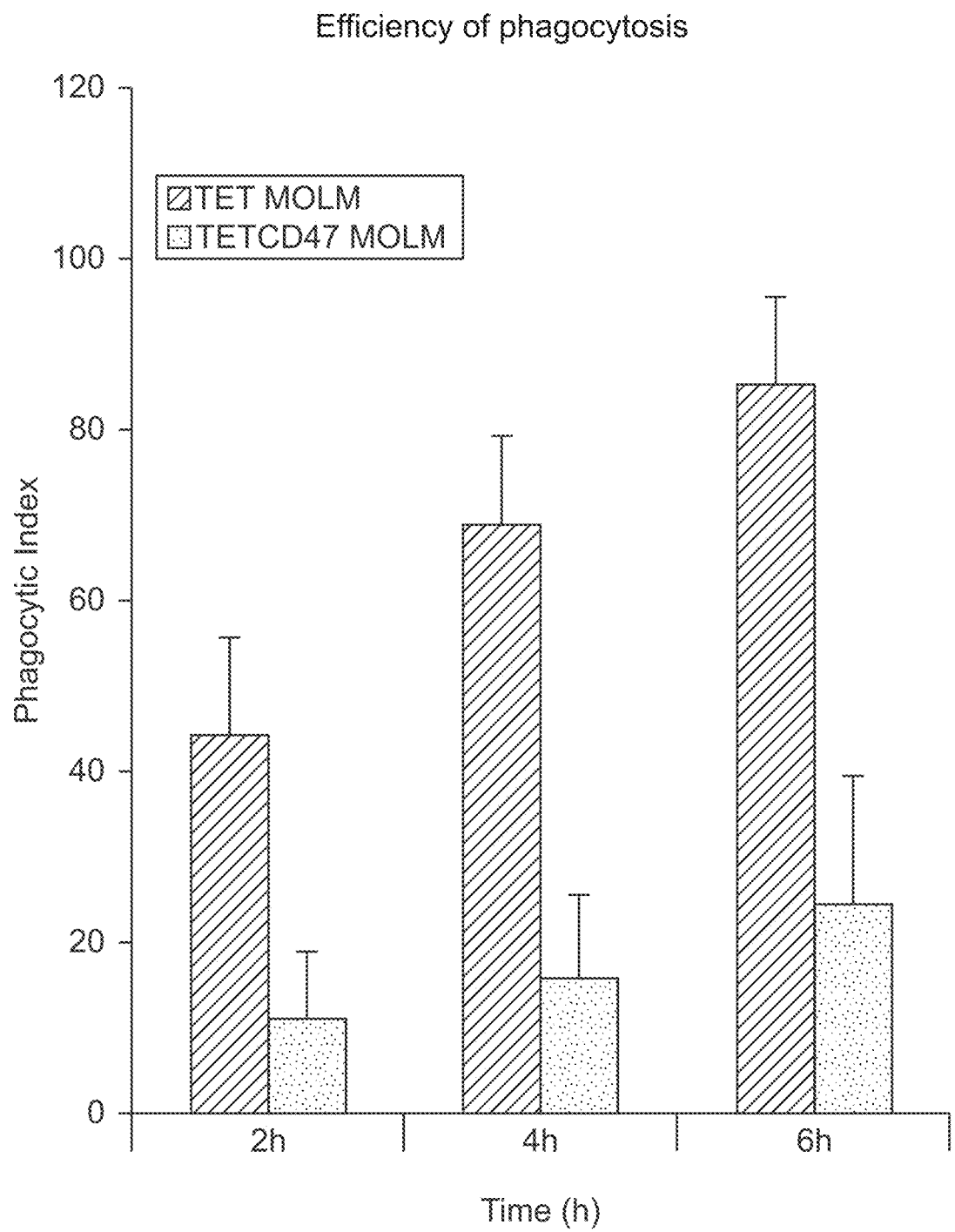
FIG. 18. CD47 over-expression prevents phagocytosis of live unopsonized MOLM-13 cells. a) Tet or Tet-CD47 MOLM-13 cells were incubated with bone marrow derived macrophages (BMDM) for 2, 4, or 6 hours and phagocytic index was determined. Error bars represent 1 s.d (n=6 for each time point). b) FACS analysis of BMDMs incubated with either Tet or Tet-CD47 cells. c) Photomicrographs of BMDMs incubated with Tet or Tet-CD47 MOLM-13 cells at 2 and 24 hours (400×). d) Tet or Tet-CD47 MOLM-13 cells were transplanted into RAG2−/−, Gc−/− mice and marrow, spleen, and liver macrophages were analyzed 2 hours later. GFP+ fraction of macrophages are gated. Results are representative of 3 experiments.
Figure 18:
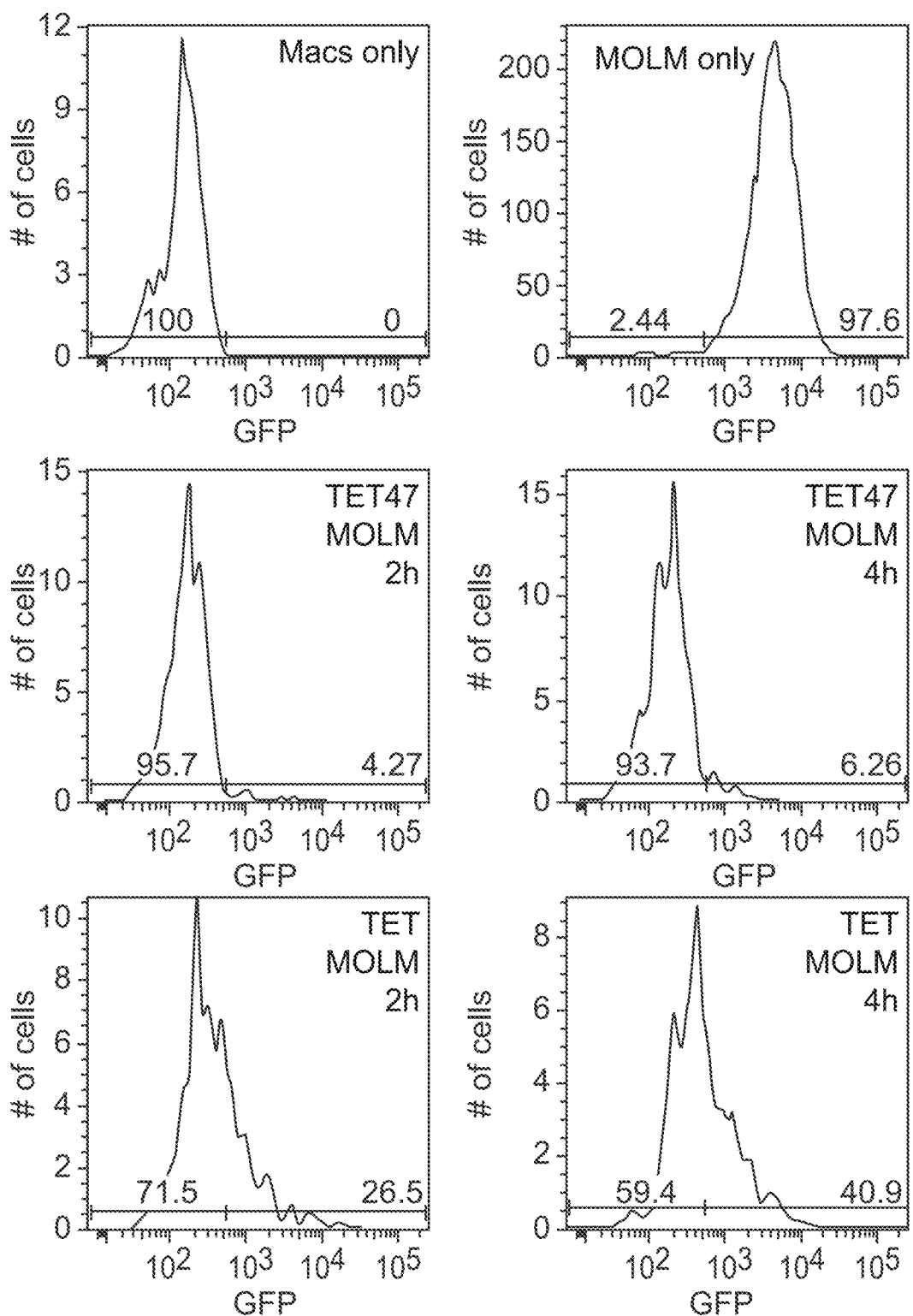
Figure 18:
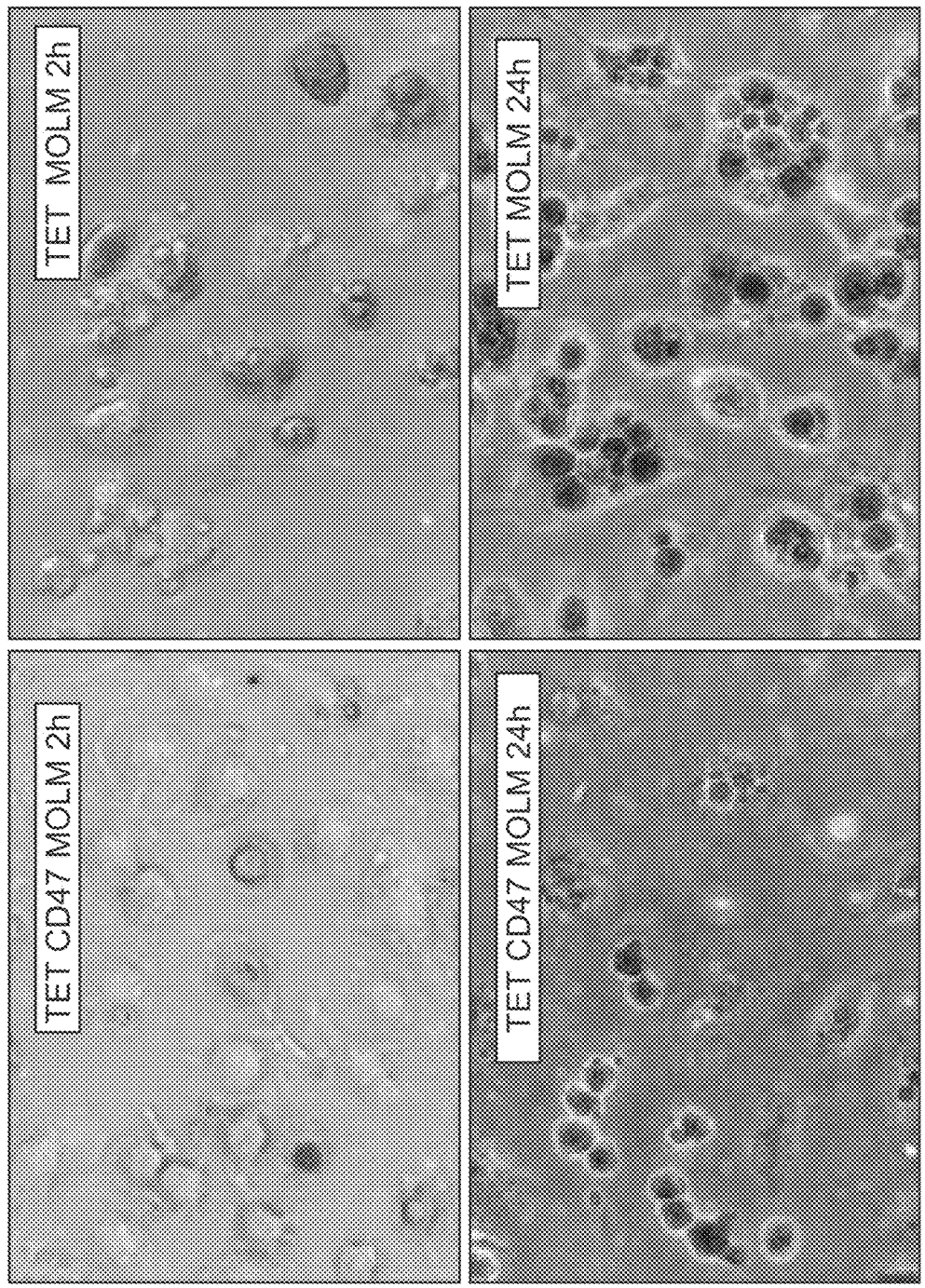
Figure 18:
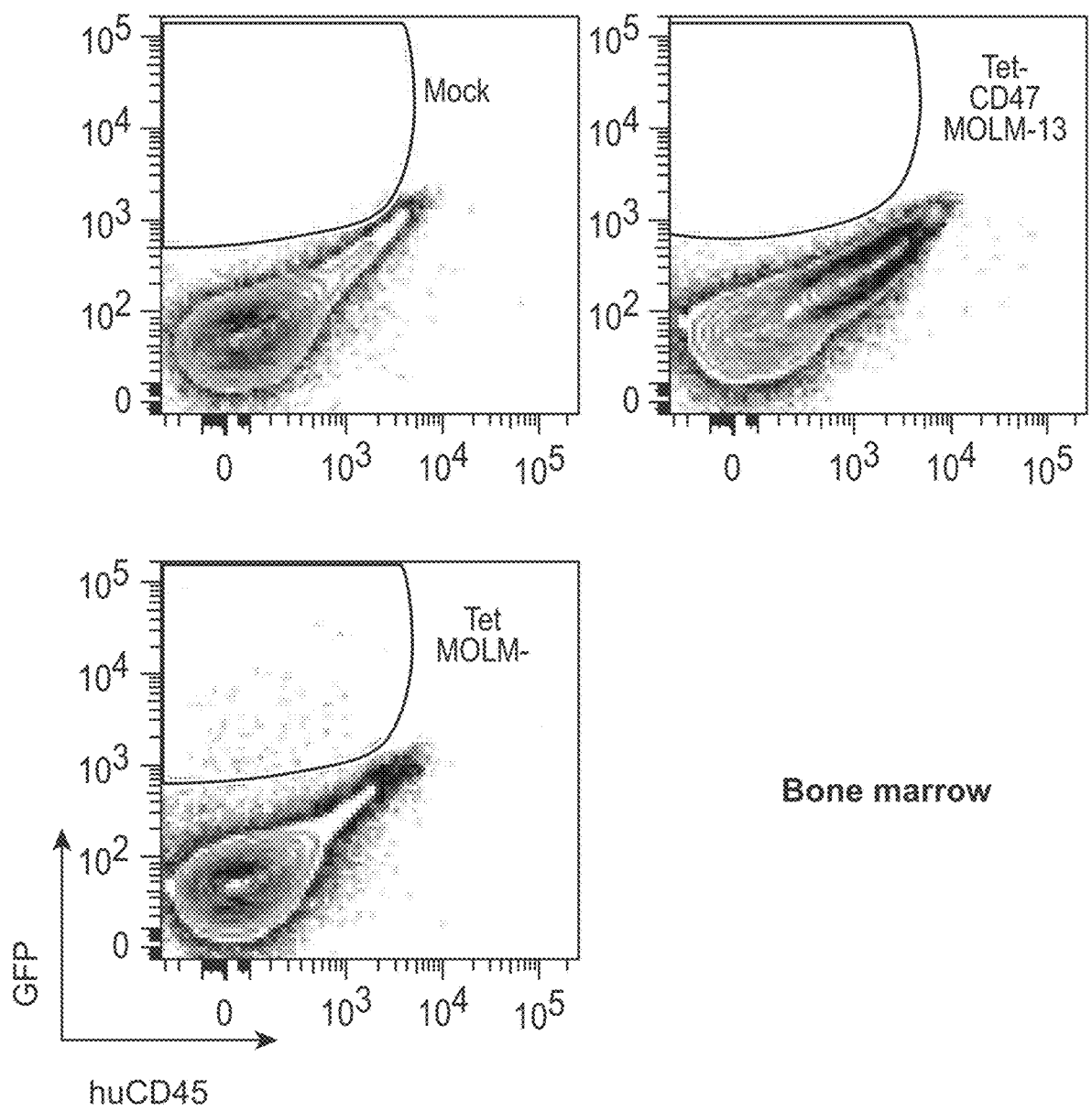
Figure 18:
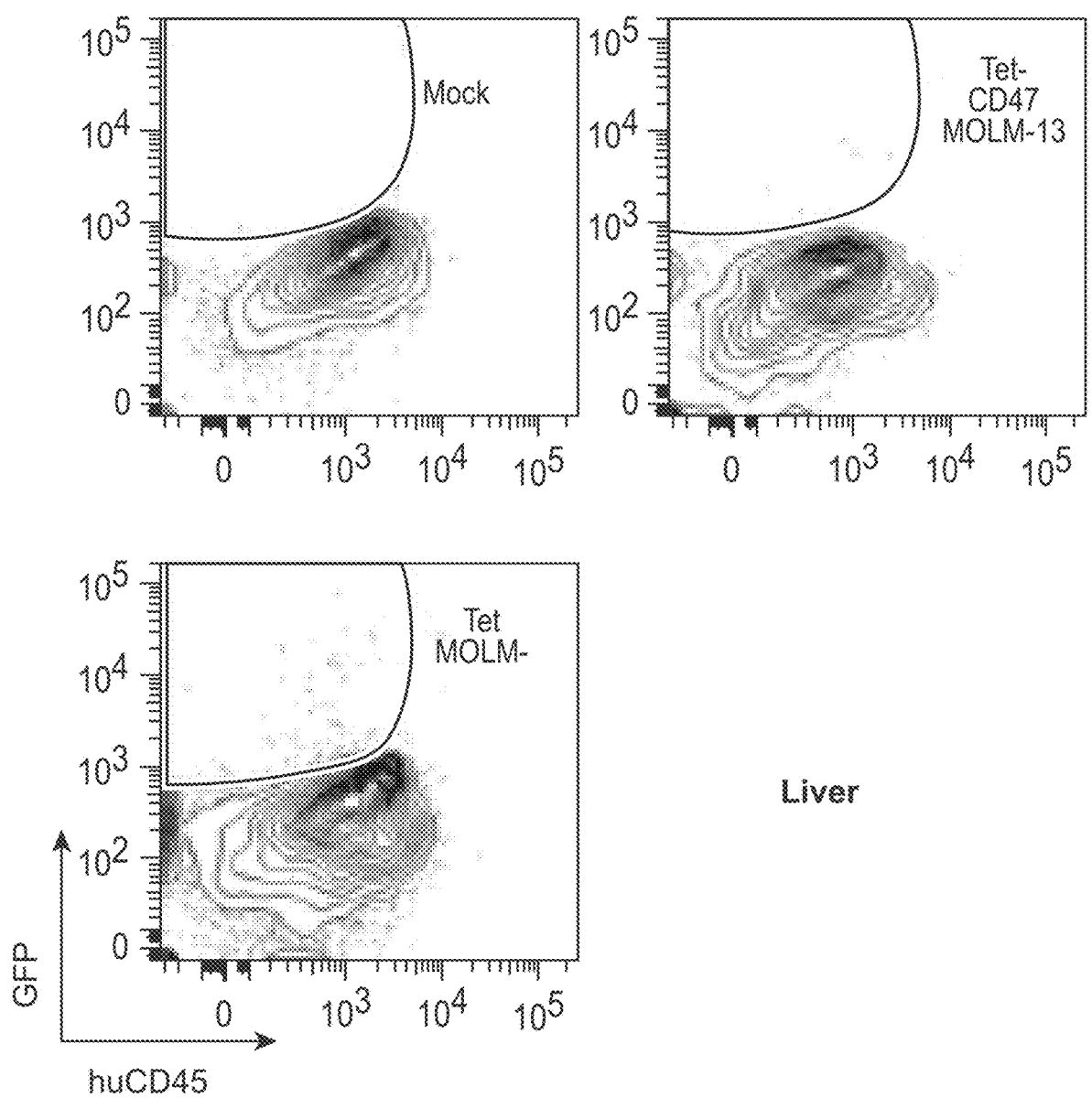
Figure 18:
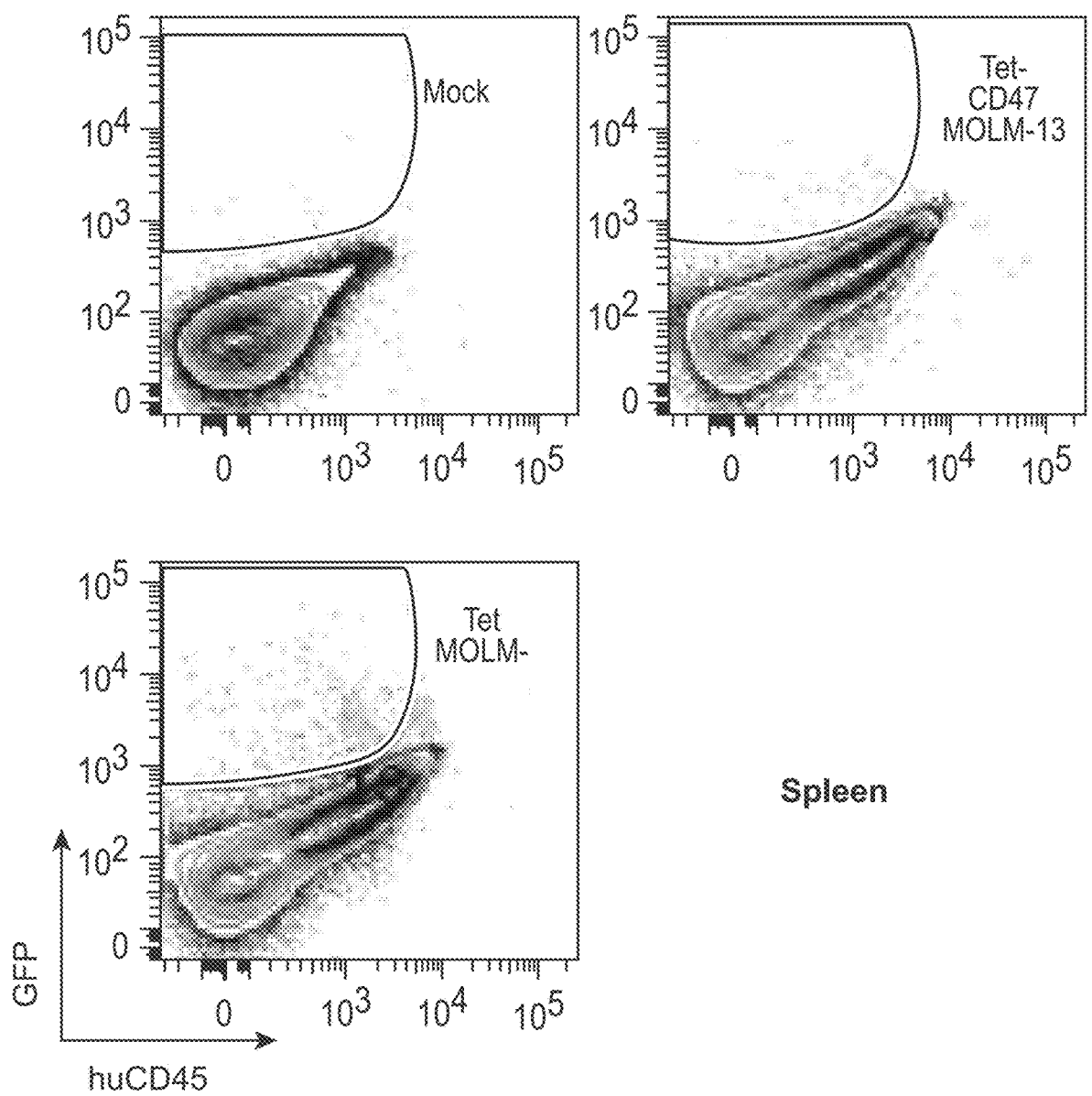

Complete lack of CD47 has been shown to result in phagocytosis of transplanted murine erythrocytes and leukocytes, via lack of interaction with SIRPα on macrophages. Thus, we tested whether over-expression of CD47 could prevent phagocytosis of live, unopsonized MOLM-13 cells. We incubated Tet or Tet-CD47 MOLM-13 cells with bone marrow derived macrophages (BMDM) for 2-24 hours and assessed phagocytosis by counting the number of ingested GFP+ cells under a microscope or by evaluating the frequency of GFP+ macrophages using a flow cytometer. Expression of CD47 dramatically lowered macrophage clearance of these cells at all time points tested, whereas Tet-MOLM-13 were quickly phagocytosed in a manner that increased overtime (FIGS. 18a-c). We also injected MOLM-13 cells into mice and analyzed hematopoietic organs 2 hours later for evidence of macrophage phagocytosis. Macrophages in bone marrow, spleen, and liver all had higher GFP+ fraction when injected with Tet MOLM-13 cells as compared to CD47 expressing cells. This indicates that CD47 over-expression can compensate for pro-phagocytic signals already present on leukemic cells, allowing them to survive when they would otherwise be cleared by macrophages.

Recent report indicates that lack of CD47 reactivity across species might mediate xenorejections of transplanted cells. Furthermore, a recent study has demonstrated that human CD47 is unable to interact with SIRPα from C57Bl/6 mice, but is able to react with receptor from non-obese diabetic (NOD) mice, which are more permissive for human cell engraftment than C57Bl/6 mice. Furthermore, we have also observed that HL-60 cells, a human promyelocytic cell line with higher levels of human CD47 expression than MOLM-13, are able to engraft mice and cause leukaemia. Jurkat cells, a human T-lymphocyte cell line, are very high for human CD47 and are phagocytosed by murine macrophages in vitro at a much lower rate than MOLM-13. Thus, our data indicate that the ability of cells to engraft mice in vivo or evade phagocytosis in vitro by mouse macrophages correlates with the level of human CD47 expression.

Figure 19:
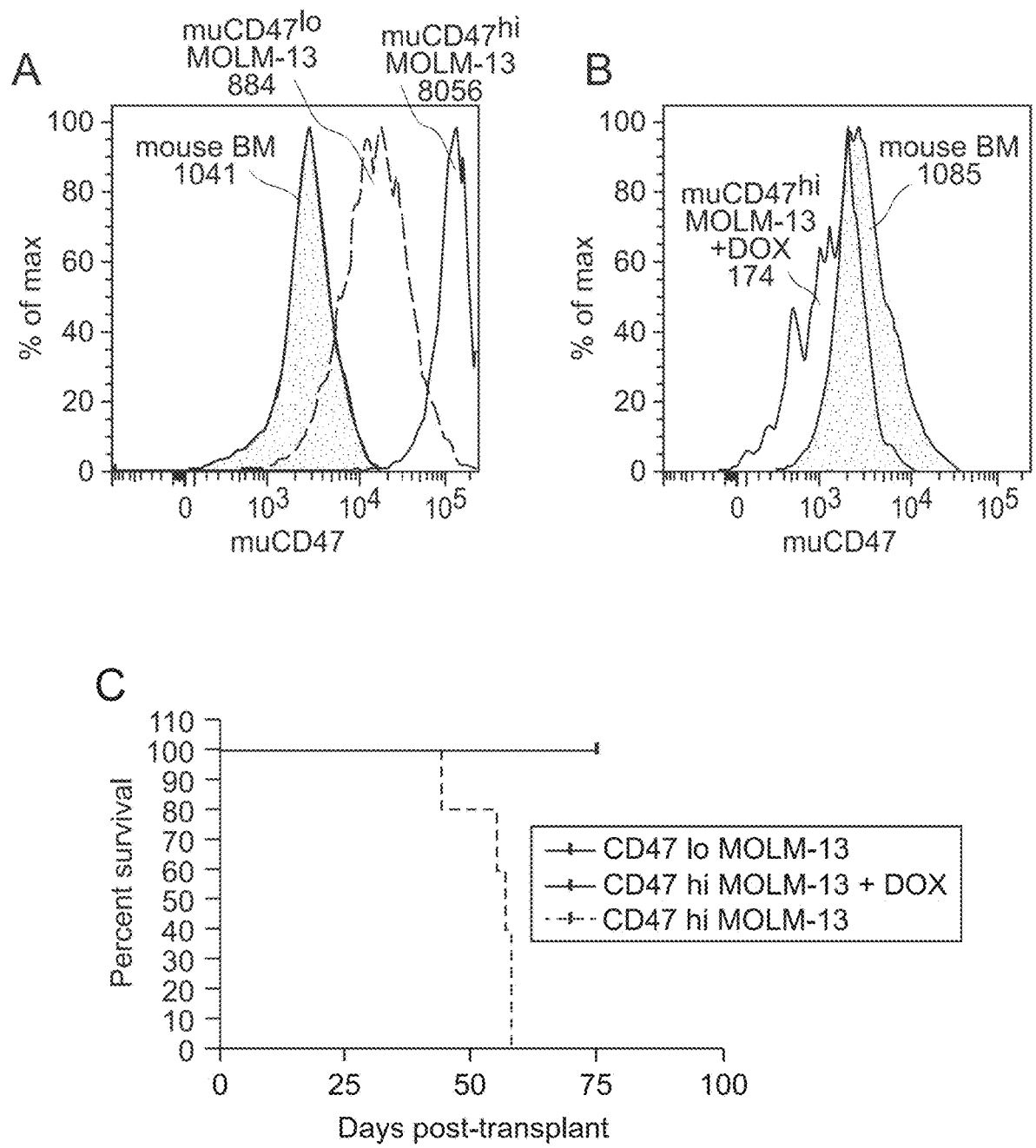
FIG. 19. Higher expression of CD47 on MOLM-13 cells correlates with tumorigenic potential and evasion of phagocytosis. a) Tet-CD47 MOLM-13 cells were divided into high and low expressing clones as described. Histograms show CD47 expression in MOLM-13 high (black), MOLM-13 low (gray), and mouse bone marrow (shaded) cells. Value obtained for MFI/FSC² ($\times 10^9$) are shown. b) Mice transplanted with CD47hi MOLM-13 cells were given doxycycline for 2 weeks. The histograms show level of CD47 expression in untreated (shaded) and treated (shaded) mice, with the values of MFI/FSC² ($\times 10^9$) indicated. c) Survival of RAG2−/−, Gc−/− mice transplanted with $1 \times 10^6$ CD47$^{hi}$, CD47$^{lo}$ MOLM-13 cells, or CD47$^{hi}$ MOLM-13 cells with doxycycline administration after 2 weeks post-transplant. d) Liver and spleen size of mice at necropsy or 75 days after transplant with $1 \times 10^6$ CD47$^{hi}$, CD47$^{lo}$ MOLM-13 cells, or CD47$^{hi}$ MOLM-13 cells with doxycycline administration after 2 weeks post-transplant. e) Bone marrow and spleen chimerism of human cells in mice at necropsy or 75 days after transplant with $1 \times 10^6$ CD47$^{hi}$, CD47$^{lo}$ MOLM-13 cells, or CD47$^{loi}$ MOLM-13 cells with doxycycline administration after 2 weeks post-transplant. f) Murine CD47 expression on CD47l° MOLM-13 cells engrafting in bone marrow (open) compared with original cell line (shaded). The values of MFI/FSC² ($\times 10^9$) are indicated. g) $2.5 \times 10^5$ CD47$^{hi}$ or CD47$^{lo}$ MOLM-13 cells were incubated with $5 \times 10^4$ BMDMs for 2 hours. Phagocytic index is shown. h) $2.5 \times 10^5$ CD47$^{hi}$ RFP and CD47$^{lo}$ MOLM-13 GFP cells were incubated with $5 \times 10^4$ BMDMs for 2 hours. Phagocytic index is shown for three separate samples for CD47$^{hi}$ RFP (red) and CD47$^{lo}$ MOLM-13 GFP (green) cells. i) $2.5 \times 10^5$ CD47$^{hi}$ RFP and CD47$^{lo}$ MOLM-13 GFP cells were incubated with $5 \times 10^4$ BMDMs for 24 hours. Photomicrographs show brightfield (top left), RFP (top right), GFP (bottom left), and merged (bottom right) images.
Figure 19:
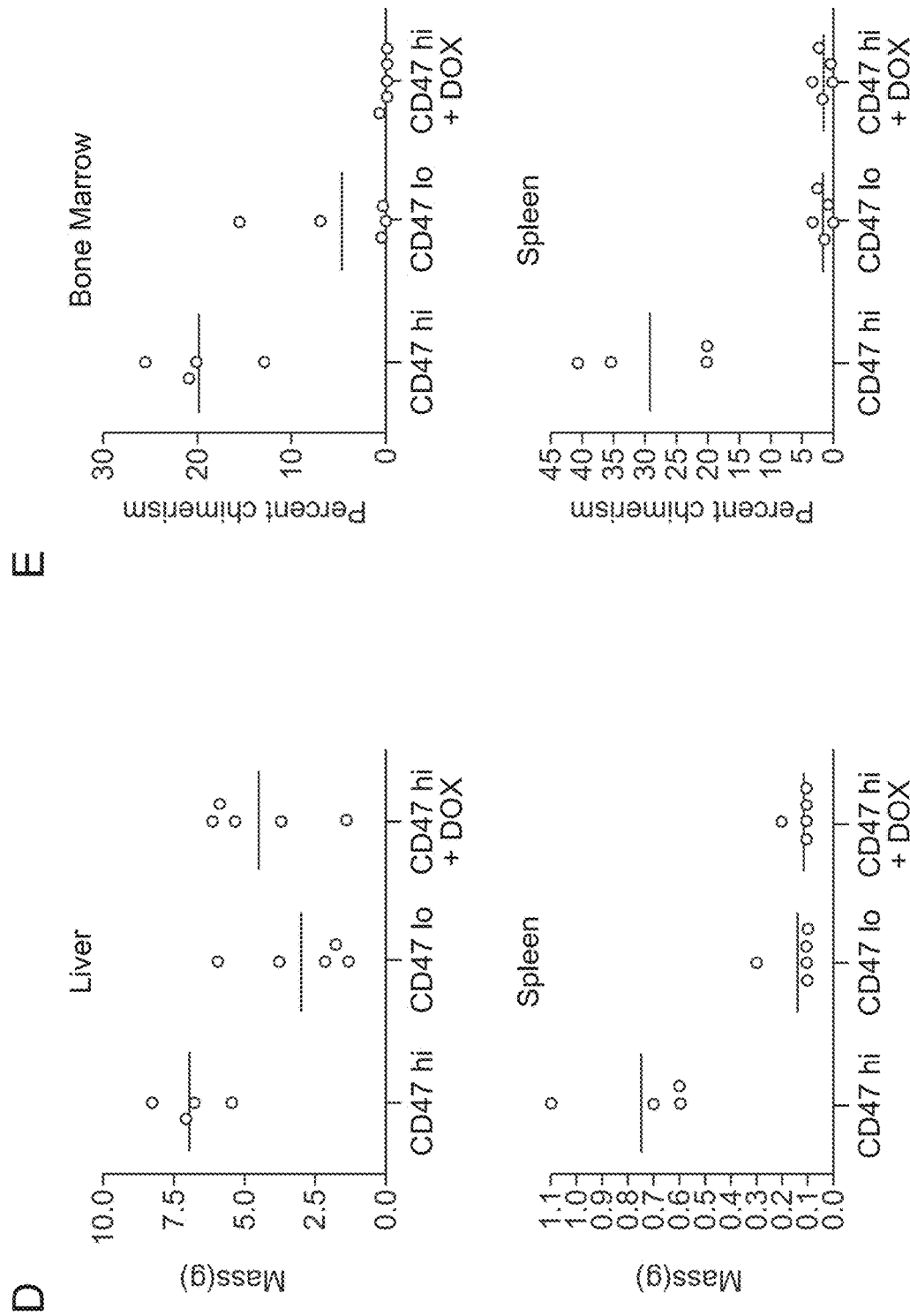
Figure 19:
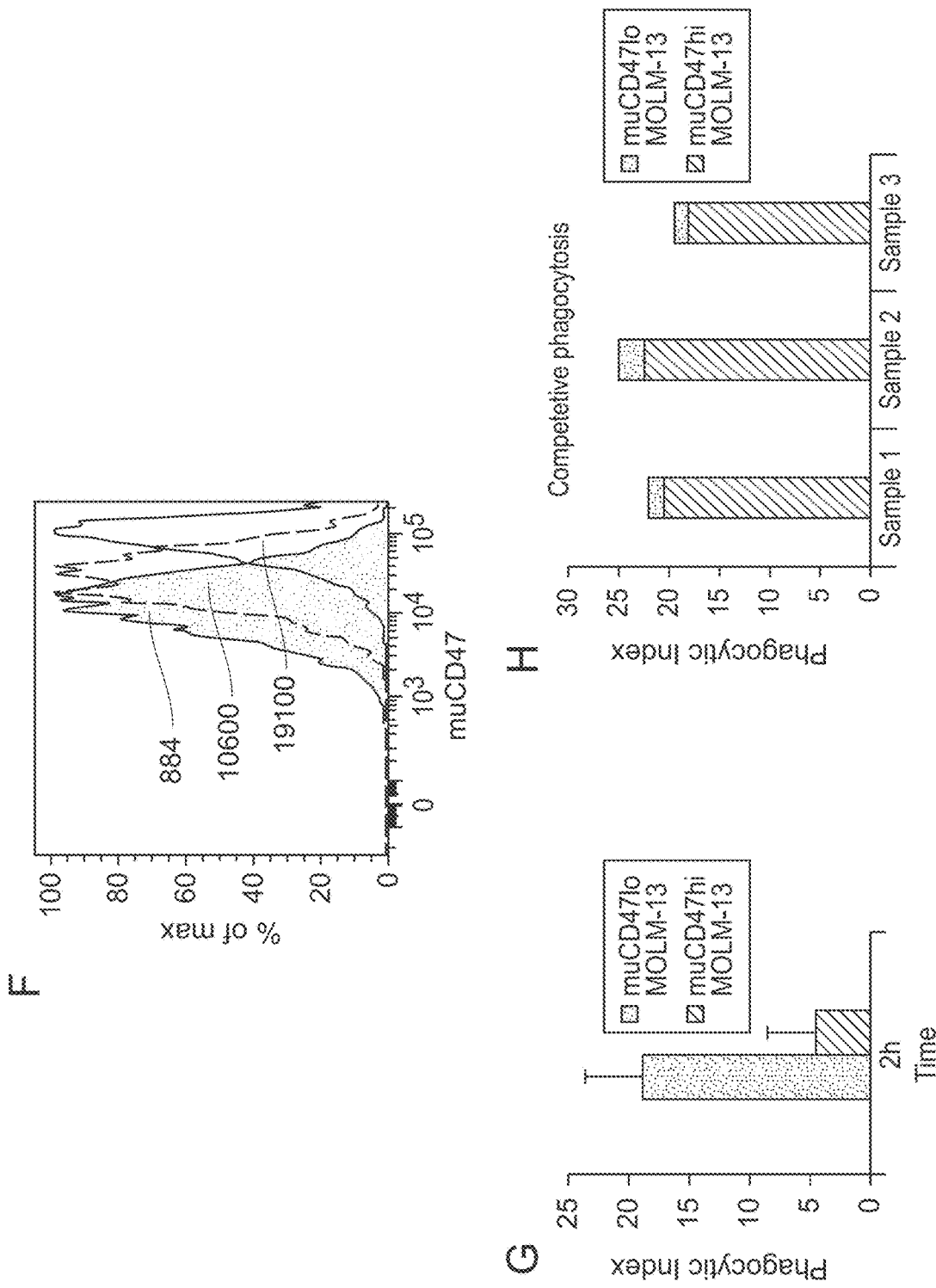
Figure 19:
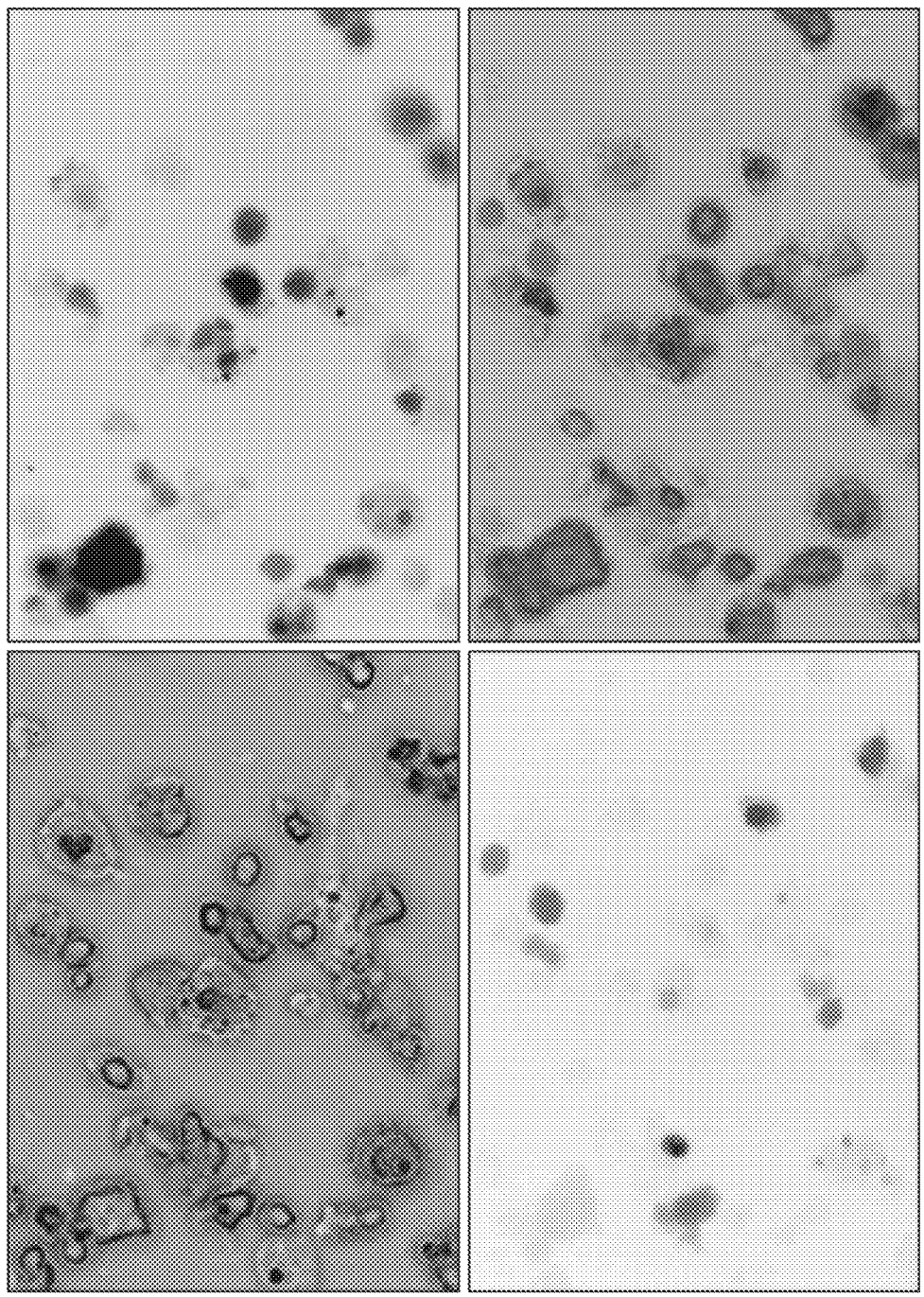
Figure 20:
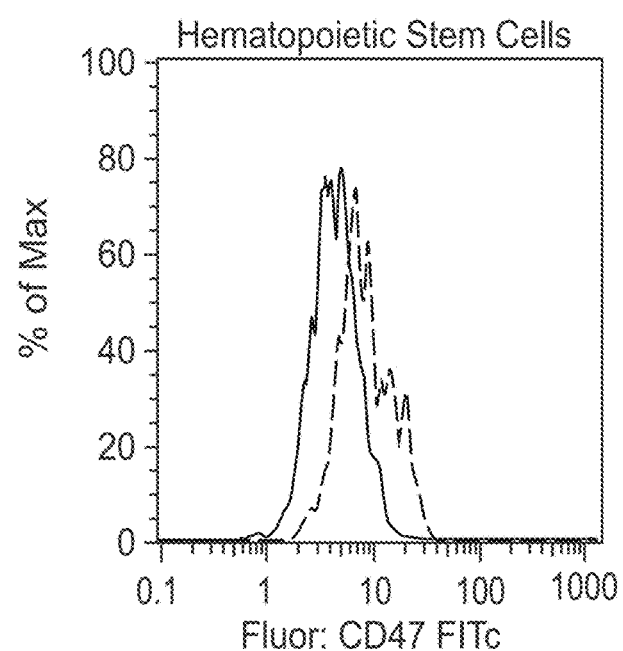
FIG. 20. a) FACS analysis of CD47 expression of non-leukemic Fas lpr/lpr hMRP8bcl-2 (blue) and leukemic Fas lpr/lpr hMRP8bcl-2 (green) bone marrow haematopoietic stem cells (c-kit+Sca+Lin−), myeloid progenitors (c-kit+Sca−Lin−) or blasts (c-kit lo Sca−Lin−). b) Mouse bone marrow was transduced with retrovirus containing p210 bcr/abl as previously described[24]. Mice were sacrificed when moribund and the spleens were analyzed. Expression of CD47 in c-Kit+Mac-1+ cells in the spleens of two leukemic mice (unshaded histograms) and bone marrow from a wild-type mouse (shaded histogram) are shown. c) Histograms show expression of CD47 on gated populations for leukemic hMRP8bcrablxhMRP8bcl2 mice (red), hMRP8bcl2 non-leukemic (blue) and wild-type (green) mice. CD47 was stained using FITC conjugated anti-mouse CD47 (Pharmingen).
Figure 20:
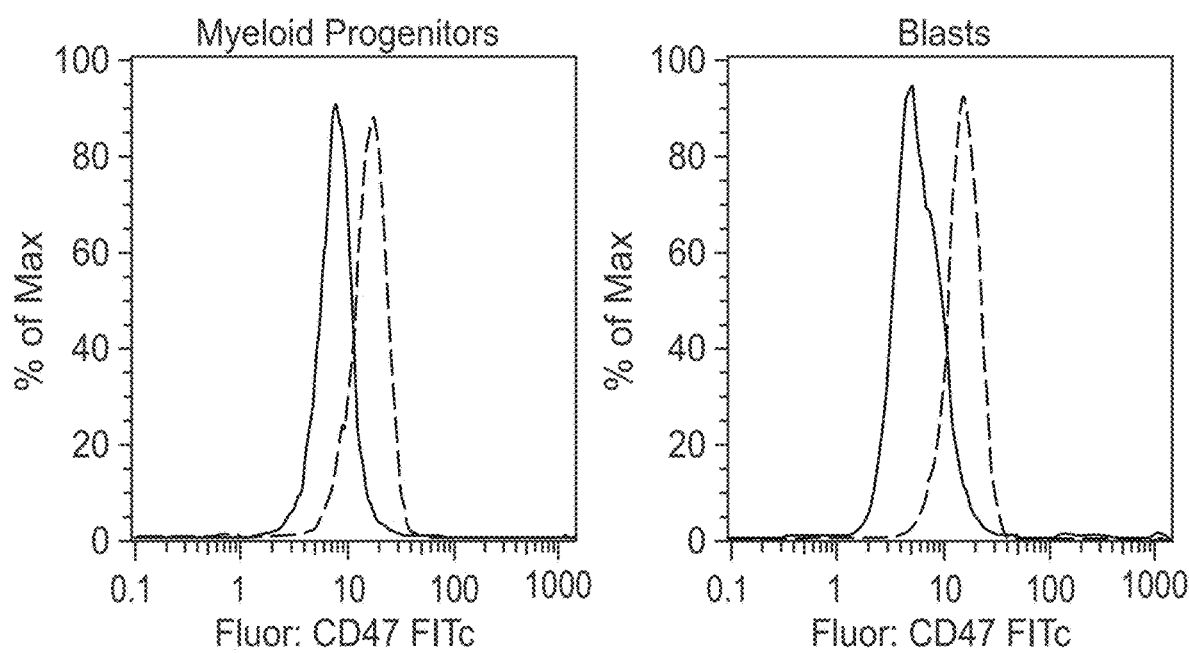
Figure 20:
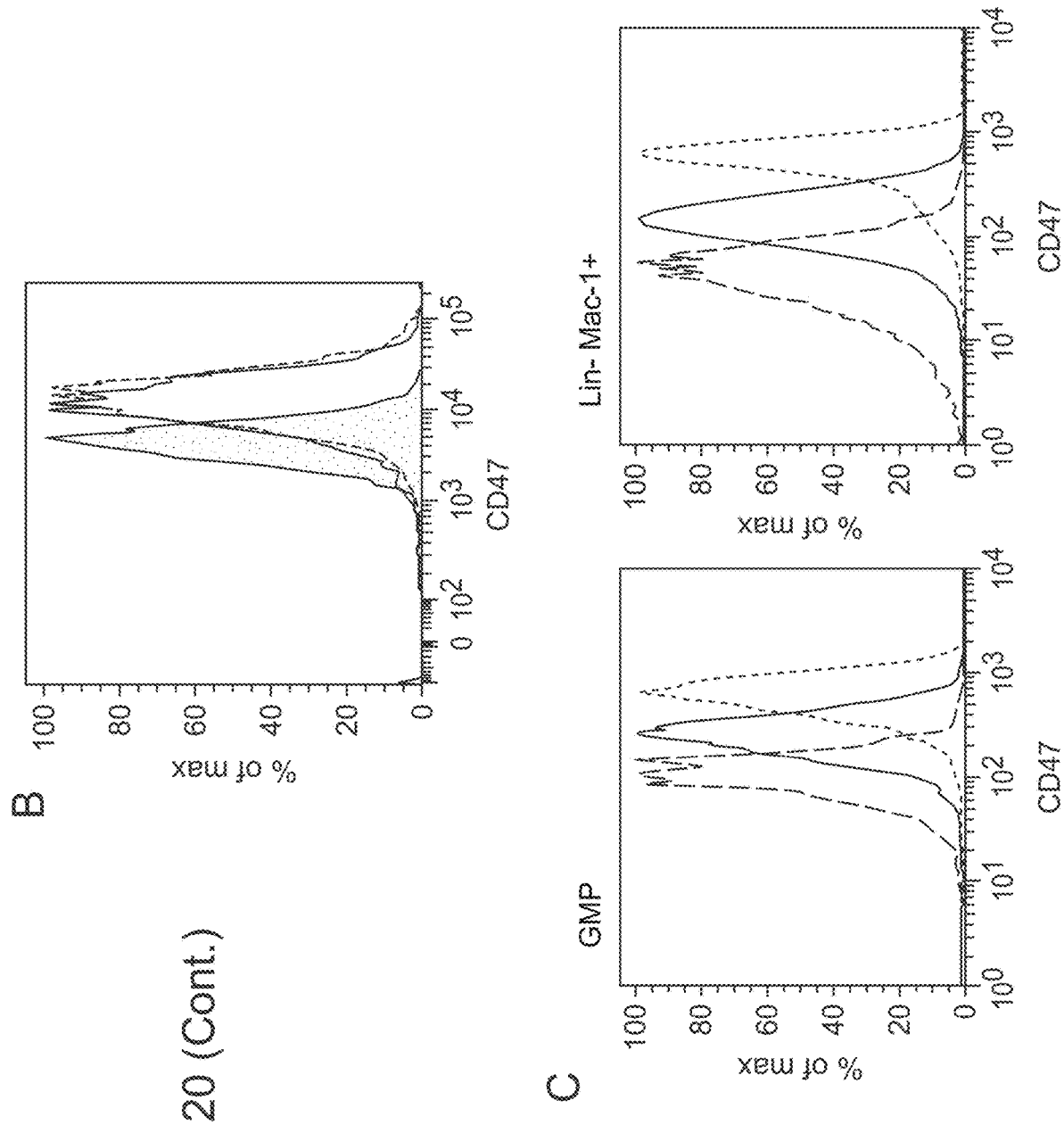
Figure 21:
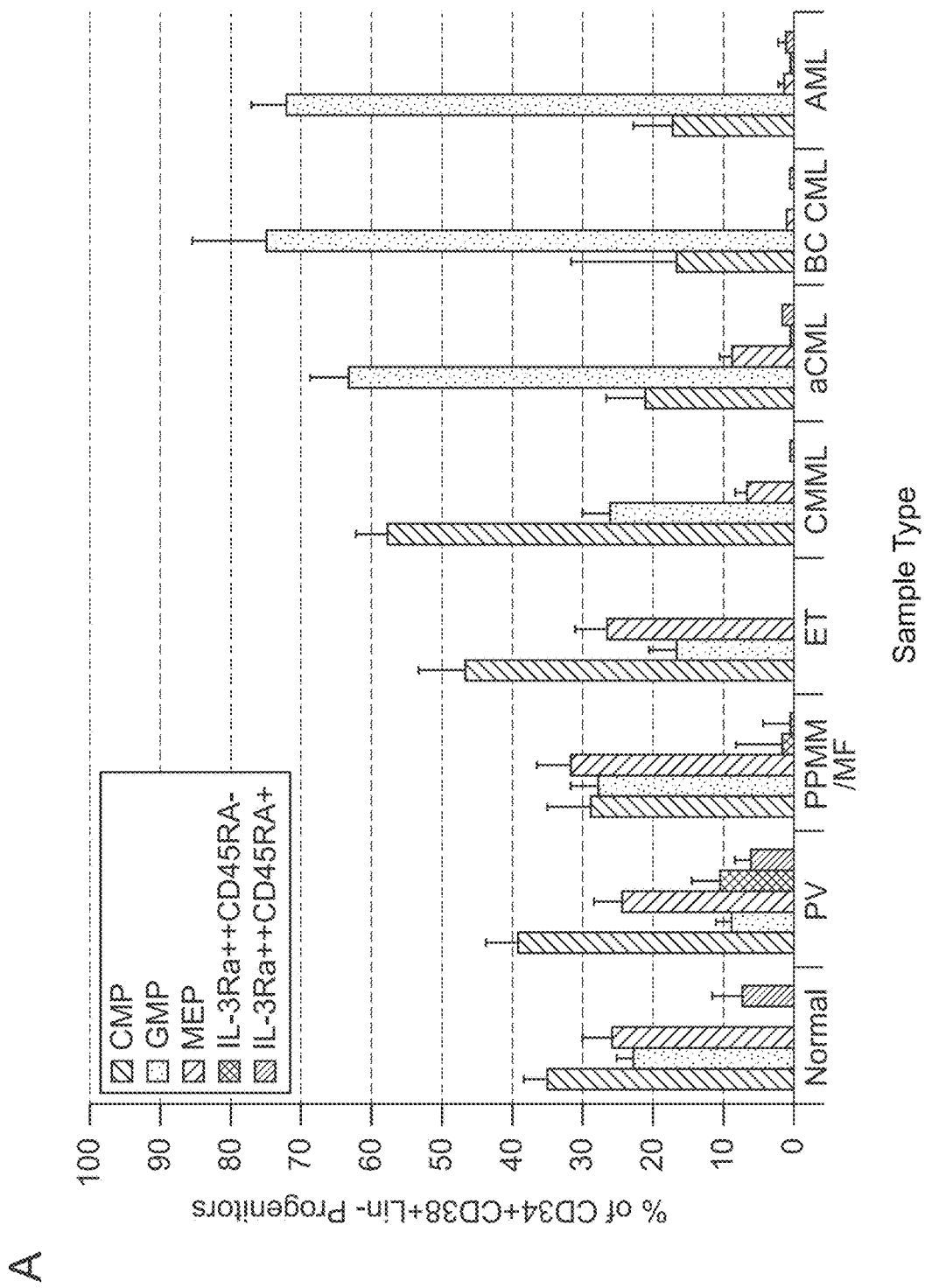
FIG. 21. a) Mean % of CD34+CD38+Lin− progenitors in normal versus polycythemia vera (PV; n=16), post-polycythemic myeloid metaplasia/myelofibrosis (PPMM/MF; n=5), essential thrombocythemia (ET; n=7), chronic myelomonocytic leukemia (CMML; n=11), atypical chronic myelogenous leukemia (aCML; n=1), blast crisis CML (BC CML; n=6) and acute myelogenous leukemia (AML; n=13) peripheral blood or bone marrow. b) Staining for CD47 using newer staining protocol on stem and progenitor cells from normal human cord blood, chronic phase, and blast crisis CML. Normal (green), CML-CP (red), and CML-BC (blue) are shown.
Figure 21:
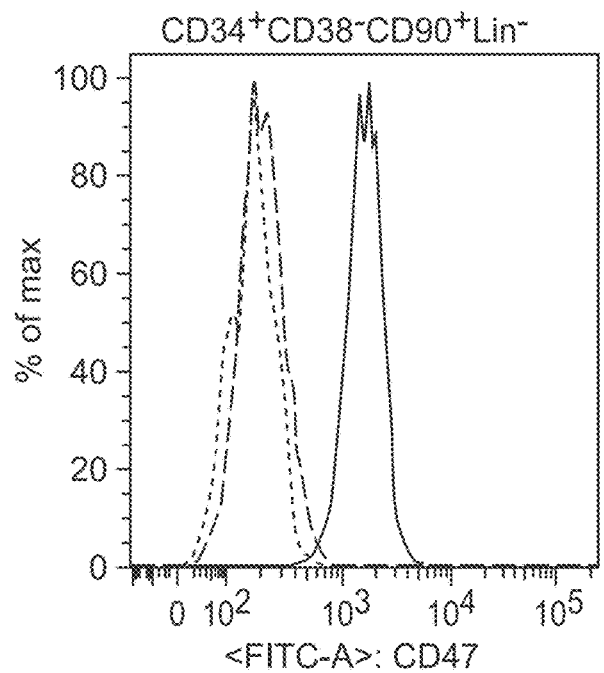
Figure 21:
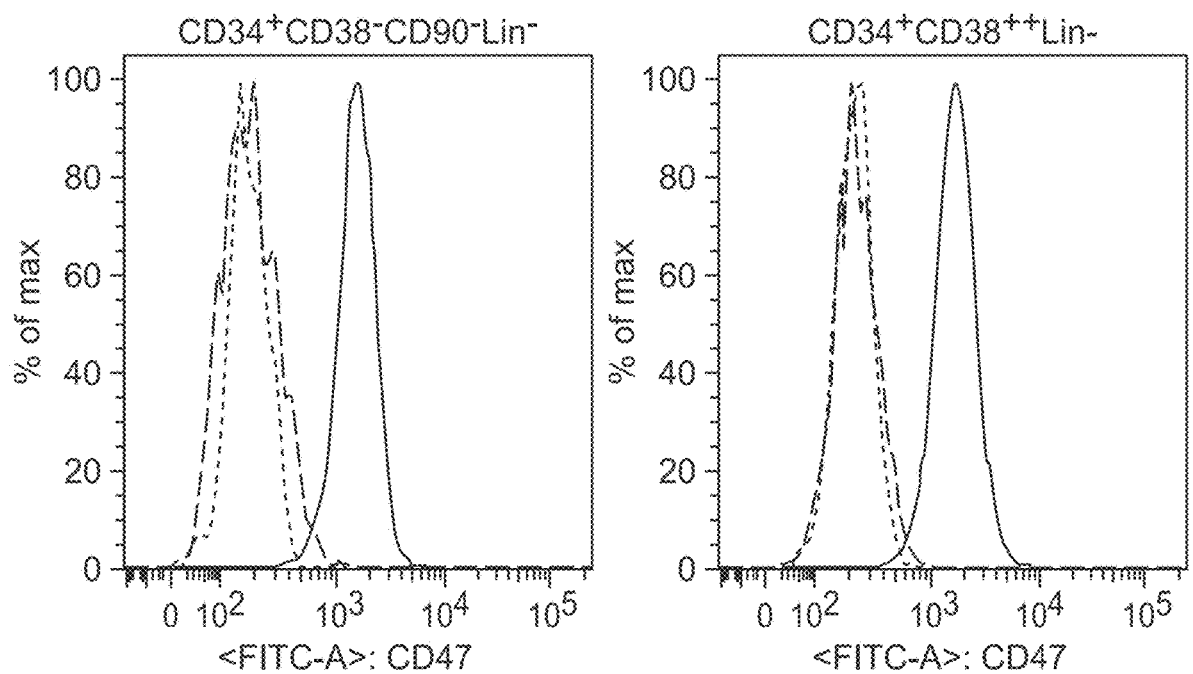
Figure 22:
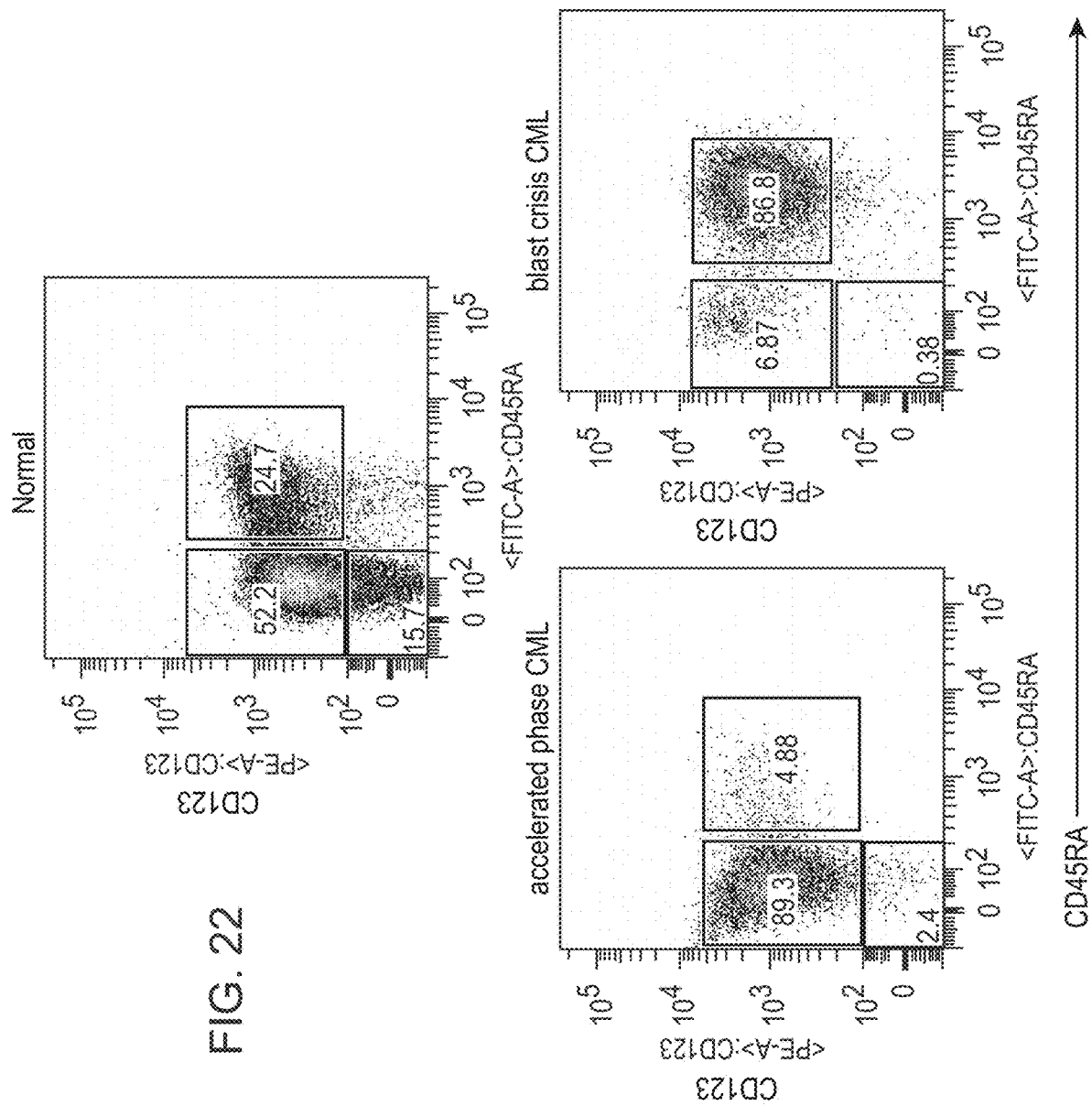
FIG. 22. CD123/CD45a FACS plot of normal marrow (left), accelerated phase CML (middle) and CML BC progenitors (right).
Figure 23:
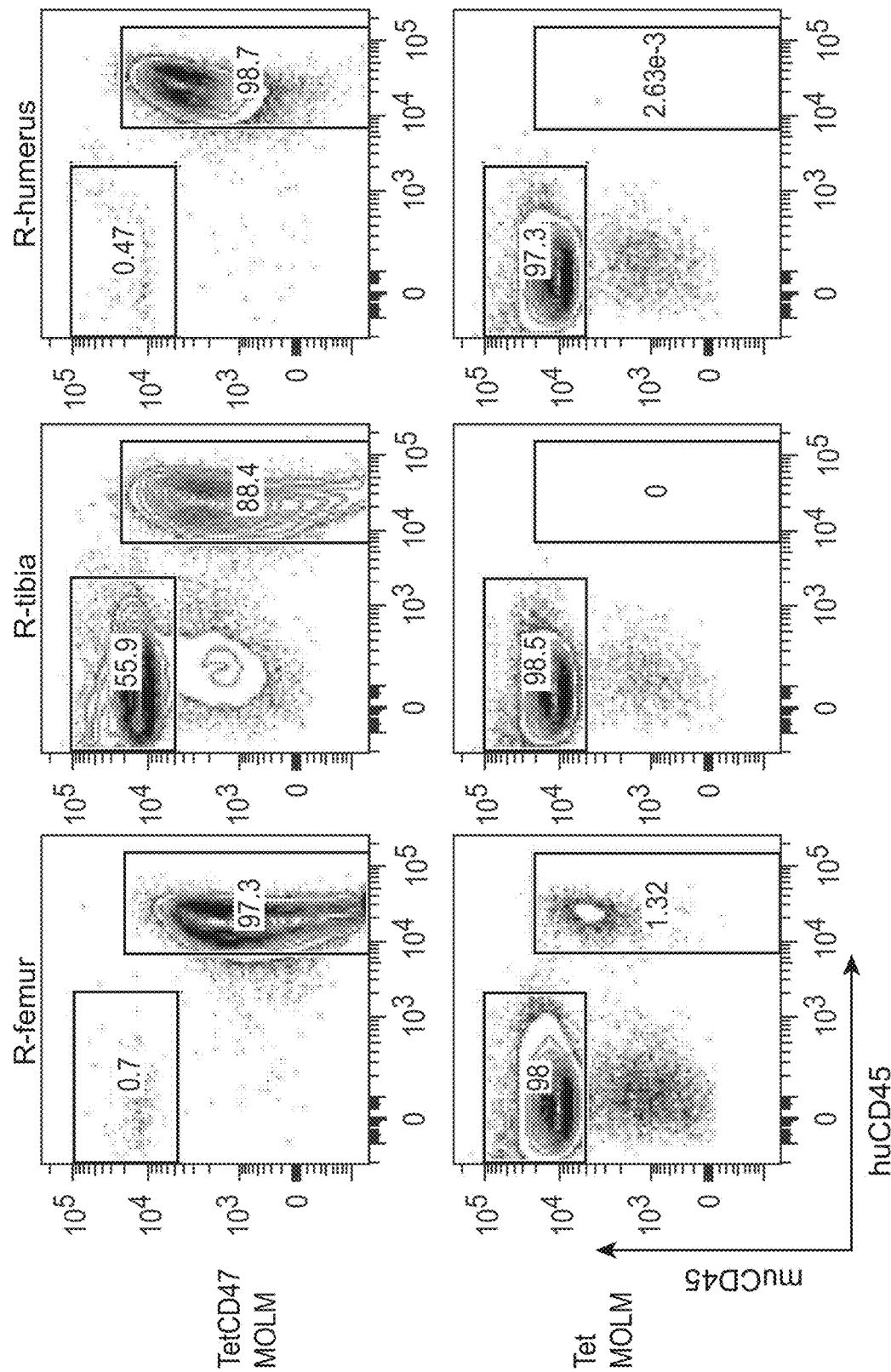
FIG. 23. Representative FACS plots from mice transplanted intrafemorally with Tet or Tet-CD47 MOLM-13 cells. All 6 long bones as well as spleen demonstrate profound MOLM-13 engraftment in Tet-CD47 transplanted mice. R-right, L-left.
Figure 23:
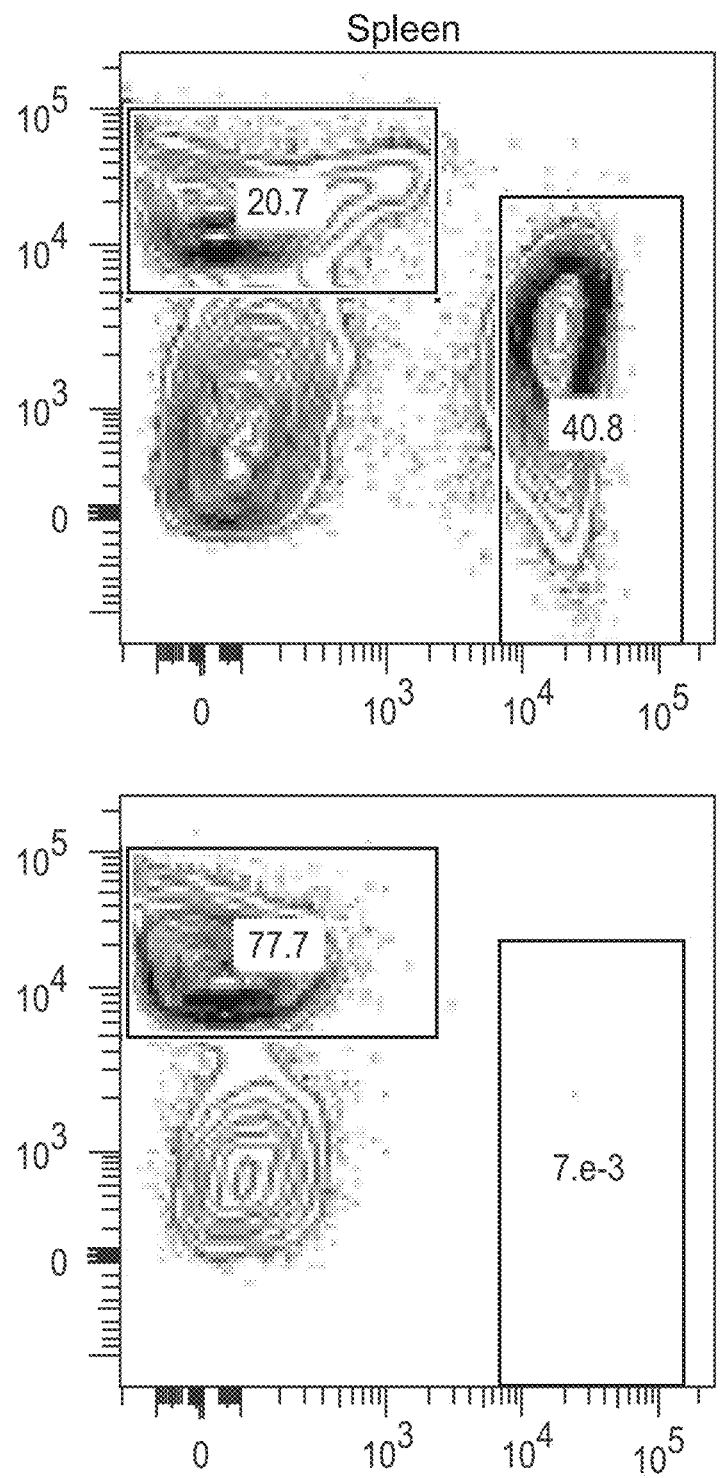
Figure 24:
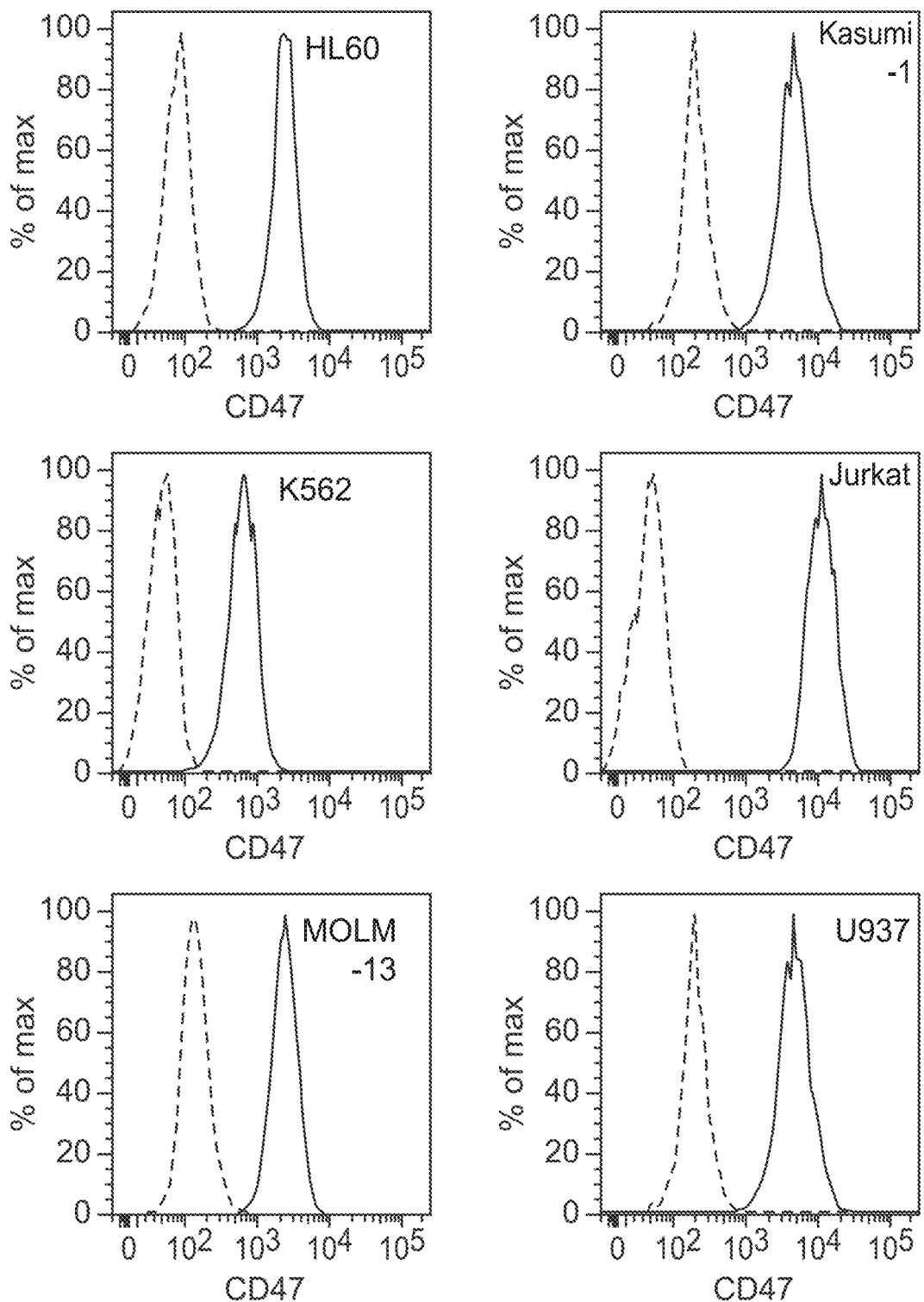
FIG. 24. a) Expression of human CD47 (black histograms) on human leukemia cell lines and cord blood HSCs is shown. Isotype control staining is shown in gray. b) CD47 MFI over background was normalized to cell size by dividing by FSC². The value obtained for each cell type is shown above the bar. c) HL-60 cells engraft mouse bone marrow. $5 \times 10^5$ cells were injected intravenously into RAG2−/−, Gc−/− animals and mice were analyzed 4 weeks later. d) Cells were stained with CFSE and co-cultured with BMDM. Phagocytic events were counted after 2 h. For irradiation, Jurkat cells were given a dose of 2 Gray and incubated for 16 h prior to the phagocytosis assay.
Figure 24:
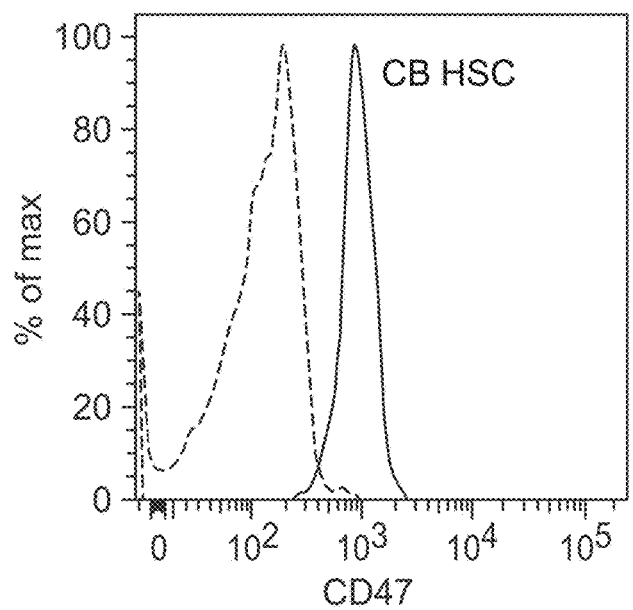
Figure 24:
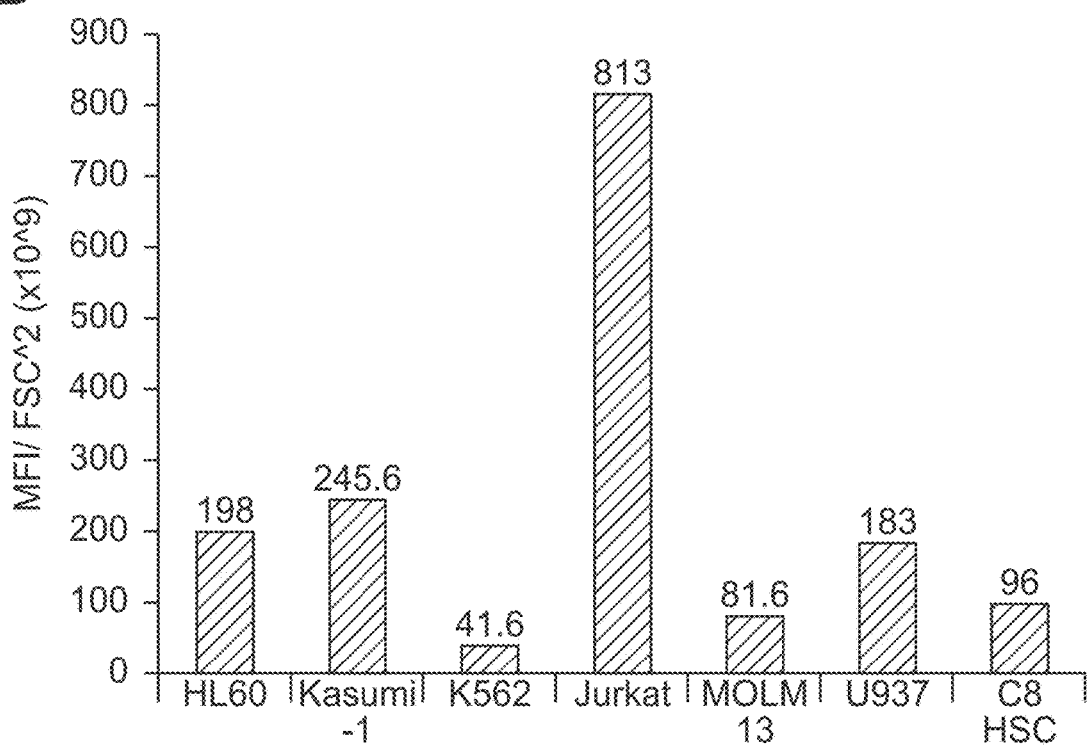
Figure 24:
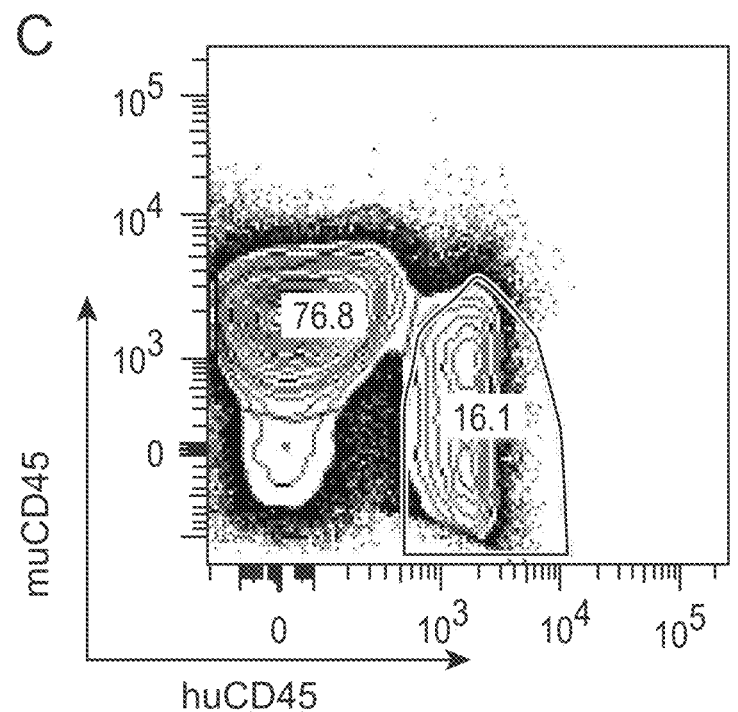
Figure 24:
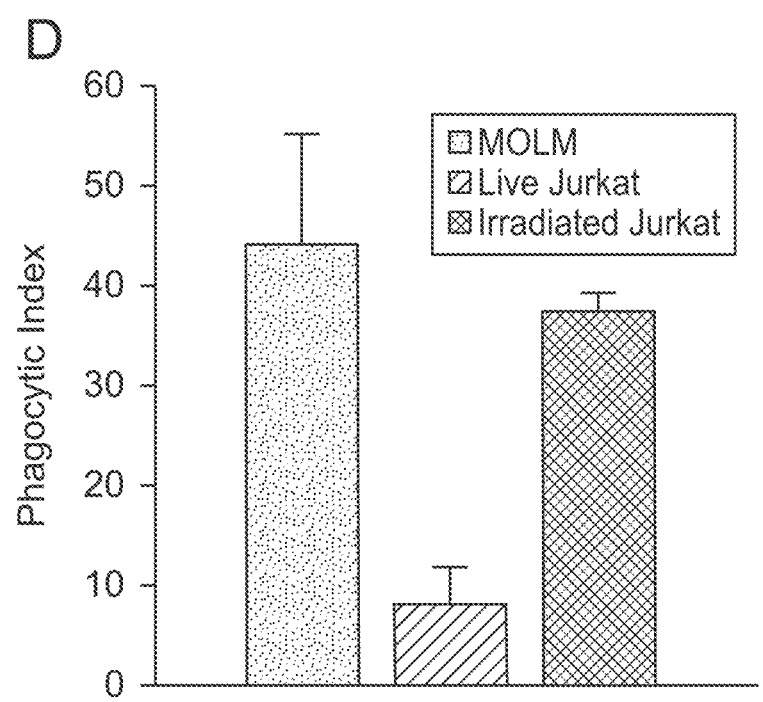

To model the tumorigenic effect of having high versus low CD47 expression, we sorted clones of murine CD47 expressing MOLM-13 cells into high and low expressors. When adjusted for cell size, CD47 density on the CD47$^{lo}$ MOLM-13 cells was approximately equal to mouse bone marrow cells, whereas CD47$^{hi}$ MOLM-13 cells had approximately 9 fold higher expression, an increase commensurate with the change seen in CD47 expression on primary leukemic cells compared to their normal counterparts (FIG. 19a). When high or low expressing cells were transplanted into recipients, only mice transplanted with high expressing cells succumbed to disease by 75 days of age (FIG. 19c). Furthermore, organomegaly was more pronounced in mice transplanted with high expressing cells (FIG. 19d). Mice receiving CD47$^{lo}$ MOLM-13 cells still had notable liver masses. However, the masses were invariably 1-2 large nodes that were well-encapsulated and physically segregated from the liver parenchyma, in marked contrast to tumor masses from CD47hi MOLM-13 cells which consisted of hundreds of small masses scattered throughout the parenchyma. Thus, these large tumor masses consist of cells which have found macrophage free-niches to grow in separate from the main organ body. As expected, the infiltration of MOLM-13 cells in bone marrow and spleen of recipient mice was much higher for mice transplanted with CD47$^{hi}$ MOLM-13 cells as well (FIG. 19e). We also examined the level of CD47 expression in two mice that received CD47$^{lo}$ MOLM-13 cells but had significant marrow engraftment. In both cases, the persisting cells after 75 days had much higher levels of CD47 than the original line (FIG. 19f), indicating that a strong selection pressure exists in vivo for high levels of CD47 expression on leukemic cells. In total, these data indicate that CD47 expression level is a significant factor in tumorigenic potential, and that in a heterogeneous population of leukemic cells, strong selection exists for those clones with high CD47 expression.

We then asked if higher CD47 expression level would provide added protection against macrophage phagocytosis. We performed an in vitro phagocytosis assay with CD47$^{hi}$ and CD47$^{lo}$ MOLM-13 red fluorescent protein (RFP) expressing cells. After incubation with macrophages, far greater numbers of CD47$^{lo}$ cells were phagocytosed as compared to CD47$^{hi}$ cells (FIG. 19g). If phagocytic indices are compared for control MOLM-13 cells, bulk (un-sorted) CD47 MOLM-13 cells, CD47$^{lo}$, and CD47$^{hi}$ MOLM-13 cells, then a direct correlation between CD47 expression level and ability to evade phagocytosis can be seen (FIG. 18a, FIG. 19f). Furthermore, when CD47$^{lo}$ RFP MOLM-13 cells and CD47$^{hi}$ GFP MOLM-13 cells were co-incubated with macrophages in the same wells, the low expressing cells were far more likely to be phagocytosed (FIGS. 19h, 19i). Thus, in a mixed population of cells with varying levels of CD47 expression, the low expressing cells are more likely to be cleared by phagocytic clearance over time.

We also titrated CD47 expression using another method. Since CD47 is expressed in MOLM-13 cells using a Tet-OFF system, we utilized the Tet-inducible promoter element to control expression of CD47 in MOLM-13 cells. Beginning two weeks after transplantation with CD47$^{hi}$ MOLM-13 cells, a cohort of mice was given doxycycline and followed for up to 75 days post-transplant. During this time course, none of the mice given doxycycline succumbed to disease or had large infiltration of MOLM-13 cells in hematopoietic organs (FIGS. 19b-d). At the doses of doxycycline used in this experiment, muCD47 expression in MOLM-13 cells was reduced to levels below that of normal mouse bone marrow, but notably not completely absent (FIG. 19b). Thus, a sustained high level of CD47 expression is required for robust MOLM-13 survival in hematopoietic organs.

Many examples of tumour clearance by T, B, and NK cells have been described in the literature, indicating that a healthy immune system is essential for regulating nascent tumour growth. However, to date, few examples have been produced indicating that macrophage-mediated phagocytosis can check tumour development. Collectively, our studies reveal that ectopic expression of CD47 can enable otherwise immunogenic tumour cells to grow rapidly in a T, B, and NK-cell deficient host. Furthermore, this is likely to reflect a mechanism used by human myeloid leukaemias to evade the host immune system since CD47 is consistently upregulated in murine and human myeloid leukaemias, including all forms of chronic and acute myeloid leukaemia tested thus far. Thus, it appears likely that tumour cells are capable of being recognized as a target by activated macrophages and cleared through phagocytosis. By upregulating CD47, cancers are able to escape this form of innate immune tumour surveillance.

This form of immune evasion is particularly important since these cancers often occupy sites of high macrophage infiltration. CD47 was first cloned as an ovarian tumour cell marker, indicating that it may play a role in preventing phagocytosis of other tissue cancers as well[18]. Furthermore, solid tumours often metastasize to macrophage rich tissues such as liver, lung, bone marrow, and lymph nodes, indicating that they must be able to escape macrophage-mediated killing in those tissues. Finding methods to disrupt CD47-SIRPα interaction may thus prove broadly useful in developing novel therapies for cancer. Preventing CD47-SIRPα interaction could be doubly effective since antigens from phagocytosed tumour cells may be presented by macrophages to activate an adaptive immune response, leading to further tumour destruction.

Methods

Mice. hMRP8bcrabl, hMRP8bcl2, and Fas$^{lpr/lpr}$ transgenic mice were created as previously described and crossed to obtain double transgenics. hMRP8bcl2 homozygotes were obtained by crossing heterozygote mice to each other. C57Bl/6 Ka mice from our colony were used as a source of wild-type cells. For transplant experiments, cells were transplanted into C57Bl/6 RAG2$^{-/-}$ common gamma chain (Gc)$^{-/-}$ mice given a radiation dose of 4 Gy using gamma rays from a cesium irradiator (Phillips). Primary mouse leukemias were transplanted into CD45.2 C57Bl6/Ka mice given a radiation dose of 9.5 Gy. Mice were euthanized when moribund.

Mouse tissues. Long bones were flushed with PBS supplemented with 2% fetal calf serum staining media (SM) Spleens and livers were dissociated using frosted glass slides in SM, then passed through a nylon mesh. All samples were treated with ACK lysis buffer to lyse erythrocytes prior to further analysis.

Quantitative RT-PCR Analysis. Bone marrow was obtained from leukemic hMRP8bcr/ablxhMRP8bcl2 mice or hMRP8bcl2 control mice. Cells were c-Kit enriched using c-Kit microbeads and an autoMACS column (Miltenyi). RNA was extracted using Trizol reagent (Invitrogen) and reverse transcription performed using SuperScriptII reverse polymerase (Invitrogen). cDNA corresponding to approximately 1000 cells was used per PCR reaction. Quantitative PCR was performed with a SYBR green kit on an ABI Prism 7000 PCR (Applied Biosystems) machine at 50° C. for 2 minutes, followed by 95° C. for 10 minutes and then 40 cycles of 95° C. for 15 minutes followed by 60° C. for 1 minute. Beta-actin and 18S RNA were used as controls for cDNA quantity and results of CD47 expression were normalized. Sequences for 18S RNA forward and reverse primers were TTGACGGAAGGGCACCACCAG and GCACCACCACCCACGGAATCG, respectively, for beta-actin were TTCCTTCTTGGGTATGGAAT and GAGCAATGATCTTGATCCTC, and for CD47 were AGGCCAAGTCCAGAAGCATTC and AATCATTCTGCTGCTCGTTGC.

Human Bone Marrow and Peripheral Blood Samples. Normal bone marrow samples were obtained with informed consent from 20-25 year old paid donors who were hepatitis A, B, C and HIV negative by serology (All Cells). Blood and marrow cells were donated by patients with chronic myelomonocytic leukemia (CMML), chronic myeloid leukemia (CML), and acute myelogenous leukemia (AML) and were obtained with informed consent, from previously untreated patients.

Cell lines. MOLM-13 cells were obtained from DSMZ. HL-60 and Jurkat cells were obtained from ATCC. Cells were maintained in Iscove's modified Dulbecco's media (IMDM) plus 10% fetal bovine serum (FBS) (Hyclone). To fractionate MOLM-13 cells into those with high and low CD47 expression, Tet-CD47 MOLM-13 cells were stained with anti-mouse CD47 Alexa-680 antibody (mIAP301). The highest and lowest 5% of mouse CD47 expressing cells was sorted on a BD FACSAria and re-grown in IMDM+10% FCS for 2 weeks. The cells were sorted for three more rounds of selection following the same protocol to obtain the high and low expressing cells used in this study. To obtain red fluorescent protein (RFP) constructs, the mCherry RFP DNA was cloned into Lentilox 3.7 (pLL3.7) empty vector. Lentivirus obtained from this construct was then used to infect cell lines.

Cell staining and flow cytometry. Staining for mouse stem and progenitor cells was performed using the following monoclonal antibodies: Mac-1, Gr-1, CD3, CD4, CD8, B220, and Ter119 conjugated to Cy5-PE (eBioscience) were used in the lineage cocktail, c-Kit PE-Cy7 (eBioscience), Sca-1 Alexa680 (e13-161-7, produced in our lab), CD34 FITC (eBioscience), CD16/32 (FcGRII/III) APC (Pharmingen), and CD135 (Flk-2) PE (eBioscience) were used as previously described to stain mouse stem and progenitor subsets. Mouse CD47 antibody (clone mIAP301) was assessed using biotinylated antibody produced in our lab. Cells were then stained with streptavidin conjugated Quantum Dot 605 (Chemicon). Samples were analyzed using a FACSAria (Beckton Dickinson).

For human samples, mononuclear fractions were extracted following Ficoll density centrifugation according to standard methods and analyzed fresh or subsequent to rapid thawing of samples previously frozen in 90% FCS and 10% DMSO in liquid nitrogen. In some cases, CD34+ cells were enriched from mononuclear fractions with the aid of immunomagnetic beads (CD34+ Progenitor Isolation Kit, Miltenyi Biotec, Bergisch-Gladbach, Germany). Prior to FACS analysis and sorting, myeloid progenitors were stained with lineage marker specific phycoerythrin (PE)-Cy5-conjugated antibodies including CD2 RPA-2.10; CD11b, ICRF44; CD20, 2H7; CD56, B159; GPA, GA-R2 (Becton Dickinson—PharMingen, San Diego), CD3, S4.1; CD4, S3.5; CD7, CD7-6B7; CD8, 3B5; CD10, 5-1B4, CD14, TUK4; CD19, SJ25-C1 (Caltag, South San Francisco, Calif.) and APC-conjugated anti-CD34, HPCA-2 (Becton Dickinson-PharMingen), biotinylated anti-CD38, HIT2 (Caltag) in addition to PE-conjugated anti-IL-3Rα, 9F5 (Becton Dickinson-ParMingen) and FITC-conjugated anti-CD45RA, MEM56 (Caltag) followed by staining with Streptavidin—Texas Red to visualize CD38-BIO stained cells.

Following staining, cells were analyzed using a modified FACS Vantage (Becton Dickinson Immunocytometry Systems, Mountain View, Calif.) equipped with a 599 nm dye laser and a 488 nm argon laser or a FACSAria. Hematopoietic stem cells (HSC) were identified as CD34+ CD38+ CD90+ and lineage negative. Anti-human CD47 FITC (clone B6H12, Pharmingen) was used to assess CD47 expression in all human samples. Fold change for CD47 expression was determined by dividing the average mean fluorescence intensity of CD47 for all the samples of CML-BC, CML-CP, or AML by the average mean fluorescence intensity of normal cells for a given cell population. Common myeloid progenitors (CMP) were identified based on CD34+ CD38+ IL-3Rα+ CD45RA− lin− staining and their progeny including granulocyte/macrophage progenitors (GMP) were CD34+CD38+IL-3Rα+ CD45RA+ Lin− while megakaryocyte/erythrocyte progenitors (MEP) were identified based on CD34+ CD38+ IL-3Rα− CD45RA− Lin− staining.

To determine the density of mouse or human CD47, cells were stained with saturating amounts of anti-CD47 antibody and analyzed on a FACSAria. Since forward scatter is directly proportional to cell diameter, and density is equal to expression level per unit of surface area we used FloJo software to calculate geometric mean fluorescent intensity of the CD47 channel and divided by the geometric mean of the forward scatter value squared ($FSC^2$) to obtain an approximation for density of CD47 expression on the membrane.

Engraftment of MOLM-13 cells was assessed by using anti-human CD45 PE-Cy7 (Pharmingen), anti-mouse CD45.2 APC (clone AL1-4A2), and anti-mouse CD47 Alexa-680 (mIAP301). All samples were resuspended in propidium iodide containing buffer before analysis to exclude dead cells. FACS data was analyzed using FloJo software (Treestar).

Lentiviral preparation and transduction. pRRL.sin-18.PPT.Tet07.IRES.GFP.pre, CMV, VSV, and tet trans-activator (tTA) plasmids were obtained from Luigi Naldini. The full length murine cDNA for CD47 form 2 was provided by Eric Brown (UCSF). The CD47 cDNA construct was ligated into the BamHI/NheI site of Tet-MCS-IRES-GFP. Plasmid DNA was transfected into 293T cells using standard protocols. The supernatant was harvested and concentrated using a Beckman LM-8 centrifuge (Beckman). Cells were transduced with Tet or Tet-CD47-MCS-IRES-GFP and tTA lentivirus for 48 hours. GFP+ cells were sorted to purity and grown for several generations to ensure stability of the transgenes.

Injections. Cells were injected intravenously into the retro-orbital sinuses of recipient mice or via the tail vein as noted. For intra-femoral injections, cells were injected into the femoral cavity of anesthetized mice in a volume of 20 μl using a 27-gauge needle. An isofluorane gas chamber was used to anesthetize mice when necessary.

MOLM-13 cell engraftment. Animals were euthanized when moribund and bone marrow, spleen, and liver harvested. Peripheral blood was obtained by tail bleed of the animals 1 hour prior to euthanization. Engraftment of MOLM-13 cells in marrow, spleen, and peripheral blood was determined as described above. Tumor burden in the liver was determined by calculating the area of each visible tumor nodule using the formula ((length in mm+width in mm)/2)*π. Area of each nodule was then added together per liver.

Doxycycline administration. Doxycycline hydrochloride (Sigma) was added to drinking water at a final concentration of 1 mg/mL. Drinking water was replaced every 4 days and protected from light. In addition, mice received a 10 μg bolus of doxycline by i.p. injection once a week.

Bone marrow derived macrophages (BMDM). Femurs and tibias were harvested from C57Bl/6 Ka mice and the marrow was flushed and placed into a sterile suspension of PBS. The bone marrow suspension was grown in IMDM plus 10% FBS with 10 ng/mL of recombinant murine macrophage colony stimulating factor (MCSF, Peprotech) for 7-10 days.

In vitro phagocytosis assays. BMDM were harvested by incubation in trypsin/EDTA (Gibco) for 5 minutes and gentle scraping. Macrophages were plated at $5\times10^4$ cells per well in a 24-well tissue culture plate (Falcon). After 24 hours, media was replaced with serum-free IMDM. After an additional 2 hours, $2.5\times10^5$ Tet or Tet-CD47 MOLM-13 cells were added to the macrophage containing wells and incubated at 37° C. for the indicated times. After co-incubation, wells were washed thoroughly with IMDM 3 times and examined under an Eclipse T5100 (Nikon) using an enhanced green fluorescent protein (GFP) or Texas Red filter set (Nikon). The number of GFP+ or RFP+ cells within macrophages was counted and phagocytic index was calculated using the formula: phagocytic index=number of ingested cells/(number of macrophages/100). At least 200 macrophages were counted per well. For flow cytometry analysis of phagocytosis macrophages were harvested after incubation with MOLM-13 cells using trypsin/EDTA and gentle scraping. Cells were stained with anti-Mac-1 PE antibody and analyzed on a BD FACSAria. Fluorescent and brightfield images were taken separately using an Eclipse T5100 (Nikon), a super high pressure mercury lamp (Nikon), an endow green fluorescent protein (eGFP) bandpass filter (Nikon) a Texas Red bandpass filter (Nikon), and a RT Slider (Spot Diagnostics) camera. Images were merged with Photoshop software (Adobe).

For in vivo assays, marrow from leg long bones, spleen, and liver were harvested 2 hours after injecting target cells into RAG2−/−,Gc−/− mice. They were prepared into single cell suspensions in PBS plus 2% FCS. Cells were labeled with anti-human CD45 Cy7-PE and anti-mouse F4/80 biotin (eBiosciences). Secondary stain was performed with Streptavidin-APC (eBiosciences). Cells that were human CD45−, F4/80+ were considered to be macrophages, and GFP+ cells in this fraction was assessed.

What is claimed is:

1. A method of treating a human subject for a pre-leukemic condition, the method comprising:
 administering to a human subject in need thereof an antibody that disrupts the binding of CD47 with SIRPα in combination with an antibody that specifically binds to HAVCR2, at a dose that achieves a depletion in pre-leukemic cells by increasing phagocytosis of pre-leukemic cells.

2. The method of claim 1, wherein the antibody that disrupts the binding of CD47 with SIRPα specifically binds to CD47.

3. The method of claim 1, wherein the antibody that disrupts the binding of CD47 with SIRPα is a humanized or chimeric monoclonal antibody.

4. The method of claim 1, wherein the preleukemic condition is a myelodysplastic syndrome.

5. The method of claim 4, wherein the myelodysplastic syndrome is selected from chronic myelogenous leukemia, polycythemia vera, essential thrombocytosis, agnogenic myelofibrosis and myeloid metaplasia.

6. The method of claim 1, wherein the human subject is further treated with a chemotherapeutic drug.

7. The method of claim 1, wherein the antibody that specifically binds to HAVCR2 is a humanized or chimeric monoclonal antibody.

* * * * *